US010118169B2

(12) United States Patent
Lin et al.

(10) Patent No.: US 10,118,169 B2
(45) Date of Patent: Nov. 6, 2018

(54) CHIRAL LIGAND-BASED METAL-ORGANIC FRAMEWORKS FOR BROAD-SCOPE ASYMMETRIC CATALYSIS

(71) Applicants: The University of Chicago, Chicago, IL (US); The University of North Carolina at Chapel Hill, Chapel Hill, NC (US)

(72) Inventors: Wenbin Lin, Chicago, IL (US); Joseph M. Falkowski, Annandale, NJ (US); Takahiro Sawano, Chicago, IL (US)

(73) Assignees: The University of Chicago, Chicago, IL (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/129,851

(22) PCT Filed: Mar. 30, 2015

(86) PCT No.: PCT/US2015/023331
§ 371 (c)(1),
(2) Date: Sep. 28, 2016

(87) PCT Pub. No.: WO2015/149068
PCT Pub. Date: Oct. 1, 2015

(65) Prior Publication Data
US 2017/0173572 A1 Jun. 22, 2017

Related U.S. Application Data

(60) Provisional application No. 61/971,890, filed on Mar. 28, 2014.

(51) Int. Cl.
B01J 31/16 (2006.01)
C07C 45/69 (2006.01)
C07C 231/02 (2006.01)
B01J 31/18 (2006.01)
B01J 31/24 (2006.01)
C07C 227/04 (2006.01)
C07C 29/44 (2006.01)
C07C 41/09 (2006.01)
C07C 67/303 (2006.01)
C07D 307/93 (2006.01)

(52) U.S. Cl.
CPC ....... B01J 31/1691 (2013.01); B01J 31/1805 (2013.01); B01J 31/2409 (2013.01); B01J 31/2447 (2013.01); C07C 29/44 (2013.01); C07C 41/09 (2013.01); C07C 45/69 (2013.01); C07C 67/303 (2013.01); C07C 227/04 (2013.01); C07C 231/02 (2013.01); C07D 307/93 (2013.01); B01J 2531/0263 (2013.01); B01J 2531/0266 (2013.01); B01J 2531/822 (2013.01); C07C 2102/44 (2013.01)

(58) Field of Classification Search
CPC . B01J 31/1691; B01J 31/1805; C07C 67/303; C07C 227/04; C07C 41/09; C07C 231/02; C07C 29/44; C07C 45/69; C07D 307/93
See application file for complete search history.

(56) References Cited

U.S. PATENT DOCUMENTS

| 6,878,838 | B2 | 4/2005 | Lin et al. |
| 8,653,292 | B2 | 2/2014 | Hafizovic et al. |
| 2008/0306315 | A1 | 12/2008 | Lillerud et al. |
| 2012/0115961 | A1 | 5/2012 | Hafizovic et al. |
| 2013/0210157 | A1* | 8/2013 | Chen ............ G01N 31/22 436/80 |
| 2014/0234210 | A1 | 8/2014 | Lin et al. |
| 2016/0346204 | A1 | 12/2016 | Lin et al. |
| 2017/0182486 | A1 | 6/2017 | Lin et al. |

FOREIGN PATENT DOCUMENTS

| WO | WO 2004/084834 A2 | 10/2004 |
| WO | WO 2013/009701 | 1/2013 |
| WO | WO 2015/069926 | 5/2015 |

(Continued)

OTHER PUBLICATIONS

Almqvist et al., New Ligands for the Titanium(rv)-Induced Asymmetric Reduction of Ketones with Catecholborane**Angew. Chem.., Int. Ed., vol. 36, No. 4, pp. 376-377 (1997)
Arrowsmith et al., "Magnesium-catalysed hydroboration of aldehydes and ketones," Chem. Commun., vol. 48, pp. 4567-4569 (2012).
Beck et al., "Synthesis of Rhazinicine by a Metal-Catalyzed C—H Bond Functionalization Strategy ," Angew. Chem. Int. Ed., vol. 47, pp. 3004-3007 (2008).
Blake et al., "Enantioselective Reduction of Prochiral Ketones by Catecholborane Catalysed by Chiral Group 13 Complexes," Chem. Eur. J., vol. 6, No. 19, pp. 3586-3594 (2000).
Bruce et al., "Synthesis of a linear bis-porphyrin with a Ru(phen)22+-complexed 2,2'-bipyridine spacer ," J. Chem. Soc. Perkin Trans., vol. 1, pp. 1226-1231 (2002).

(Continued)

Primary Examiner — John M Mauro
(74) Attorney, Agent, or Firm — Jenkins, Wilson, Taylor & Hunt, P.A.

(57) ABSTRACT

Metal-organic framework (MOFs) compositions based on chiral phosphine-, chiral oxazoline-, chiral pyridine-, and chiral diene-derived organic bridging ligands were synthesized and then post-synthetically metalated with metal precursors such as Ru and Rh complexes. The metal complexes could also be directly incorporated into the MOFs. The MOFs provide a versatile family of recyclable and reusable single-site solid catalysts for catalyzing a variety of asymmetric organic transformations, including the addition of arylboronic acids to α,β-unsaturated ketones and alkimines, the hydrogenation of substituted alkene and carbonyl compounds, and cyclization reactions. The solid catalysts can also be integrated into a flow reactor or a supercritical fluid reactor.

18 Claims, 17 Drawing Sheets

(56) References Cited

FOREIGN PATENT DOCUMENTS

WO  WO 2015/149072  10/2015

OTHER PUBLICATIONS

Campbell et al., "Overcoming the "Oxidant Problem": Strategies to Use O2 as the Oxidant in Organometallic C—H Oxidation Reactions Catalyzed by Pd (and Cu) ," Acc. Chem. Res., vol. 45, No. 6, pp. 851-863 (2012).
Chelussi et al., "Chiral 2,2'-Bipyridines, 1,10-Phenanthrolines, and 2,2':6',2'' Terpyridines:Syntheses and Applications in Asymmetric Homogeneous Catalysis," Chem. Rev., vol. 102, No. 9, pp. 3129-3170 (2002).
Cohen, Postsynthetic Methods for the Functionalization of Metal!Organic Frameworks Chem. Rev., vol. 112, pp. 970-1000 (2011).
Constable et al., "N,N'-Chelating Biheteroaromat Ligands; A Survey," Coord. Chem. Rev., vol. 93, pp. 205-223 (1989).
Das et al., "Functional mixed metal-organic frameworks with metalloligands," Angew Chem Int Ed Engl., vol. 50, pp. 10510-10520 (2011).
Dau et al., "Site-selective cyclometalation of a metal-organic framework," Chem. Sci., vol. 4, pp. 601-605 (2013).
Denmark et al., "Design and Implementation of New, Silicon-Based, Cross-Coupling Reactions: Importance of Silicon-Oxygen Bonds Scott E. Denmark," Acc. Chem. Res., vol. 35, pp. 835-846 (2002).
Dong et al., "Chiral porous organic frameworks forasymmetric heterogeneous catalysis and gas chromatographic separation," Chemical Communications, vol. 50, pp. 14949-14952 (2014).
Evans et al., "Chiral Porous Solids Based on Lamellar Lanthanide Phosphonates," J. Am. Chem. Soc., vol. 123, pp. 10395-10396 (2001).
Evans et al., "Crystal Engineering of NLO Materials Based on Metal-Organic Coordination Networks," Acc. Chem. Res., vol. 35, pp. 511-522 (2002).
Falkowski et al., "Actuation of Asymmetric Cyclopropanation Catalysts: Reversible Single-Crystal to Single-Crystal Reduction of Metal-Organic Frameworks," Angew. Chem., Int. Ed., vol. 50, pp. 8674-8678 (2011).
Falkowski et al., "Metal-Organic Frameworks as Single-Site Solid Catalysts for Asymmetric Reactions," Isr. J. Chem., vol. 52, pp. 591-603 (2012).
Falkowski et al., "Highly Stable and Porous Metal-Organic Frameworks for Asymmetric Catalysis," poster presented at the 245th ACS National Meeting, New Orleans, LA, Apr. 7-11, 1 pg. (2013).
Férey et al., "Crystallized frameworks with giant pores: are there limits to the possible?" Acc. Chem. Res., vol. 38, pp. 217-225 (2005).
Ferey et al., "Large breathing effects in three-dimensional porous hybrid matter: facts, analyses, rules and consequences," Chem. Soc. Rev., vol. 38, pp. 1380-1399 (2009).
Ford and Woodward, "Catalytic Enantioselective Reduction of Ketones by a Chiral Gallium Complex and Catecholborane," Angew. Chem., Int. Ed., vol. 38, No. 3, pp. 335-336 (1999).
Genna et al., "Heterogenization of Homogeneous Catalysts in Metal-Organic Frameworks via Cation Exchange," J. Am. Chem. Soc., vol. 135, pp. 10586-10589 (2013).
Gruning et al., "Bipyridine Periodic Mesoporous Organosilica: A Solid Ligand for the Iridium-Catalyzed Borylation of CH Bonds," Adv. Synth. Catal., vol. 356, pp. 673-679 (2014).
Holmes et al., "One-Pot Borylation/Amination Reactions: Syntheses of Arylamine Boronate Esters from Halogenated Arenes." Org. Lett., vol. 8, No. 7, pp. 1407-1410 (2006).
Hu et al., "Chiral Porous Hybrid Solids for Practical Heterogeneous Asymmetric Hydrogenation of Aromatic Ketones," J. Am. Chem. Soc., vol. 125, pp. 11490-11491 (2003).
Hu, et al., "Remarkable 4,4'-Substituent Effects on Binap: Highly Enantioselective Ru Catalysts for Asymmetric Hydrogenation of β-Aryl Ketoesters and Their Immobilization in Room-Temperature Ionic Liquids," Angew. Chem. Int. Ed., vol. 43, pp. 2501-2504 (2004).
Ihara et al., Easily Attachable and Detachable ortho-Directing Agent for Arylboronic Acids in Ruthenium-Catalyzed Aromatic C—H Silylation J. Am. Chem. Soc., vol. 131, No. 22, pp. 7502-7503 (2009).
Ishiyama et al., "Mild Iridium-Catalyzed Borylation of Arenes. High Turnover Numbers, Room Temperature Reactions, and Isolation of a Potential Intermediate," J. Am. Chem. Soc., vol. 124, No. 3, pp. 390-391 (2001).
Ishiyama et al. "A stoichiometric aromatic CbondH borylation catalyzed by iridium(i)/2,2'-bipyridine complexes at room temperature.," Angew. Chem., Int. Ed., vol. 41, No. 16, pp. 3056-3058 (2002).
Iverson et al., "Stoichiometric and Catalytic B—C Bond Formation from Unactivated Hydrocarbons and Boranes," J. Am. Chem. Soc., vol. 121, pp. 7696-7697 (1999).
Izawa et al., "Aerobic Oxidative Heck/Dehydrogenation Reactions of Cyclohexenones: Efficient Access to meta-Substituted Phenols," Angew. Chem. Int. Ed., vol. 52, pp. 3672-3675 (2013).
Jang et al., "Rhodium-catalyzed reductive cyclization of 1,6-diynes and 1,6-enynes mediated by hydrogen: catalytic C—C bond formation via capture of hydrogenation intermediates," J. Am. Chem. Soc., vol. 126, pp. 7875-7880 (2004).
Jang et al., "Enantioselective Reductive Cyclization of 1,6-Enynes via Rhodium-Catalyzed Asymmetric Hydrogenation: C—C Bond Formation Precedes Hydrogen Activation," J. Am. Chem. Soc., vol. 127, pp. 6174-6175 (2005).
Jones et al., "The Oxidation of the Carbon-Silicon Bond," Tetrahedron, vol. 52, No. 22, pp. 7599-7662 (1996).
Karnahl et al., "Synthesis and Photophysical Properties of 3,8-Disubstituted 1,10-Phenanthrolines and Their Ruthenium(II) Complexes." Eur. J. Inorg. Chem., pp. 4962-4971 (2009).
Kawamorita et al., "Directed Ortho Borylation of Functionalized Arenes Catalyzed by a Silica-Supported Compact Phosphine-Iridium System," J. Am. Chem. Soc., vol. 131, pp. 5058-5059 (2009).
Kesanli et al., "Chiral porous coordination networks: rational design and applications in enantioselective processes," Coord. Chem. Rev., vol. 246, pp. 305-326 (2003).
Khalimon et al., "Catalytic hydroboration by an imido-hydrido complex of Mo(IV)," Chem. Commun., vol. 48, pp. 455-457 (2012).
Kikuchi et al., "Practical synthesis of pinacolborane for one-pot synthesis of unsymmetrical biaryls via aromatic C—H borylation-cross-coupling sequence," Tetrahedron, vol. 64, pp. 4967-4971 (2008).
Kitagawa et al., "Functional Porous Coordination Polymers," Angew. Chem. Int. Ed. Engl, vol. 43, pp. 2334-2375 (2004).
Kong et al., "Assembly and Post-Modification of a Metal-Organic Nanotube for Highly Efficient Catalysis," J. Am. Chem. Soc., vol. 134, pp. 19851-19857 (2012).
Koren-Selfridge et al., A Boron-Substituted Analogue of the Shvo Hydrogenation Catalyst: Catalytic Hydroboration of Aldehydes, Imines, and Ketones, Organomettalics, vol. 28, 2085 (2009).
Kudo et al., "A Versatile Method for Suzuki Cross-Coupling Reactions of Nitrogen Heterocycles," Angew. CHem., Int. Ed., vol. 45, No. 8, pp. 1282-1284 (2006).
Kusaka et al., "meso-Alkynyl BODIPYs: Structure, Photoproperties, π-Extension, and Manipulation of Frontier Orbitals," Chem. Asian J., vol. 8, pp. 723-727 (2013).
Li et al., "Metal-organic frameworks for separations," Chem Rev, vol. 112, pp. 869-932 (2012).
Li et al., Iridium-Catalyzed Regioselective Silylation of Aromatic and Benzylic C—H Bonds Directed by a Secondary AmineAngew. Chem., Int. Ed., vol. 53, 8471 (2014).
Lindsley et al., "Metal Alkoxide Catalysis of Catecbolborane and Borane Reductions Medlanistie Studies.," Tetrahedron Letters, vol. 35, No. 29, pp. 5141-5144 (1994).

(56) References Cited

OTHER PUBLICATIONS

Locatelli et al., "Effective Modular Iminooxazoline (IMOX) Ligands for Asymmetric Catalysis : [Zn(IMOX)]-Promoted Enantioselective Reduction of Ketones by Catecholborane," Angew. Chem., Int. Ed., vol. 42, pp. 4928-4930 (2003).
Love et al., "Preparation of N-Tosylaldimines," Synlett, pp. 493-494 (Jul. 1994).
Ma et al., "A series of isoreticular chiral metal-organic frameworks as tunable platform for asymmetric catalysis," Nature Chemistry, vol. 2, pp. 838-846 (Oct. 2010).
Maleczka et al., "C—H Activation/Borylation/Oxidation: A One-Pot Unified Route to Meta-Substituted Phenols Bearing Ortho-/Para-Directing Groups," J. Am. Chem. Soc., vol. 125, pp. 7792-7793 (2003).
Manna et al., "Salicylaldimine-Based Metal-Organic Framework Enabling Highly Active Olefin Hydrogenation with Iron and Cobalt Catalysts," J. Am. Chem. Soc., vol. 136, 13182-13185 (2014).
Mazzacano et al., "Base Metal Catalysts for Photochemical C—H Borylation That Utilize Metal-Metal Cooperativity." J. Am. Chem. Soc., vol. 135, pp. 17258-17261 (2013).
Mkhalid et al., "C—H Activation for the Construction of C—B Bonds," Chem. Rev., vol. 110, pp. 890-931 (2010).
Morimoto et al., "CO-Transfer Carbonylation Reactions. A Catalytic Pauson-Khand-Type Reaction of Enynes with Aldehydes as a Source of Carbon Monoxide," J. Am. Chem. Soc., vol. 124, pp. 3806-3807 (2002).
Moulton et al., "From molecules to crystal engineering: supramolecular isomerism and polymorphism in network solids," Chem Rev., vol. 101, pp. 1629-1658 (2001).
Mukherjee et al., "Magnesium-catalyzed hydroboration of esters: evidence for a new zwitterionic mechanism," Chemical Science, vol. 5, pp. 959-964 (2014).
Newkome et al., "Synthesis of 2,2'-Bipyridines: Versatile Building Blocks for Sexy Architectures and Functional Nanomaterials," Eur. J. Org. Chem., pp. 235-254 (2004).
Nickerl et al., "Integration of accessible secondary metal sites into MOFs for H2S removal," Inorga. Chem. Front., vol. 1, pp. 325-330 (2014).
Noyori, et al, "Asymmetric Hydrogenation of β-Keto Carboxylic Esters. A Practical, Purely Chemical Access to β-Hydroxy Esters in High Enantiomeric Purity," J. Am. Chem. Soc., vol. 109, pp. 5856-5858 (1987).
Noyori, et al., "BINAP: An Efficient Chiral Element for Asymmetric Catalysis," Acc. Chem. Res., vol. 23, pp. 345-350 (1990).
Noyori, "Asymmetric Catalysis: Science and Opportunities (Nobel Lecture)," Chem., Int. Ed. 2002, vol. 41, pp. 2008-2022 (2002).
Obligacion et al., "Cobalt-Catalyzed C—H Borylation," J. Am. Chem. Soc., vol. 136, pp. 4133-4136 (2014).
Ohta, et al, "Asymmetric Hydrogenation of Unsaturated Carboxylic Acids Catalyzed by BINAP-Ruthenium(II) Complexes," J. Org. Chem., vol. 52, No. 14, pp. 3174-3178 (1987).
Okamoto et al., "Electronic and steric tuning of chiral diene ligands for rhodium-catalyzed asymmetric arylation of imines," Chem. Commun., No. 32, pp. 4815-4817 (Aug. 28, 2009).
Pattison et al., "Enantioselective Rhodium-Catalyzed Addition of Arylboronic Acids to Alkenylheteroarenes," J. Am. Chem. Soc., vol. 132, pp. 14373-14375 (2010).
Preshlock et al., "High-Throughput Optimization of Ir-Catalyzed C—H Borylation: A Tutorial for Practical Applications," J. Am. Chem. Soc., vol. 135, pp. 7572-758 (2013).
Sarvary, et al., "Asymmetric reduction of ketones with catecholborane using 2,6-BODOL complexes of titanium(IV) as catalysts", Chem. Eur. J., vol. 7, No. 10, pp. 2158-2166 (2001).
Schaate et al., "Porous Interpenetrated Zirconium-Organic Frameworks (PIZOFs): A Chemically Versatile Family of Metal-Organic Frameworks," Chem. Eur. J., vol. 17, pp. 9320-9325 (2011).
Shibata et al., "Catalytic Pauson-Khand-Type Reaction Using Aldehydes as a CO Source," Org. Lett., vol. 4, No. 9, pp. 1619-1621 (2002).
Shibata et al., "Rhodium Complex-Catalyzed Pauson-Khand-Type Reaction With Aldehydes as a CO Source," J Org Chem, vol. 67, pp. 7446-7450 (2002).
Shustova et al., "Selective turn-on ammonia sensing enabled by high-temperature fluorescence in metal-organic frameworks with open metal sites," J Am Chem Soc, vol. 135, pp. 13326-13329 (2013).
Siewert, et al, "Rhodium-Catalyzed Enantioselective 1,2-Addition of Aluminum Organyl Compounds to Cyclic Enones," Angew. Chem.Int. Ed., vol., 46, pp. 7122-7124 (2007).
Song et al., "Isoreticular chiral metal-organic frameworks for asymmetric alkene epoxidation: tuning catalytic activity by controlling framework catenation and varying open channel sizes," J Am Chem Soc, vol. 132, pp. 15390-15398 (2010).
Tagata et al., "Continuous-Flow C—H Borylation of Arene Derivatives," Adv. Synth. Catal., vol. 352, pp. 1662-1666 (2010).
Takaya, et al., Rhodium-Catalyzed Asymmetric 1,4-Addition of Aryl- and Alkenylboronic Acids to Enones, Am. Chem. Soc., vol. 120, pp. 5579-5580 (1998).
Tanabe et al., "Stabilizing unstable species through single-site isolation: A catalytically active TaV trialkyl in a porous organic polymer," Chem. Sci., vol. 4, pp. 2483-2489 (2013).
Tanaka et al., "A novel chiral porous metal-organic framework: asymmetric ring opening reaction of epoxide with amine in the chiral open space," Chem. Commun., pp. 820-822 (2008).
Torbati et al., "Dichlorido(6,6'-dimethyl-2,2'-bipyridine-K2N,N')cobalt(II)," Acta Crystallographica, vol. E66, pp. m1284 plus supporting information (7 pages total) (2010).
Wang et al., "Elucidating Molecular Iridium Water Oxidation Catalysts Using Metal-Organic Frameworks: A Comprehensive Structural, Catalytic, Spectroscopic, and Kinetic Study," J. Am. Chem. Soc., vol. 134, pp. 19895-19908 (2012).
Wu et al., "A homochiral porous metal-organic framework for highly enantioselective heterogeneous asymmetric catalysis," J Am Chem Soc, vol. 127, pp. 8940-8941 (2005).
Wu, et al., "Recyclable Silica-Supported Iridium Bipyridine Catalyst for Aromatic C—H Borylation," ACS Catal. pp. 1365-1375 (2014).
Yoon, et al., "Privileged Chiral Catalysts," Science, vol. 299, pp. 1691-1693 (Mar. 14, 2003).
Yoon et al., "Homochiral metal-organic frameworks for asymmetric heterogeneous catalysis," Chem Rev, vol. 112, pp. 1196-1231 (2012).
Zheng et al., "Cavity-induced enantioselectivity reversal in a chiral metal-organic framework Brønsted acid catalyst," Chem. Sci., vol. 3, pp. 2623-2627 (2012).
Zhou, et al., "BINAP", Privileged Chiral Ligands and Catalysts; Wiley-VCH: Weinheim, Germany, pp. 1-53 (2011).
Zhu et al., "Chiral Nanoporous Metal-Metallosalen Frameworks for Hydrolytic Kinetic Resolution of Epoxides," J. Am. Chem. Soc., vol. 134, pp. 8058-8061 (2012).
Balskus, "Chiral Diene-Metal Complexes in Asymmetric Catalysis," F. Angew. Chem., Int. Ed., vol. 43, pp. 1-4 (2004).
Bloch et al., "Metal Insertion in a Microporous Metal-Organic Framework Lined with 2,2'-Bipyridine", J. Am. Chem. Soc., vol. 132, pp. 14382-14384 (Sep. 17, 2010).
Cavka et al., "A New Zirconium Inorganic Building Brick Forming Metal Organic Frameworks with Exceptional Stability," J. Am. Chem. Soc., vol. 130, No. 42, pp. 13850-13851 (2008).
Cho et al., "Remarkably selective iridium catalysts for the elaboration of aromatic C—H bonds," Science, vol. 295, No. 5553, pp. 305-308 (Jan. 11, 2002).
Cho et al., "A metal-organic framework material that functions as an enantioselective catalyst for olefin epoxidation," Chem. Commun., pp. 2563-2565 (2006).
Falkowski et al., "Privileged phosphine-based metal-organic frameworks for broad-scope asymmetric catalysis," Journal of the American Chemical Society, vol. 136, No. 14, pp. 5213-5216 (Mar. 31, 2014).
Fei et al., "A robust, catalytic metal-organic framework with open 2,2'-bipyridine sites," Chemical Communications, vol. 50, pp. 4810-4812 (published online Mar. 21, 2014).

(56) References Cited

OTHER PUBLICATIONS

Furukawa, et al., "The Chemistry and Applications of Metal-Organic Frameworks," Science, vol. 341, pp. 974-986 (Aug. 30, 2013).
Hadlington et al., "Low Coordinate Germanium(II) and Tin(II) Hydride Complexes: Efficient Catalysts for the Hydroboration of Carbonyl Compounds," J. Am. Chem. Soc., vol. 136, pp. 3028-3031 (Feb. 2014).
Hartwig, "Borylation and Silylation of C—H Bonds: A Platform for Diverse C—H Bond Functionalizations," Acc. Chem. Res., vol. 45, No. 6, pp. 864-873 (2012).
Hayashi et al., "Rhodium-catalyzed asymmetric 1,4-addition and its related asymmetric reactions.," Chem. Rev., vol. 103, No. 8, pp. 2829-2844 (2003).
He et al., "Nanoscale Metal-Organic Frameworks for the Co-delivery of Cisplatin and Pooled siRNAs to Enhance Therapeutic Efficacy in Drug-resistant Ovarian Cancer Cells," J. Am. Chem. Soc., vol. 136, 5181-5184 (2014).
Horcajada et al., "Metal-organic frameworks in biomedicine"m Chem. Rev. vol. 112, No. 8, pp. 1232-1268 (2012).
Hu et al., "Chiral, porous, hybrid solids for highly enantioselective heterogeneous asymmetric hydrogenation of beta-keto esters," Angewandte Chemie International Ed. vol. 42, pp. 6000-6003 (2003).
Izawa et al., Science, "Palladium-Catalyzed Aerobic Dehydrogenation of Substituted Cyclohexanones to Phenols," vol. 333, 209-213 (Jul. 8, 2011).
Kaes et al., "Bipyridine: the most widely used ligand. A review of molecules comprising at least two 2,2'-bipyridine units.," Chem. Rev., vol. 100, pp. 3553-3590 (Oct. 11, 2000).
Kandiah et al., "Synthesis and Stability of Tagged UiO-66 Zr-MOFs," Chem. Mater., vol. 22, No. 24, pp. 6632-6640 (2010).
Kreno et al., "Metal Organic Framework Materials as Chemical Sensors," Chem. Rev., vol. 112, pp. 1105-1125 (2012).
Lan et al., "A luminescent microporous metal-organic framework for the fast and reversible detection of high explosives," Angew Chem Int Ed Engl, vol. 48, pp. 2334-2338 (2009).
Lee et al., "Metal-organic framework materials as catalysts," Chem. Soc. Rev., vol. 38, 1450-1459 (2009).
Li et al., "Design and synthesis of an exceptionally stable and highly porousmetal-organic framework," Nature, vol. 402, 276-279 (Nov. 18, 1999).
Li et al., "High gas storage capacities and stepwise adsorption in a UiO type metal-organic framework incorporating Lewis basic bipyridyl sites," Chemical Communications, vol. 50, pp. 2304-2307 (2014).
Lau et al., "PLUXter: Rapid discovery of metal organic framework structures using PCA and HCA of high throughput synchrotron powder diffraction data," Combinatorial Chem. & High Throughput Screening, vol. 14, pp. 28-35 (2011).
Ma et al., "Enantioselective catalysis with homochiral metal-organic frameworks," Chemical Society Reviews, vol. 38, No. 5, pp. 1248-1256 (Feb. 23, 2009).
Manna et al., "Postsynthetic metalation of bipyridyl-containing metal-organic frameworks for highly efficient catalytic organic transformations," J. Am. Chem. Soc., vol. 136, pp. 6566-6569 (Apr. 23, 2014).
Miyashita, et al., "Synthesis of 2,2'-bis(diphenylphosphino)-1,1'-binaphthyl (BINAP), an atropisomeric chiral bis(triaryl)phosphine, and its use in the rhodium(I)-catalyzed asymmetric hydrogenation of .alpha.-(acylamino)acrylic acids," J. Am. Chem. Soc., vol. 102, No. 27, pp. 7932-7934 (Dec. 1980).
Miyaura et al., "Palladium-Catalyzed Cross-Coupling Reactions of Organoboron Compounds," Chem. Rev., vol. 95, pp. 2457-2483 (1995).
Murphy et al., "Meta Halogenation of 1,3-Disubstituted Arenes via Iridium-Catalyzed Arene Borylation," J. Am. Chem. Soc., vol. 129, pp. 15434-15435 (2007).
Notification Concerning Transmittal of International Preliminary Report on Patentability (Chapter I of the Patent Cooperation Treaty) corresponding to PCT/US2015/023331 dated Oct. 13, 2016.
Notification Concerning Transmittal of International Preliminary Report on Patentability (Chapter I of the Patent Cooperation Treaty) corresponding to PCT/US2015/023387 dated Oct. 13, 2016.
Notification of Transmittal of the International Search Report and the Written Opinion of the International Searching Authority, or the Declaration corresponding to PCT/US2015/023331 dated Jul. 7, 2015.
Notification of Transmittal of the International Search Report and the Written Opinion of the International Searching Authority, or the Declaration corresponding to PCT/US2015/023387, dated Jun. 24, 2015.
Oluyadi et al., "Titanocene(II)-Catalyzed Hydroboration of Carbonyl Compounds," Organometallics, vol. 32, pp. 70-78 (2012).
Ravel et al., "Athena, Artemis, Hephaestus: data analysis for X-ray adsorption spectroscopy using IFEFFIT," Jour. Synchrotron Radiation, vol. 12, pp. 537-541 (2005).
Rehr, "Theoretical approaches to x-ray absorption fine structure," Rev. Mod. Phys., vol. 72, No. 3, p. 621-654 (Jul. 2000).
Roosen et al., "Outer-Sphere Direction in Iridium C—H Borylation," J. Am. Chem. Soc., vol. vol. 134, No. 28, pp. 11350-11353 (Jul. 18, 2012).
Saitoh et al., "Preparatioin of symmetric dibromides of 1,10-phenanthroline," Can. J. Chem., vol. 75, pp. 1336-1339 (1997).
Sawano et al., "Chiral Diene-Based Metal-Organic Frameworks for Highly Enantioselective Carbon-Carbon Bond Formation Reactions," Chem. Sci., 6, pp. 1-6 (2015).
Sawano et al., "Robust, Chiral, and Porous BINAP-Based Metal-Organic Frame-works for Highly Enantioselective Cyclization Reactions", J.Am. Chem. Soc., vol. 137, pp. 12241-12248 (Sep. 2015).
Schaate et al., "Modulated Synthesis of Zr-Based Metal-Organic Frameworks: From Nano to Single Crystals," Chemistry—A European Journal, vol. 17, pp. 6643-6651 (2011).
Schwab et al., "Preparation of 5-Brominated and 5,5'-Dibrominated 2,2'-Bipyridines and 2,2'-Bipyrimidines," J. Org. CHem., vol. 67, No., pp. 443-449 (2002).
Sigman et al., "Imparting catalyst control upon classical palladium-catalyzed alkenyl C—H bond functionalization reactions," Acc. Chem. Res., vol. 45, No. 6, pp. 874-884 (2012).
Simmons et al., "Iridium-Catalyzed Arene Ortho-Silylation by Formal Hydroxyl-Directed C—H Activation," J. Am. CHem. Soc., vol. 132, No. 48, pp. 17092-17095 (Nov. 15, 2010).
Sheldrick, "A short history of SHELX," Acta Cryst., vol. A64, pp. 112-122 (2008).
Song et al., "Chiral porous metal-organic frameworks with dual active sites for sequential asymmetric catalysis," Proc. R. Soc., vol. 468, pp. 2035-2058 (Mar. 14, 2012).
Suh et al., "Hydrogen Storage in Metal-Organic Frameworks," Chem. Rev., vol. 112, No. 2, pp. 782-835 (2012).
Sumida et al., "Carbon dioxide capture in metal-organic frameworks," Chem. Rev., vol. 112, pp. 724-781 (2012).
Tamao et al., "Hydrogen Peroxide Oxidation of the Silicon-Carbon Bond in Organoaikoxysiiane." Organometallics, vol. 2, No. 11, 1694-1696 (1983).
Tzschucke et al., "Arenes to Anilines and Aryl Ethers by Sequential Iridium-Catalyzed Borylation and Copper-Catalyzed Coupling", Organic Letters, vol. 9, No. 5, pp. 761-764 (2007).
Uemura et al., "Polymerization reactions in porous coordination polymers," Chem. Rev., vol. 38, No. 5, pp. 1-9 (2009).
Wan, et al., "Cross-coupling of remote meta-C—H bonds directed by a U-shaped template," J. Am. Chem. Soc., vol. 135, 18056-18059 (2013).
Wang et al., "Doping metal-organic frameworks for water oxidation, carbon dioxide reduction, and organic photocatalysis.," J. Am. Chem. Soc., vol. 133, No. 34, pp. 13445-13454 (2011).
Wang et al., "Metal-organic Frameworks as a Tunable Platform for Designing Functional Molecular Materials," J. Am. Chem. Soc., vol. 135, No. 36, pp. 1-32 (Sep. 11, 2013).
Wiers et al., "A solid lithium electrolyte via addition of lithium isopropoxide to a metal-organic framework with open metal sites," J Am Chem Soc, vol. 133, No. 37, pp. 14522-14525 (Aug. 30, 2011).

(56) References Cited

OTHER PUBLICATIONS

Yinghuai et al., "Catalytic Phenylborylation Reaction by Iridium(0) Nanoparticles Produced from Hydridoiridium Carborane," Inorg. Chem., vol. 47, No. 13, pp. 5756-5761 (2008).
Office Action (Restriction Requirement) corresponding to U.S. Appl. No. 15/129,853 dated Jun. 1, 2018.

* cited by examiner

Proposed rhodacycle intermediate in the MOF

CHIRAL LIGAND-BASED METAL-ORGANIC FRAMEWORKS FOR BROAD-SCOPE ASYMMETRIC CATALYSIS

RELATED APPLICATIONS

The presently disclosed subject matter claims the benefit of U.S. Provisional Patent Application Ser. No. 61/971,890, filed Mar. 28, 2014; the disclosure of which is incorporated herein by reference in its entirety.

STATEMENT OF GOVERNMENT SUPPORT

This invention was made with government support under Grant Number CA151455 awarded by the National Institutes of Health and Grant Number DMR0906662 awarded by the National Science Foundation. The government has certain rights in the invention.

TECHNICAL FIELD

The presently disclosed subject matter relates to metal-organic framework (MOF) materials containing chiral phosphine-, chiral oxazoline-, chiral pyridine-, and chiral diene-derived organic bridging ligands, their preparation, and their use as enantioselective heterogeneous catalysts for organic transformations, such as the addition of arylboronic acids to α,β-unsaturated ketones and alkimines as well as other carbon-carbon bond formation reactions, the hydrogenation of substituted alkene and carbonyl compounds, and cyclization reactions.

ABBREVIATIONS

Å=angstrom
° C.=degrees Celsius
%=percentage
μL=microliter
μmol=micromole
acac=acetylacetonate
Ar=aryl
atm=atmosphere
BINAP=(2,2'-bis(diphenylphosphino)-1,1-binaphthyl)
BINOL=1,1'-bi-2-naphthol
cod=cyclooctadiene
DCE=dichloroethane
DMF=dimethylformamide
DMSO=dimethylsulfoxide
e.e. (or ee)=enantiomeric excess
EtOH=ethanol
EXFAS=extended x-ray absorption fine structure
g=gram
h=hour
HPLC=high performance liquid chromatography
ICP-MS=inductively coupled plasma-mass spectrometry
kg=kilogram
mg=milligram
min=minute
mL=milliliter
mM=millimolar
mmol=millimole
MOF=metal-organic framework
mol=mole
nbd=norbornadiene
nm=nanometer
NMOF=nano-metal-organic frameworks
NMR=nuclear magnetic resonance
Ph=phenyl
PXRD=power x-ray diffraction
Rh=rhodium
r.t. (or rt)=room temperature
Ru=ruthenium
SBU=secondary building unit
TFA=trifluoroacetic acid
TGA=thermogravimetric analysis
TLC=thin layer chromatography
TON=turn over number
XAFS=x-ray absorption fine structure spectroscopy
XANES=x-ray absorption near edge structure
Zr=zirconium
Hf=hafnium

BACKGROUND

Metal-organic frameworks (MOFs) are an emerging class of porous molecular materials (see Moulton et al., Chem. Rev., 2001, 101, 1629; Evans et al., Acc. Chem. Res., 2002, 35, 511; Lan et al., Angew. Chem., Int. Ed., 2009, 48, 2334; Uemura et al., Chem. Soc. Rev., 2009, 38, 1228; Das et al., Angew. Chem., Int. Ed., 2011, 50, 10510; Wiers et al., J. Am. Chem. Soc., 2011, 133, 14522; Kreno et al., Chem. Rev., 2012, 112, 1105; Li et al., Chem. Rev., 2012, 112, 869; Furukawa et al., Science, 2013, 341; and Shustova et al., J. Am. Chem. Soc., 2013, 135, 13326) assembled from organic linkers and metal ions or metal cluster nodes. They find application in gas storage (e.g., hydrogen, carbon dioxide, and methane storage), molecule separation, and drug delivery. MOFs can also provide a highly tunable platform to engineer heterogeneous catalysts for chemical reactions, including asymmetric organic transformations and/or transformations that cannot be achieved with traditional porous inorganic materials. See Kesanli et al., Coord. Chem. Rev., 2003, 246, 305.

Some asymmetric MOF catalysts have been reported that can provide enantio-differentiation. See Ma et al., Chem. Soc. Rev., 2009, 38, 1248; Falkowski et al., Isr. J. Chem., 2012, 52, 591; and Yoon et al., Chem. Rev., 2012, 112, 1196. The first MOF catalyst with significant enantiomeric excesses (e.e.'s) contained the $C_2$-symmetric 1,1'-bi-2-naphthol (BINOL). See Evans et al., J. Am. Chem. Soc., 2001, 123, 10395; and Wu et al., J. Am. Chem. Soc., 2005, 127, 8940. The postsynthetically-generated Ti-BINOLate moiety in the chiral MOF was responsible for high e.e.'s observed for diethylzinc additions to aromatic aldehydes. See Wu et al., J. Am. Chem. Soc., 2005, 127, 8940. Subsequently, a Mn-salen-based MOF was used for the asymmetric epoxidation of alkenes. See Cho et al., Chem. Commun. 2006, 2563. Since these reports, additional stereoselective MOF catalysts have been developed based on BINOL- and salen-based ligands. See Tanaka et al., Chem. Commun., 2008, 820; Ma et al., Nat. Chem., 2010, 2, 838; Song et al., J. Am. Chem. Soc., 2010, 132, 15390; Falkowski et al., Angew. Chem., Int. Ed., 2011, 50, 8674; Zheng et al., Chem. Sci., 2012, 3, 2623; and Shu et al., J. Am. Chem. Soc., 2012, 134, 8058.

However, there remains an ongoing need in the art for additional heterogeneous catalysts for asymmetric catalysis. In particular, there is an ongoing need for additional catalysts that employ other chiral ligands and that have good efficiency and enantioselectivity and/or that have good stability and recyclability. For example, there is an ongoing need for additional heterogeneous catalysts that can catalyze reactions at low catalyst loadings. Further, there is a need for additional heterogeneous catalysts to catalyze additional types of enantioselective reactions.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

Disclosed herein in some embodiments is a method for preparing a stable, crystalline, and/or porous metal-organic framework (MOF), wherein said crystalline and porous MOF comprises periodic repeats of a metal-based secondary building unit (SBU) and a chiral bridging ligand. In some embodiments, the method comprises providing a chiral bridging ligand, wherein said chiral bridging ligand is selected from a chiral phosphine, a chiral oxazoline, a chiral pyridine, and a chiral diene; and contacting the chiral bridging ligand with a first metal source to obtain the crystalline and porous MOF. In some embodiments, the chiral bridging ligand is substituted with one or more carboxylate, pyridine, and/or phosphonate moieties. In some embodiments, the chiral bridging ligand is a dicarboxylate, a tricarboxylate, a tetracarboxylate, a bipyridine, a tripyridine, a tetrapyridine, a diphosphonate, a triphosphonate, or a tetraphosphonate.

In some embodiments, the chiral bridging ligand is a carboxylate, pyridine, or phosphonate derivative of a chiral bisphosphine. In some embodiments, the chiral bridging ligand is a chiral phosphine further comprising at least two substituents selected from the group consisting of carboxylate, pyridine, and phosphonate. In some embodiments, the chiral bridging ligand is a dicarboxylate-substituted chiral bisphosphine. In some embodiments, the chiral bridging ligand comprises a 2,2-bis(diphenylphosphino)-1,1'-binaphthyl (BINAP) derivative with 4,4' substituents comprising carboxylate groups. In some embodiments, the chiral bridging ligand is 4,4'-Bis(4-carboxyphenylethynyl)BINAP.

In some embodiments, the chiral bridging ligand is a chiral diene further comprising at least two substituents selected from the group consisting of carboxylate, pyridine, and phosphonate. In some embodiments, the chiral bridging ligand is a dicarboxylate-substituted chiral diene. In some embodiments, the chiral bridging ligand is a chiral bicycle [2.2.2]octa-2,5-diene. In some embodiments, the chiral bridging ligand is 4,4'-((2-((1R,4R,7R)-7-isopropyl-5-methylbicyclo[2.2.2]octa-2,5-diene-2-carboxamido)-[1,1'-biphenyl]-4,4'-diyl)bis(ethyne-2,1-diyl)dibenzoic acid or a stereoisomer thereof.

In some embodiments, the SBU is selected from the group consisting of Zr-oxo clusters, Hf-oxo clusters, Zn-oxo clusters, Ti-oxo clusters, Cu-carboxylate paddlewheels, and other SBUs used to construct MOFs. In some embodiments, the first metal source is a metal alkoxide or a metal halide. In some embodiments, the first metal source is $ZrCl_4$ or $HfCl_4$.

In some embodiments, the method further comprises contacting the crystalline and porous MOF with a second metal source to metalate the organic bridging ligand. In some embodiments, the second metal source comprises Fe, Co, Ni, Rh, Ru, Ir, Os, Pt, or Pd. In some embodiments, the second metal source is $Ru(cyclooctadiene)(2-Me-allyl)_2$, $Rh(norbornadiene)_2BF_4$, $[RhCl(C_2H_2)_2]_2$, or $Rh(acetylacetonate)(C_2H_4)_2$. In some embodiments, the MOF further comprises a non-chiral bridging ligand, optionally wherein the non-chiral bridging ligand is 4,4'((2-nitro-[1,1'-biphenyl]-4,4'-diyl))bis(ethyne-2,1-diyl))dibenzoic acid or 4,4'-(2-nitro[1,1'-biphenyl]bisbenzoic acid. In some embodiments, the chiral bridging ligand and the first metal source are contacted in a solvent or mixture of solvents selected based on solvent molecule size, such that the sizes and/or shapes of internal pores, cavities, and/or open channels in the crystalline and porous MOF can be tailored to enhance catalytic activity and selectivity. In some embodiments, the solvent comprises dimethylformamide (DMF).

In some embodiments, disclosed is an asymmetric heterogeneous catalyst comprising a crystalline and porous MOF, wherein said crystalline and porous MOF comprises periodic repeats of a metal-based secondary building unit (SBU), wherein said metal-based SBU comprises a first metal, and a chiral bridging ligand, wherein said chiral bridging ligand is further complexed to a second metal and wherein said chiral bridging ligand is selected from a chiral phosphine, a chiral oxazoline, a chiral pyridine, and a chiral diene. In some embodiments, the SBU is a Zr-oxo cluster. In some embodiments, the second metal is Ru or Rh.

In some embodiments, disclosed is a catalyst prepared according to the presently disclosed methods. In some embodiments, the chiral bridging ligand is a dicarboxylate-substituted chiral bisphosphine or a dicarboxylate-substituted chiral bicyclo[2.2.2]octane-2,5-diene. In some embodiments, the catalyst further comprises a non-chiral bridging ligand, optionally wherein the non-chiral bridging ligand is 4,4'((2-nitro-[1,1'-biphenyl]-4,4'-diyl))bis(ethyne-2,1-diyl))dibenzoic acid or 4,4'-(2-nitro[1,1'-biphenyl]bisbenzoic acid.

In some embodiments, disclosed is method for preparing an asymmetric compound. In some embodiments, the method comprises contacting a substrate capable of forming an asymmetric product by an asymmetric reaction with an asymmetric heterogeneous catalyst as disclosed herein. In some embodiments, the asymmetric reaction is selected from the group consisting of hydrogenation; isomerization, optionally the isomerization of an allylamine, an allyl alcohol, or an α,β-unsaturated ketone; allylic substitution; a coupling reaction, optionally wherein the coupling reaction is a Buchwald-Hartwig amination, an intramolecular Heck reaction, or an intermolecular Heck reaction; conjugate addition, optionally wherein the conjugate addition is a Michael addition or an azo-Michael addition; an aldol reaction; a Mannich-type reaction; nucleophilic addition, optionally wherein the nucleophilic addition is to a carbonyl or imine group and/or wherein the nucleophilic addition is a cyanation, a propargylation, an allylation, a dienylation, an arylation, an alkenylation, or an alkylation; hydroformylation; hydroacylation; hydroboration; hydroamination; intra- or intermolecular hydrosilylation; an α-substitution reaction, optionally wherein the α-substitution reaction is a protonation, a fluorination, an amination, an arylation, or an orthoester alkylation; an ene reaction; a Diels-Alder reaction; a Pauson-Khand reaction; an Alder-Ene reaction, an enyne intramolecular cyclization; a [2+2+2] cycloaddition; a [3+2] cycloaddition; and a ring-opening reaction. In some embodiments, the asymmetric reaction is performed in the presence or absence of a solvent, optionally wherein when a solvent is present, further optionally wherein the solvent is an unconventional solvent, such as supercritical carbon dioxide. In some embodiments, the asymmetric reaction is performed in a flow reactor. In some embodiments, the asymmetric reaction is selected from the group consisting of 1,4-addition of an arylboronic acid to an α,β-unsaturated ketone; 1,2-addition of trimethylaluminum to an α,β-unsaturated ketone, 1,2-addition of an arylboronic acid to an aldimine, hydrogenation of a β-keto ester, hydrogenation of a substituted alkene, reductive cyclization of a 1,6-enyne, an Alder-Ene reaction, and a Pauson-Khand reaction. In some embodiments, the contacting is performed by contacting the substrate with about 3 mole percentage or less of the catalyst as compared to the substrate.

In some embodiments, disclosed is a method of preparing a compound, wherein the method comprises using a catalyst as disclosed herein to catalyze a multi-step reaction or to catalyze sequential reactions.

In some embodiments, disclosed is a method of preparing a compound, wherein the method comprises using a plurality of catalysts as disclosed herein to catalyze sequential reactions or to catalyze a multi-step reaction.

Accordingly, it is an object of the presently disclosed subject matter to provide metal-organic framework (MOFs) materials comprising chiral phosphine-, chiral oxazoline-, chiral pyridine-, and chiral diene-based bridging ligands, as well as methods of making and using the MOFs. This and other objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). A further understanding of the presently disclosed subject matter can be obtained by reference to an embodiment set forth in the illustrations of the accompanying drawings. Although the illustrated embodiment is merely exemplary of the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, but merely to clarify and exemplify the presently disclosed subject matter.

For a more complete understanding of the presently disclosed subject matter, reference is now made to the following drawings in which:

FIG. 7 is a drawing showing the use of an exemplary metal-organic framework (MOF)-based catalyst comprising a chiral phosphine organic bridging ligand in the asymmetric catalysis of the Alder-Ene cyclization of a 1,6 enyne, 17a.

DETAILED DESCRIPTION

Figure 1:
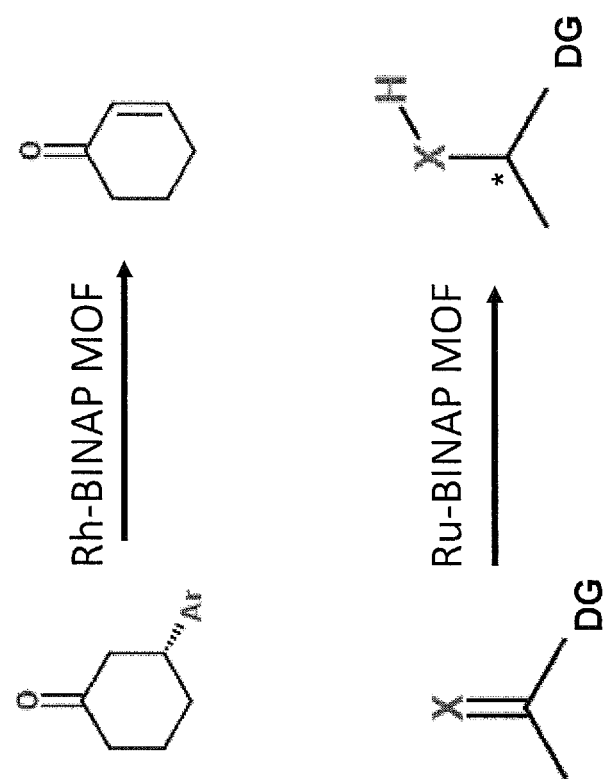
FIG. 1 is a schematic drawing showing some representative catalytic activities for a ruthenium (Ru) or rhodium (Rh) metalated metal-organic framework (MOF) comprising a (2,2'-bis(diphenylphosphino)-1,1-binaphthyl) (BINAP)-based organic bridging ligand and zirconium-oxo clusters, i.e., Ru-BINAP MOF or Rh-BINAP MOF. Ar refers to an aryl group, DG refers to a donating group, X can be, for example, O or NH, and * indicates a chiral center.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl or substituted alkyl, and wherein at least one R is alkyl or substituted alkyl. "Arylamine" and "aminoaryl" refer to the group —N(R)$_2$ wherein each R is H, aryl, or substituted aryl, and wherein at least one R is aryl or substituted aryl, e.g., aniline (i.e., —NHC$_6$H$_5$).

The terms "halo", "halide", or "halogen" as used herein refer to fluoro, chloro, bromo, and iodo groups.

The term "hydroxyl" refers to the —OH group.

The terms "mercapto" or "thiol" refer to the —SH group.

The terms "carboxylate" and "carboxylic acid" can refer to the groups —C(=O)O$^-$ and —C(=O)OH, respectively. In some embodiments, "carboxylate" can refer to either the —C(=O)O$^-$ or —C(=O)OH group.

The term "phosphonate" refers to the —P(=O)(OR)$_2$ group, wherein each R can be independently H, alkyl, substituted alkyl, aralkyl, substituted aralkyl, aryl, substituted aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphine" refers to the —P(R)$_3$ group, wherein each R is independently H, alkyl, substituted alkyl, aralkyl, substituted aralkyl, aryl, or substituted aryl.

The term "silyl" refers to groups comprising silicon atoms (Si).

The term "diene" refers to a compound or chemical moiety that contains two double bonds, e.g., two carbon-carbon double bonds.

The term "pyridine" refers to a compound or chemical moiety that comprises a heteroaryl group with a six-membered backbone, wherein the six-membered backbone comprises five carbon atoms and one nitrogen atom. The pyridine can optionally be substituted by one or more aryl group substituents.

The term "oxazoline" refers to a compound or chemical moiety that comprises a heterocyclic group with a five-membered backbone, wherein the five-membered backbone comprises one oxygen atom and one nitrogen atom. The group further comprises one double bond. The oxazoline can be a 2-, 3-, or 4-oxazoline. The oxazoline can optionally be substituted by one or more alkyl group substituents.

The term "chiral" refers to the geometric property of a rigid object (or spatial arrangement of points or atoms in a chemical compound) of being non-superimposable on its mirror image. If the object is superimposable on its mirror image the object is described as being achiral or non-chiral. In some embodiments, a chiral molecule can comprise a "chiral center" or "stereogenic center", which refers to an atom attached to a set of substituents wherein interchanging any two substituents results in a stereoisomer. In some embodiments, the chiral center is an asymmetric carbon atom. Each chiral center (*C) can be labeled R or S according to a system by which its substituents are each designated a priority according to the Cahn Ingold Prelog priority rules (CIP), based on atomic number. In some embodiments, the stereochemistry of the chiral centers (marked by "*C") represents all possible combinations in terms of relative and absolute chemistry. In some embodiments, a chiral molecule does not contain a chiral center, but instead has axial chirality, i.e., an axis about which a set of substituents is held in a spatial arrangement that is not superimposable upon its mirror image, or inherent chirality (e.g., as a result of curvature of the molecule).

The term "isomer" as used herein refers to one of two or more molecules having the same number and kind of atoms and hence the same molecular weight, but differing in chemical structure. Isomers can differ in the connectivities of the atoms (structural isomers), or they can have the same atomic connectivities but differ only in the arrangement or configuration of the atoms in space (stereoisomers). "Stereoisomer" or "stereoisomers" refer to compounds that differ in chirality, e.g., that differ in the chirality of one or more stereocenters. Stereoisomers can include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images.

As used herein, the term "metal-organic matrix material" refers to a solid material comprising both metal and organic components, wherein the organic components include at least one, and typically more than one carbon atom. In some embodiments, the material is crystalline. In some embodiments, the material is porous. In some embodiments, the metal-organic matrix material is a coordination polymer, which comprises repeating units of coordination complexes comprising a metal-based secondary building unit (SBU), such as a metal ion or metal complex, and a bridging polydentate (e.g., bidentate) organic ligand. In some embodiments, the material contains more than one type of metal ion. In some embodiments, the material can contain more than one type of organic bridging ligand.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably.

The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —$CO_2H$, —$NO_2$, amino, hydroxyl, thio, thioalkyl, —$B(OH)_2$, —$SO_3H$, $PO_3H$, phosphonate, and heteroatoms (e.g., nitrogen, oxygen, or sulfur) in heterocycles. In some embodiments, in addition to binding to at least two metal ions or complexes in an MOF, the bridging ligand can also bind to a further metal ion or complex, e.g., to provide a catalytic moiety.

As used herein, turn over number (TON) refers to the number of moles of substrate that a mole of catalyst can convert before being inactivated.

As used herein, the term "stable" refers to a characteristic of a MOF of the presently disclosed subject matter. A "stable" MOF refers to a MOF that retains its framework structure during the catalytic reaction; such stability can be manifested by the retention of the powder X-ray diffraction pattern after the catalytic reaction.

II. Metal-Organic Framework (MOF) Catalysts and their Synthesis

In some embodiments, the presently disclosed subject matter relates to metal-organic framework (MOFs) based on chiral bridging organic bridging ligands. In some embodiments, the MOFs comprise chiral phosphine-, chiral oxazoline-, chiral pyridine-, and/or chiral diene-derived organic bridging linkers. The MOFs can be stable, crystalline and/or porous. The crystalline MOFs can optionally have long-range orders with periodic repeats of metal-based secondary building units (SBUs) and chiral bridging ligands. Thus, in some embodiments, the presently disclosed subject matter relates to crystalline and porous MOFs that comprise periodic repeats of a metal-based SBU and a chiral bridging ligand. In some embodiments, the metal-based SBU comprises a first metal. In some embodiments, the chiral bridging ligand is a chiral phosphine, a chiral oxazoline, a chiral pyridine, and/or a chiral diene.

In some embodiments, the presently disclosed subject matter further relates to the post-synthetic metalation of the MOFs with metal precursors comprising a second metal (such as, but not limited to, Ru and Rh complexes) to afford highly enantioselective catalysts for a broad range of organic transformations. Alternatively, the second metal (e.g., the metal complexes comprising the second metal) can be incorporated into the MOF during or prior to the preparation of the MOF. For example, the second metal can be complexed to the chiral organic bridging unit prior to preparation of the MOF.

In some embodiments the presently disclosed subject matter provides methods for preparing stable, crystalline and/or porous metal-organic frameworks (MOFs) containing chiral phosphine ligands, chiral oxazoline ligands, chiral pyridine ligands, and/or chiral diene ligands. Typical MOF synthesis involves heating a mixture of metal ions or complexes (i.e., a first metal source) and organic bridging ligands or precursors to organic bridging ligands (e.g., chiral organic bridging ligands or their precursors or mixtures of chiral and non-chiral bridging ligands or their precursors) in appropriate solvent mixtures (such as dimethylformamide (DMF), diethylformamide, or others). In some instances, various amounts of acids, such as trifluoroacetic acid (TFA), are added to the reaction mixtures to enhance the crystallinity of the MOF crystals/microcrystals. In some cases, crystal growth modulators such as acetic acid or benzoic acid are added to the reaction mixtures to control the particle sizes of the microcrystals.

In some embodiments, the crystalline MOFs have internal pores, cavities, and open channels to transport organic substrates and products in and out of the MOFs. In some embodiments, the particle sizes of the MOFs can also be tuned to minimize the diffusion distance needed for the organic substrates and products to maximize the catalytic turnover frequency and total catalytic turnover number. For example, in some embodiments, the MOF can be prepared by contacting a chiral bridging ligand and a first metal source in a solvent or mixture of solvents selected based on solvent molecule size, such that the sizes and/or shapes of internal pores, cavities and/or open channels in the MOF can be tailored to enhance catalytic activity and/or selectivity. In some embodiments, the solvent comprises DMF.

In some embodiments, the MOFs can contain a mixture of two or more different organic bridging ligands. In some embodiments, one of the organic bridging ligands in such a "mixed" MOF can be a chiral phosphine-, chiral oxazoline-, chiral pyridine- or chiral diene-derived ligand, while the other bridging ligand can be non-chiral. In some embodiments, the "mixed" MOFs can be prepared to increase the channel size of the MOF and/or to maximize the efficiency of chiral ligand usage.

In some embodiments, the SBU can be selected from the group comprising Zr-oxo clusters, Hf-oxo clusters, Zn-oxo clusters, Ti-oxo clusters, Cu-carboxylate paddlewheels, and other secondary building units that have been used to construct MOFs. In some embodiments, the first metal source, i.e., the source of the metal of the SBU is a metal alkoxide or a metal halide. In some embodiments, the first metal source is zirconium tetrachloride ($ZrCl_4$) or hafnium tetrachloride ($HfCl_4$).

In addition to comprising a chiral phosphine, a chiral oxazoline, a chiral pyridine, or chiral diene group (i.e., that can bind to a second metal, such as Fe, Co, Ni, Rh, Ru, Ir, Os, Pt, or Pd), the organic bridging ligand also includes chemical moieties that can bond (e.g., coordinatively bond) to the metal containing SBUs. Thus, in some embodiments, the chiral bridging ligand is substituted (or derivatized) with one or more groups that include a moiety, such as, but not limited to, a carboxylate or carboxylic acid, an ester, an amide, a pyridine or other nitrogen containing aromatic group, an amine (including nitrogen-containing heterocycles), a hydroxyl, a thiol, a thioalkyl, —$B(OH)_2$, —$SO_3H$, —$PO_3H$, —$NO_2$, or a phosphonate. In some embodiments, the chiral bridging ligand is substituted with one or more groups selected from a carboxylate, a pyridine or a phosphonate. In some embodiments, the chiral bridging ligand is a dicarboxylate, a tricarboxylate, a tetracarboxylate, a bipyridine, a tripyridine, a tetrapyridine, a diphosphonate, a triphosphonate, or a tetraphosphonate.

In some embodiments the presently disclosed subject matter provides chiral phosphine-based MOFs. Some examples of chiral phosphines that can be modified and used to construct MOFs are shown below in Scheme 1.

Scheme 1. Examples of chiral phosphines that can be modified and used to build MOFs.
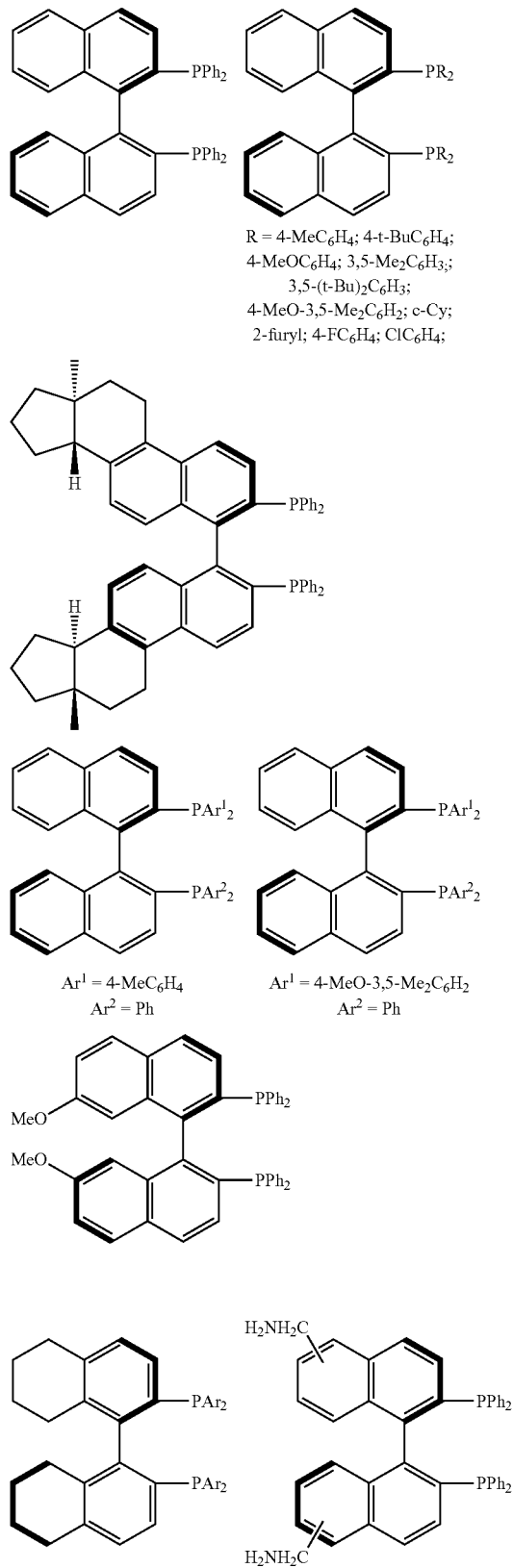
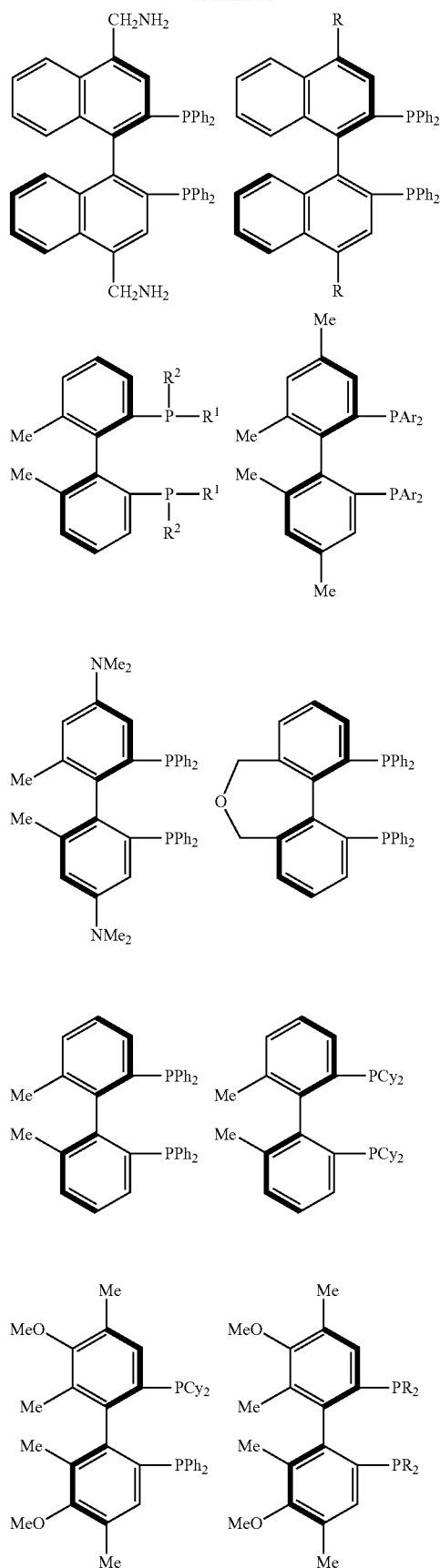

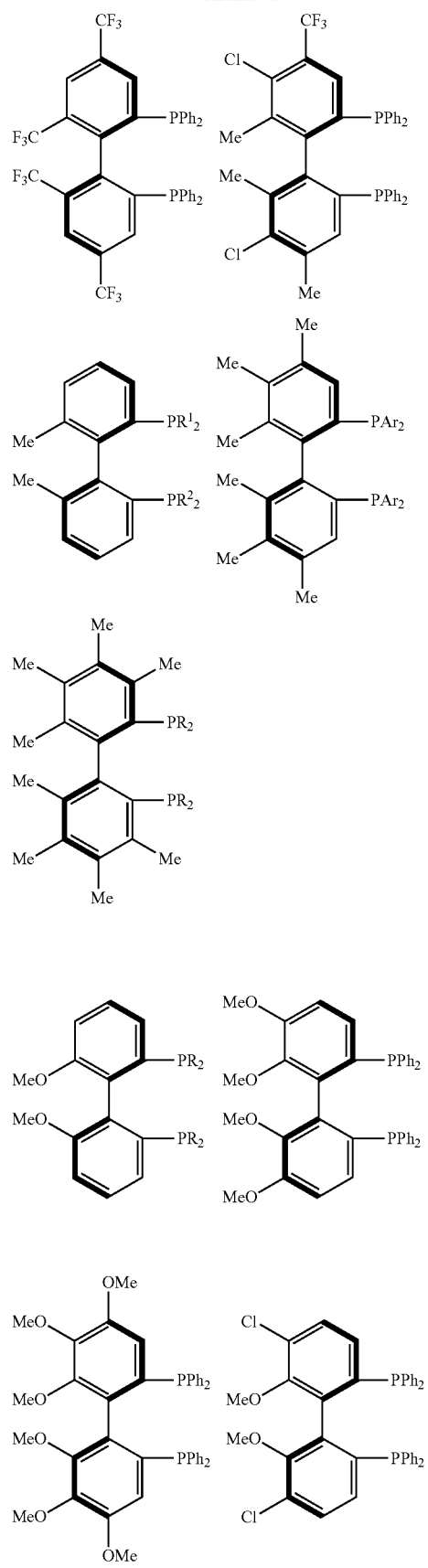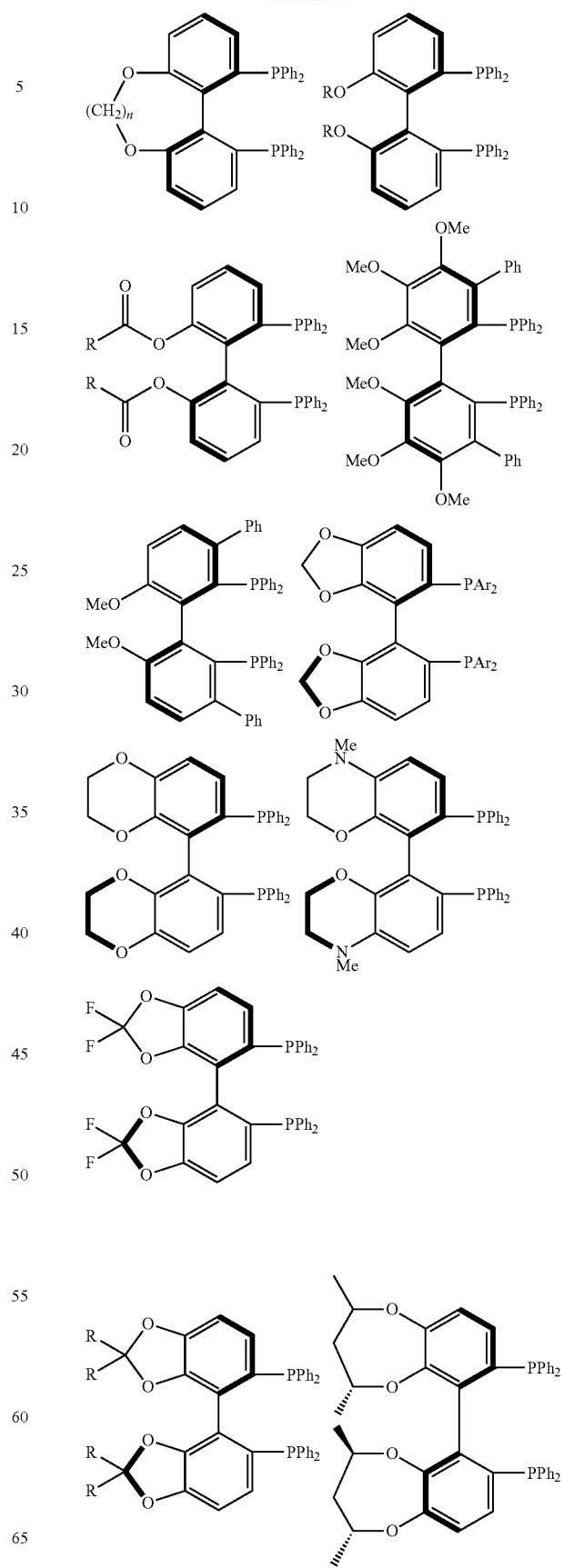

-continued
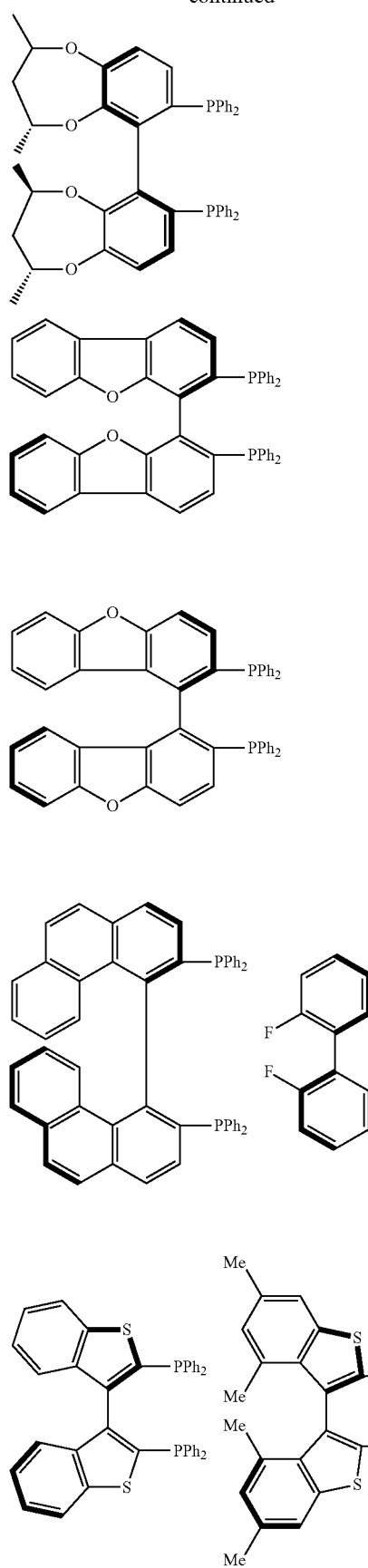
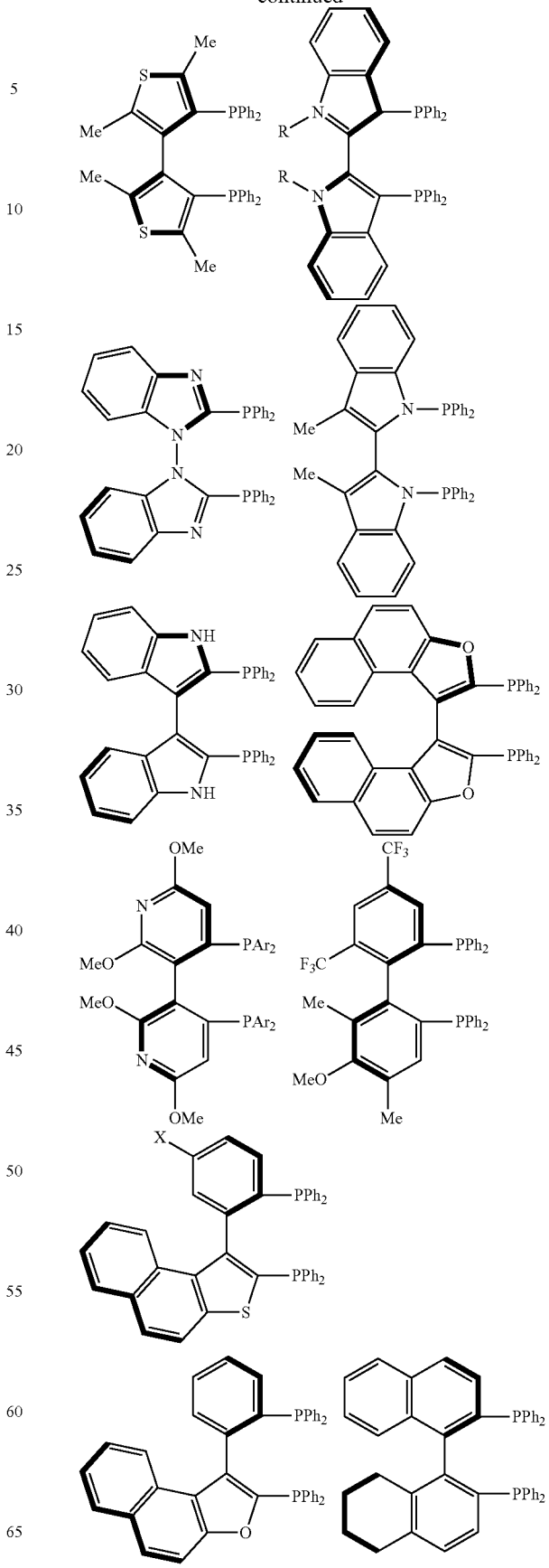

-continued
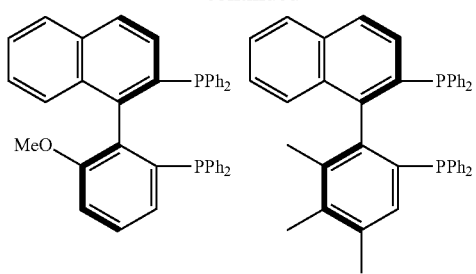
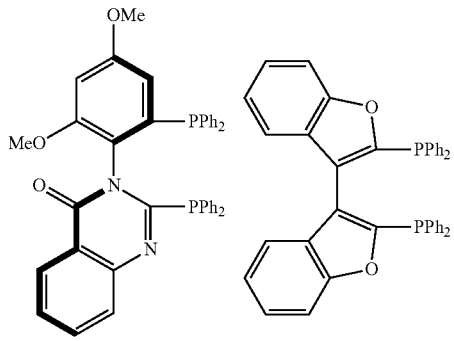
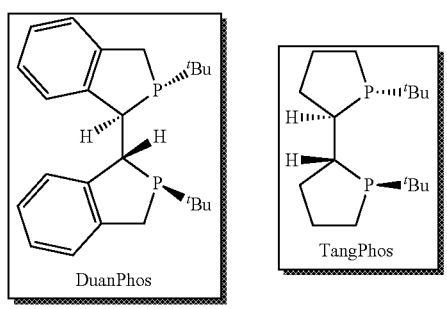
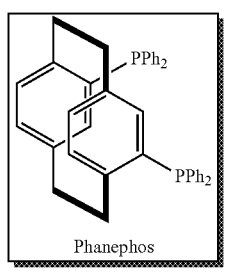
Phanephos
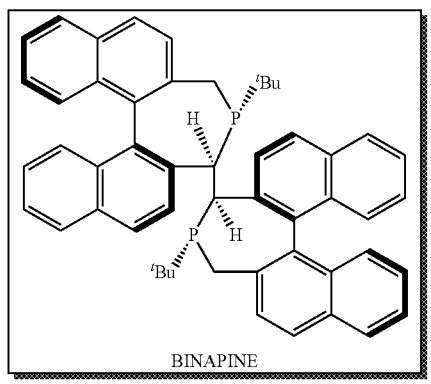
BINAPINE
-continued
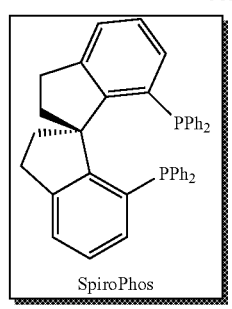
SpiroPhos
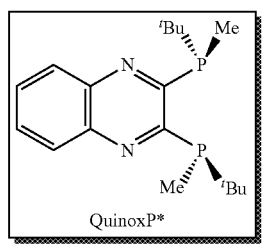
QuinoxP*
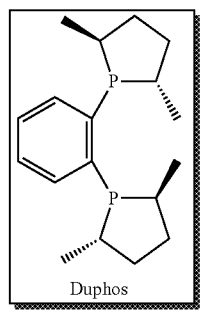
Duphos
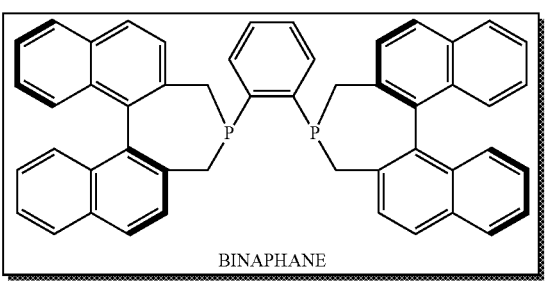
BINAPHANE
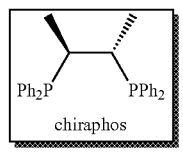
chiraphos
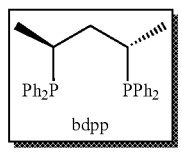
bdpp
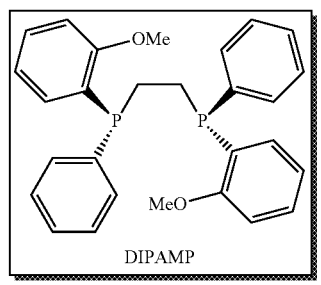
DIPAMP
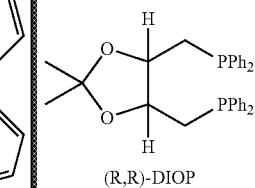
(R,R)-DIOP
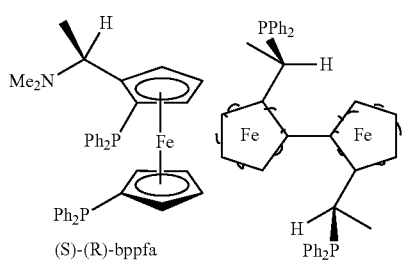
(S)-(R)-bppfa

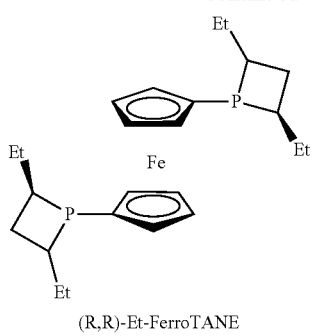

(R,R)-Et-FerroTANE

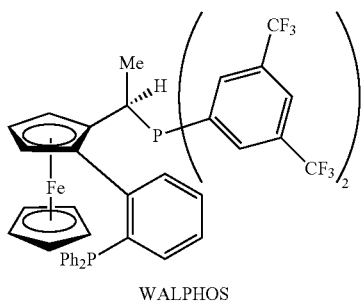

WALPHOS

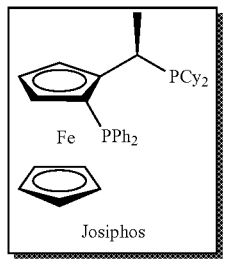

Josiphos

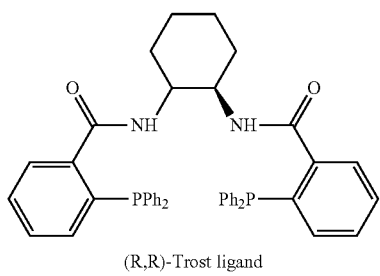

(R,R)-Trost ligand

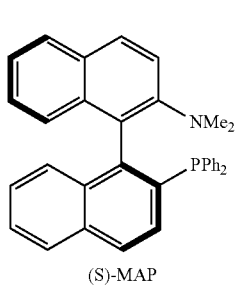

(S)-MAP

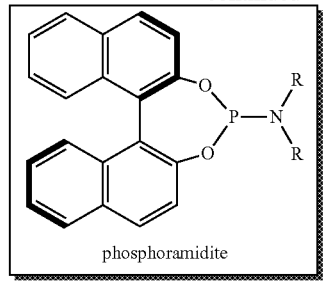

phosphoramidite

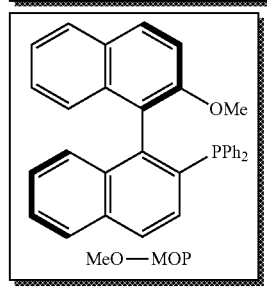

MeO—MOP

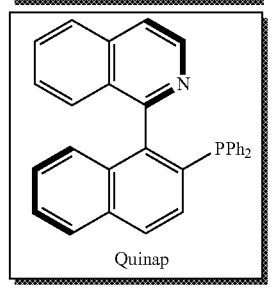

Quinap

In some embodiments, the bridging ligands that contain chiral phosphines can be dicarboxylate, tricarboxylate, tetracarboxylate, bipyridine, tripyridine, tetrapyridine, diphosphonate, triphosphonate, tetraphosphonate, or mixed ligands based on common coordinating groups. In some embodiments, the representative chiral phosphines listed in Scheme 1 can be employed by being derivatized with one or more substituents that include a carboxylate, pyridine, phosphonate or other metal chelating group that can bond to the SBU. In some embodiments, metal complexes of chiral phosphine binding ligand can be first prepared and then contacted with a metal source to synthesize MOF catalysts. In some embodiments, the chiral phosphine bridging ligand is first used to synthesize a MOF (by being contacted with a first metal source) and then metalated (with a second metal) to prepare the MOF catalysts. In either case, during MOF synthesis, solvents of various sizes can also be used to modulate the sizes and shapes of internal pores, cavities, and open channels to enhance catalytic activity and selectivity.

In some embodiments, the chiral bridging ligand is a chiral phosphine (e.g., based on one of the phosphines of Scheme 1) comprising at least two substituents selected from the group comprising carboxylate, pyridine, and phosphonate. In some embodiments, the chiral bridging ligand is a dicarboxylate-substituted chiral bisphosphine. For example, in some embodiments, the chiral bridging ligand comprises a 2,2-bis(diphenylphosphino)-1,2'-binaphthyl (BINAP) derivative with two carboxylate substituents, e.g., a BINAP derivative with 4,4' substituents comprising carboxylate groups.

Figure 2:
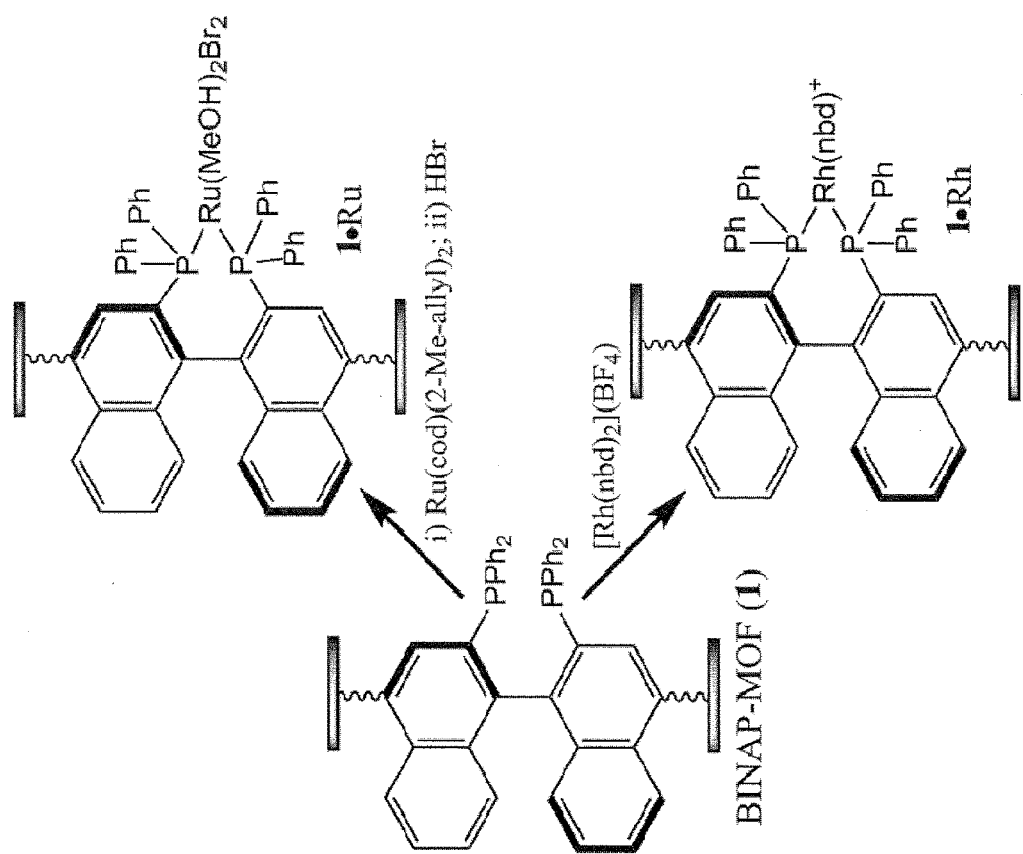
FIG. 2 is a schematic drawing showing the metal-organic framework described for FIG. 1, also referred to as BINAP-MOF, MOF 1, or 1, metalated with ruthenium (Ru) or rhodium (Rh).
Figure 12:
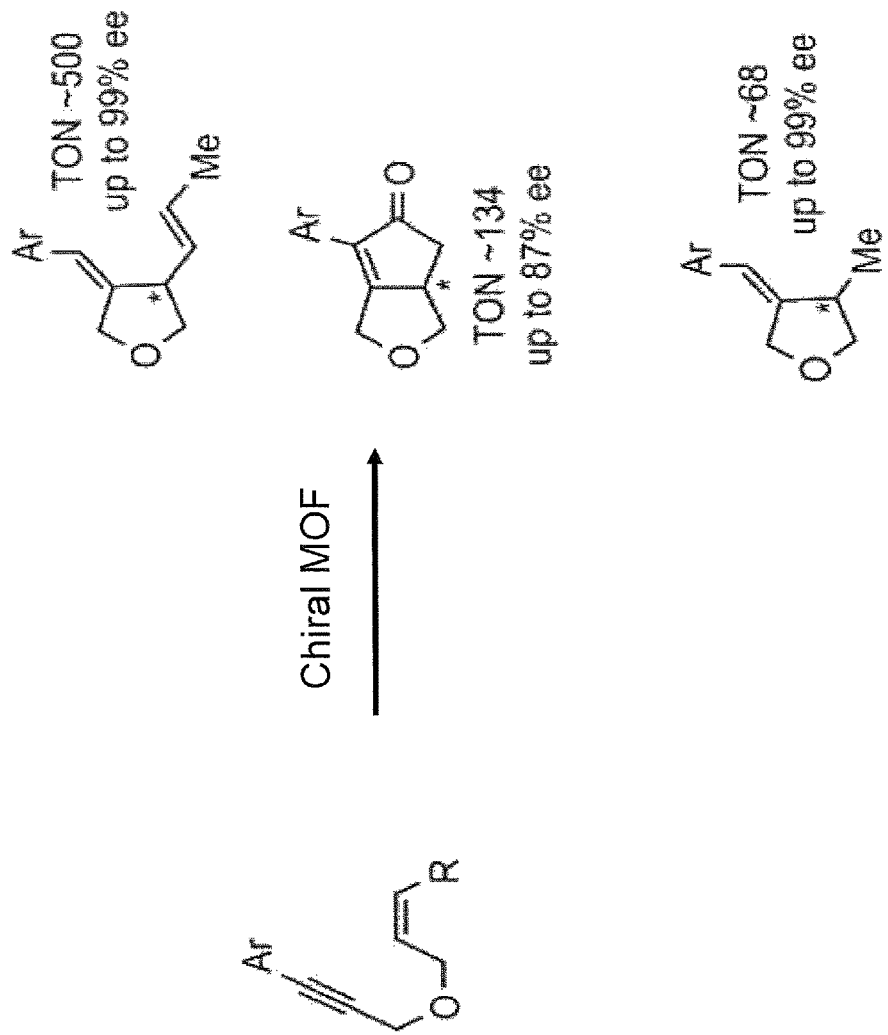
FIG. 12 is schematic drawing summarizing some cyclization related catalytic activities of chiral phosphine-based metal-organic framework (MOF) catalysts of the presently disclosed subject matter.

In some embodiments, the chiral MOF is based on a BINAP-derived dicarboxylate linker (H₂L), i.e., 4,4'-bis(4- carboxyphenylethynyl)BINAP, and is called BINAP-MOF or MOF 1. The BINAP-MOF can be postsynthetically metalated (see FIG. 2) to afford highly enantioselective catalysts for various reactions, such as, but not limited to, the hydrogenation of substituted alkenes and carbonyl compounds and for addition reactions to α,β-unsaturated ketones (See FIG. 1) or for various cyclization reactions. See FIGS. 6, 7, and 12. BINAP-MOF contains the $Zr_6O_4(OH)_4(O_2CR)_{12}$ cluster secondary building unit (SBU) and adopts the same framework topology as UiO-66 that was previously reported by Lillerud and coworkers. See Cavka et al., J. Am. Chem. Soc., 2008, 130, 13850; and Kandiah et al., Chem. Mater., 2010, 22, 6632. The UiO structure can provide an ideal platform to design MOF-based heterogeneous catalysts due to their stability under a range of reaction conditions.

As described further hereinbelow in Examples 2-5, the BINAP-derived dicarboxylic acid bridging ligand, $H_2L$, can be prepared from 4,4'-$I_2$-BINAP (see Hu et al., Amgew. Chem., Int., Ed., 2004, 43, 2501) in a multi-step sequence as shown in Scheme 2. 4,4'-$I_2$-BINAP was oxidized with hydrogen peroxide and coupled with methyl-4-ethynylbenzoate via a Pd-catalyzed Sonogashira reaction to yield 4,4'-bis(methyl-4-carboxyphenylethynyl)-BINAP oxide. Reduction of the BINAP oxide following by saponification led to $H_2L$ in a 40% overall yield. Due to the air-sensitive nature of the phosphine, solvothermal crystal growths of BINAP-MOF were carried out in an air-free environment. As further described in Example 6 below, a mixture of equimolar $H_2L$ and $ZrCl_4$ in dimethylformamide (DMF) and a small amount of trifluoroacetic acid can be degassed in a glass tube, flame-sealed under vacuum, and heated at 120° C. for 3 days, to yield the BINAP-MOF(1) as colorless octahedral crystals in 44% yield.

Scheme 2. Synthesis of $H_2L$ starting from 4,4'-$I_2$-BINAP.

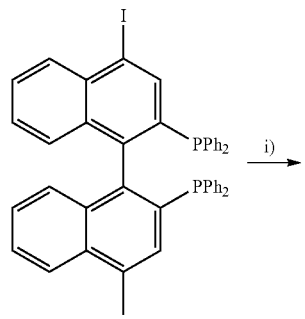

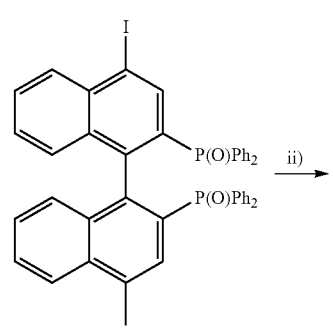

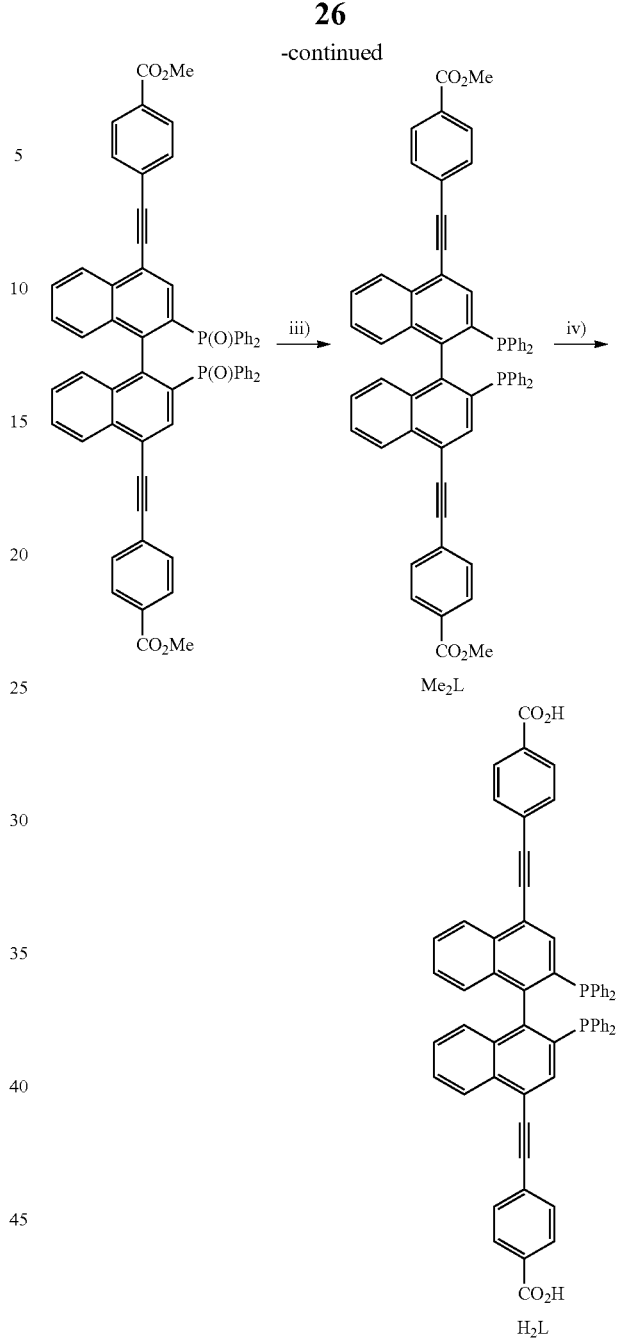

i) $H_2O_2$, acetone, 85% yield; ii) Pd(PPh$_3$)$_4$, CuI, PPh$_3$, methyl-4-ethylnylbenzoate, THF/TEA, 65% yield; iii) HSiCl$_3$, TEA, m-xylene, 76% yield; iv) NaOH, THF, EtOH, 95% yield.

Mixed ligands of achiral and chiral ligands can be used to increase the efficiency and reduce the amount of the chiral ligands used. Any suitable non-chiral organic bridging ligand can be used. The non-chiral organic bridging ligand can typically comprise at least one chemical moiety that can coordinate to the first metal of the SBU. Thus, in some embodiments, the non-chiral organic bridging ligand comprises at least one carboxylate, pyridine, or phosphonate moiety. In some embodiments, the non-chiral organic bridging ligand is selected from a dicarboxylate, a tricarboxylate, a tetracarboxylate, a bipyridine, a tripyridine, a tetrapyridine, a diphosphonate, a triphosphonate, and a tetraphosphonate. In some embodiments, the non-chiral organic bridging ligand comprises two carboxylate, pyridine or phosphonated moieties. In some embodiments, the non-chiral organic bridging ligand comprises one or more arylene groups. The identity or number of arylene groups can be tailored based upon the desired length of the non-chiral bridging unit. In some embodiments, the non-chiral organic bridging ligand can comprise a nitro-substituted arylene group.

Figure 9A:
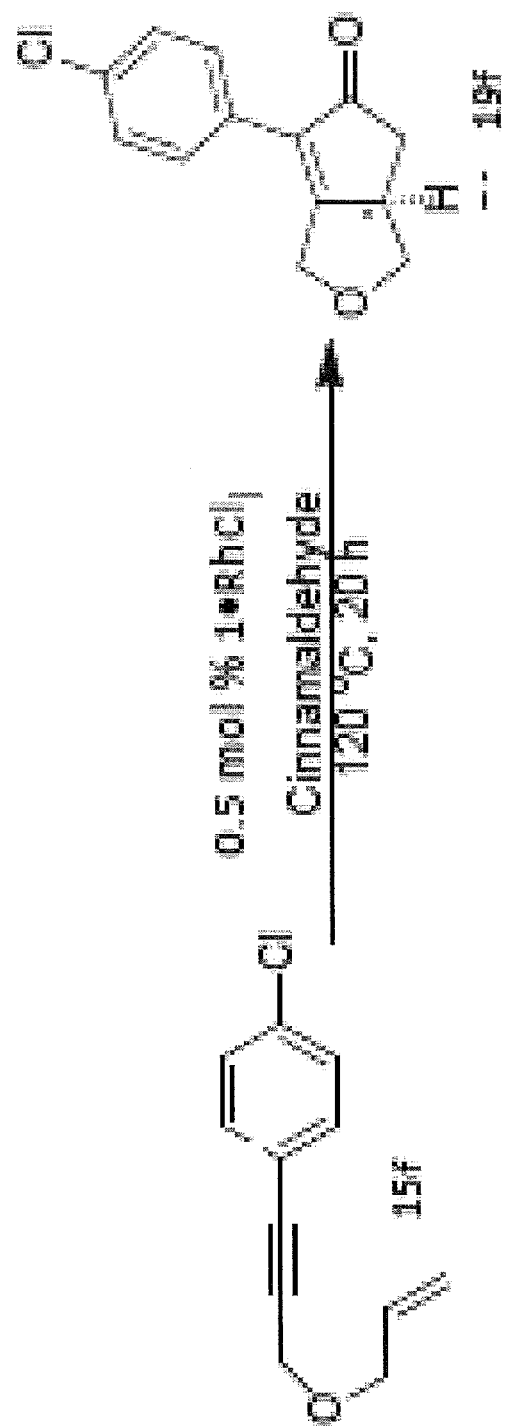
FIG. 9A is a schematic drawing showing the use of a metal-organic framework containing a (2,2'-bis(diphenylphosphino)-1,1-binaphthyl) (BINAP)-based organic bridging ligand and zirconium oxoclusters (i.e., MOF 1) in an intermolecular Pauson-Khand type reaction of 1,6 enyne 15f.
Figure 9B:
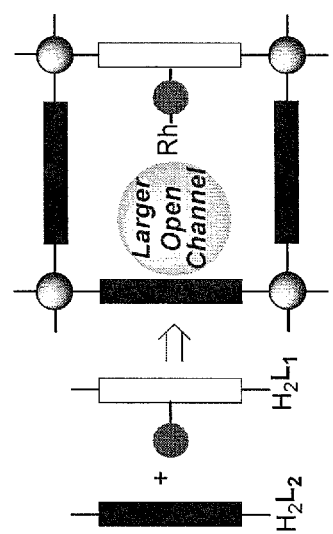
FIG. 9B is a schematic drawing showing how the use of mixed organic bridging ligands, including both a chiral ligand $H_2L_1$ that can be metalated and a non-chiral bridging ligand, $H_2L_2$, can result in metal-organic frameworks having larger open channels.
Figure 10:
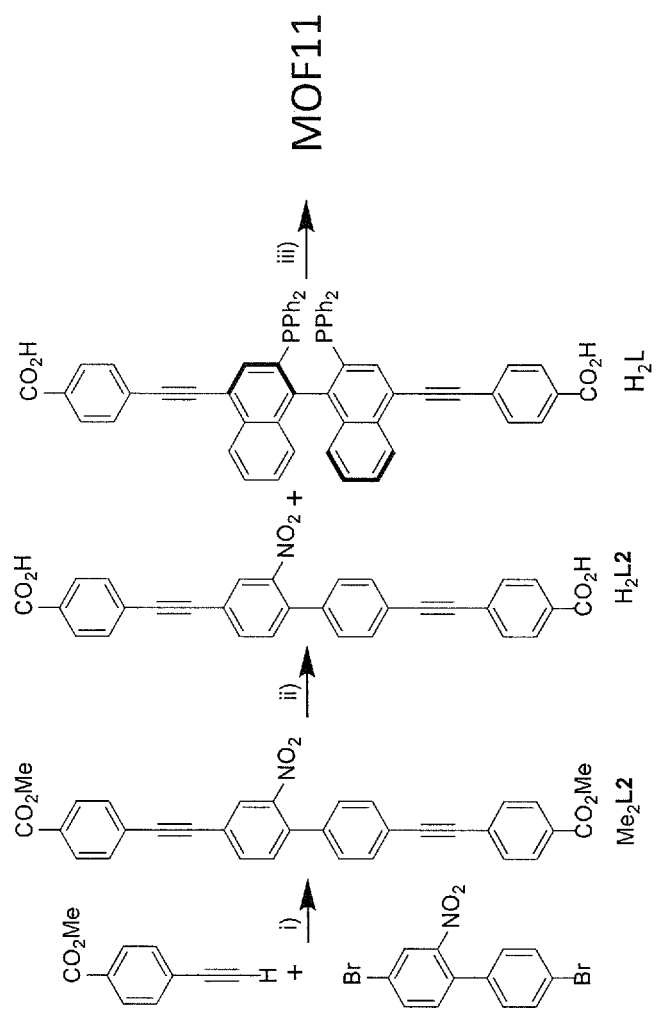
FIG. 10 is a schematic drawing of a synthetic route to a mixed ligand metal-organic framework (MOF) containing zirconium-oxo custers and both a (2,2'-bis(diphenylphosphino)-1,1-binaphthyl) (BINAP)-based organic bridging ligand and a nonchiral nitro-group containing organic bridging ligand (i.e., MOF 11). Reagents: (i) $Pd(PPh_3)_4$, CuI, $PPh_3$, TEA, THF, 75° C., 63% yield; (ii) NaOH, THF, EtOH, $H_2O$, 70° C., 71% yield; (iii) $H_2L$, $ZrCl_4$, TFA, DMF, 100° C., 71% yield.

FIG. 10 shows an exemplary synthesis of a mixed ligand MOF comprising both a chiral phosphine-based bridging ligand, i.e., H$_2$L, prepared as shown in Scheme 2 above, and a non-chiral ligand, such as H$_2$L$_2$ as shown in Scheme 12 and H$_2$QPDC as shown in Scheme 13. In some embodiments, the use of mixed ligands can increase the pore size of the MOFs. See FIG. 9B.

The ratio of chiral and non-chiral ligand used to prepare a mixed ligand MOF can be any desirable ratio. In some embodiments, the molar ratio can range from 9:1 non-chiral ligand:chiral ligand to 1:9 non-chiral ligand:chiral ligand. In some embodiments, it can be economically advantageous to use a greater amount of non-chiral ligand. In some embodiments, the ratio of non-chiral:chiral ligand can be between 9:1 to about 2:1 (e.g., about 9:1, about 8:1, about 7:1, about 6:1, about 5:1, about 4:1, about 3:1, or about 2:1).

In some embodiments, the MOF comprising the chiral phosphine organic bridging ligand and the first metal is prepared and then contacted with a second metal source to metalate the phosphine. The second metal source can comprise, for example, Fe, Co, Ni, Rh, Ru, Ir, Os, Pt or Pd. In some embodiments, the second metal source comprises Ru or Rh. In some embodiments, the second metal source is Ru(cod)(2-Me-allyl)$_2$ or Rh(nbd)$_2$BF$_4$.

In some embodiments the presently disclosed subject matter provides chiral diene-based MOFs. Some examples of chiral dienes that can be used in the design of organic bridging ligands for MOFs of the presently disclosed subject matter include, but are not limited to, cyclohexadiene, cyclooctadiene, bicyclo[2.2.1]hepta-2,5-diene (norbornadiene), bicyclo[2.2.2]octa-2,5-diene, bicyclo[3.3.1]nona-2,6-diene, and bicyclo[3.3.2]decadiene. Such diene cores can be substituted by various substituents, including, but not limited to alkyl, aralkyl, aryl and alkoxy groups to provide chiral moieties and further derivatized to include at least one or more groups for bonding to the MOF SBUs, such as, but not limited to, carboxylate, pyridine, and/or phosphonate. Thus, in some embodiments, the bridging ligands that contain chiral dienes can be dicarboxylate, tricarboxylate, tetracarboxylate, bipyridine, tripyridine, tetrapyridine, diphosphonate, triphosphonate, tetraphosphonate, or mixed ligands based on a chiral diene.

Mixed MOFs of chiral diene ligands and non-chiral ligands can be used to increase the efficiency and reduce the amount of the chiral ligands used. In some embodiments, metal complexes of chiral diene can be first prepared and then used to synthesize MOF catalysts (e.g., by reaction of the metal complex of the chiral diene with a further metal-containing compound). In some embodiments, the chiral diene bridging ligand is first used to synthesize a MOF (by being contacted with a first metal source) and then metalated (with a second metal) to prepare the MOF catalysts. During MOF synthesis, solvents of various sizes can also be used to modulate the sizes and shapes of internal pores, cavities, and open channels to enhance catalytic activity and selectivity.

Accordingly, in some embodiments, the presently disclosed subject matter provides a method of making a crystalline and porous MOF comprising periodic repeats of a metal based SBU and a chiral diene bridging unit, wherein the method comprises providing the chiral diene and contacting the chiral diene with a first metal source to obtain a crystalline and porous MOF. The chiral diene can be substituted with one or more carboxylate, pyridine and/or phosphate moieties. In some embodiments, the chiral diene is substituted with at least two carboxylate, pyridine or phosphate moieties. In some embodiments, the bridging ligands that contain chiral dienes can be dicarboxylate, tricarboxylate, tetracarboxylate, bipyridine, tripyridine, tetrapyridine, diphosphonate, triphosphonate, tetraphosphonate, or mixed ligands based on a chiral diene.

Figure 13:
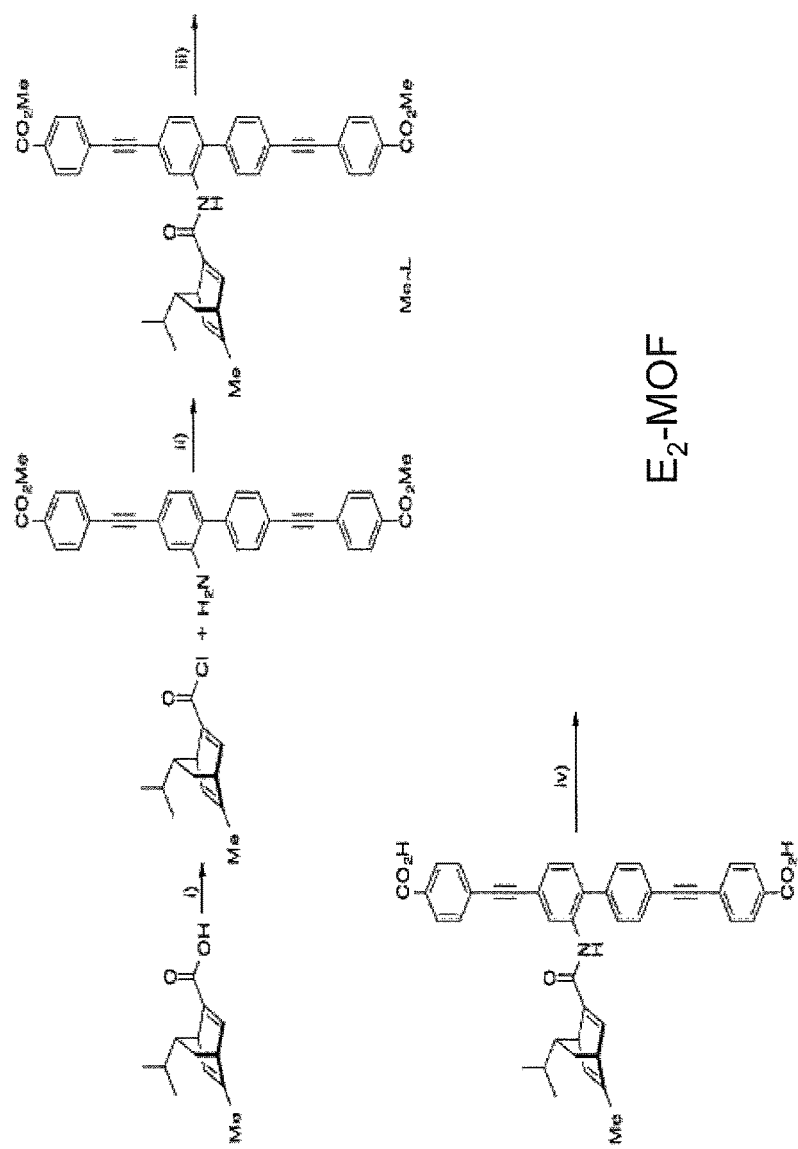
FIG. 13 is a schematic drawing showing the synthesis of a metal-organic framework (MOF) of the presently disclosed subject matter that comprises a chiral diene-based organic bridging ligand, i.e., $E_2$-MOF. Reagents: i) oxalyl chloride, $CH_2Cl_2$; ii) TEA, THF, 57% yield over 2 steps; iii) NaOH, THF, EtOH, 77% yield; iv) $ZrCl_4$, TFA, DMF, 70° C., 5 d, 42% yield.

In some embodiments, the chiral diene is a chiral bicyclo [2.2.2]octa-2,5-diene. In some embodiments, the chiral bridging ligand is 4,4'-((2-((1R,4R,7R)-7-isopropyl-5-methylbicyclo[2.2.2]octa-2,5-diene-2-carboxamido)-[1,1'-biphenyl]-4,4'-diyl)bis(ethyne-2,1-diyl)dibenzoic acid or a stereoisomer thereof. FIG. 13 shows the synthesis of an exemplary MOF comprising a chiral diene-based bridging ligand.

In some embodiments, the MOF comprising the chiral diene bridging ligand can further comprise a non-chiral bridging ligand, such as those described hereinabove with regard to the chiral phosphine MOFs. The ratio of chiral and non-chiral ligand used to prepare a mixed ligand MOF can be any desirable ratio. In some embodiments, the molar ratio can range from 9:1 non-chiral ligand:chiral ligand to 1:9 non-chiral ligand:chiral ligand. In some embodiments, it can be economically advantageous to use a greater amount of non-chiral ligand. In some embodiments, the ratio of non-chiral:chiral ligand can be between 9:1 to about 2:1 (e.g., about 9:1, about 8:1, about 7:1, about 6:1, about 5:1, about 4:1, about 3:1, or about 2:1).

In some embodiments, the MOF comprising the chiral diene organic bridging ligand and the first metal is prepared and then contacted with a second metal source to metalate the diene. The second metal source can comprise, for example, Fe, Co, Ni, Rh, Ru, Ir, Os, Pt or Pd. In some embodiments, the second metal source comprises Ru or Rh. In some embodiments, the second metal source is [RhCl(C$_2$H$_4$)$_2$]$_2$ or Rh(acac)(C$_2$H$_4$)$_2$.

In some embodiments, the chiral ligand is a chiral pyridine or a chiral oxazoline. Some examples of chiral pyridines and chiral oxazolines that can be modified and used to construct MOFs of the presently disclosed subject matter are shown below in Schemes 3 and 4.

Scheme 3. Examples of chiral pyridines that can be modified and used to build MOFs.

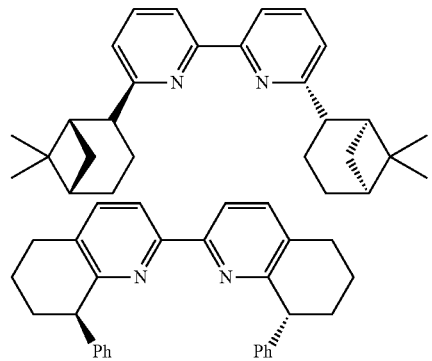

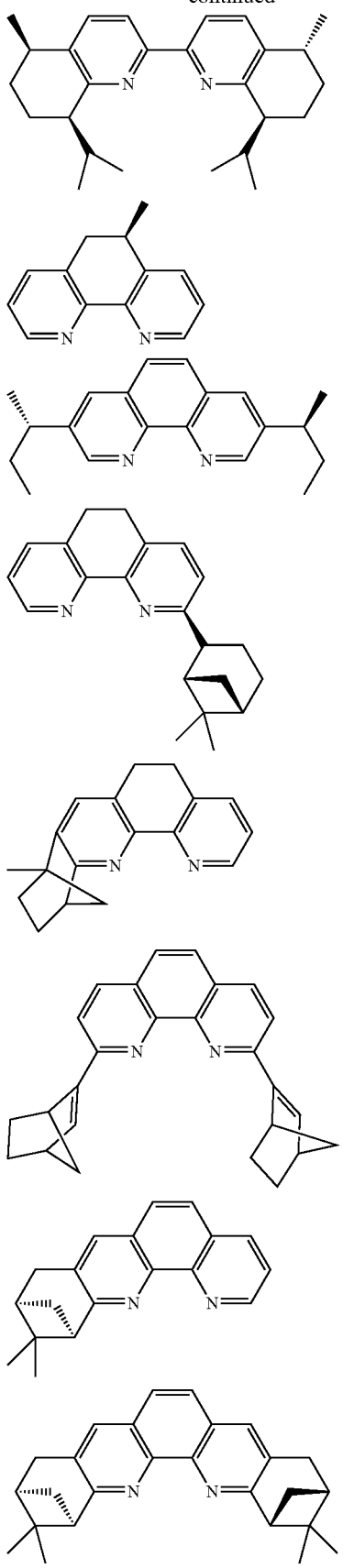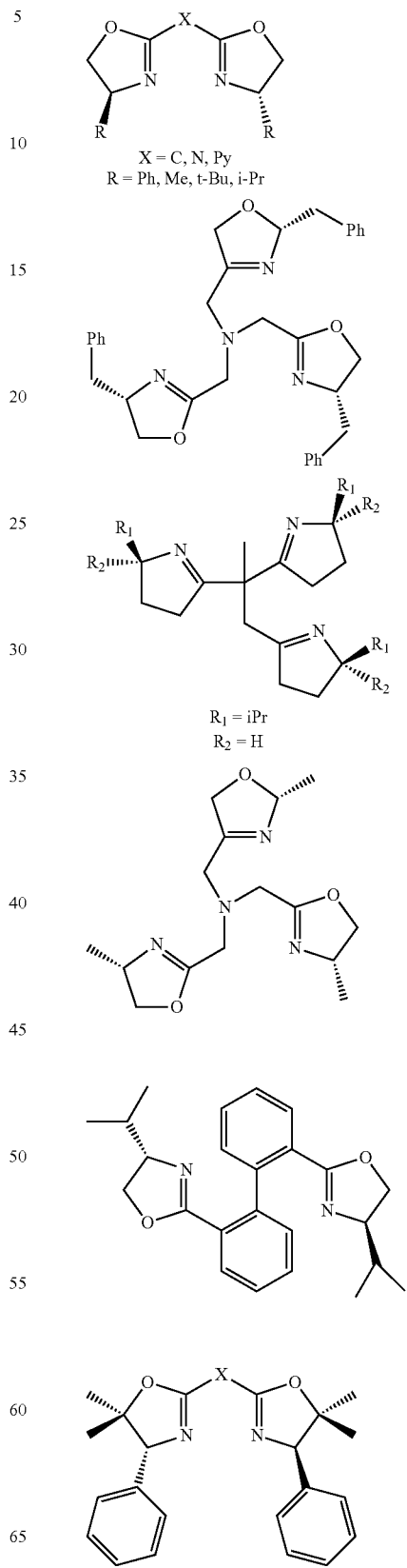
Scheme 4. Examples of chiral oxazolines that can be modified and used to build MOFs.

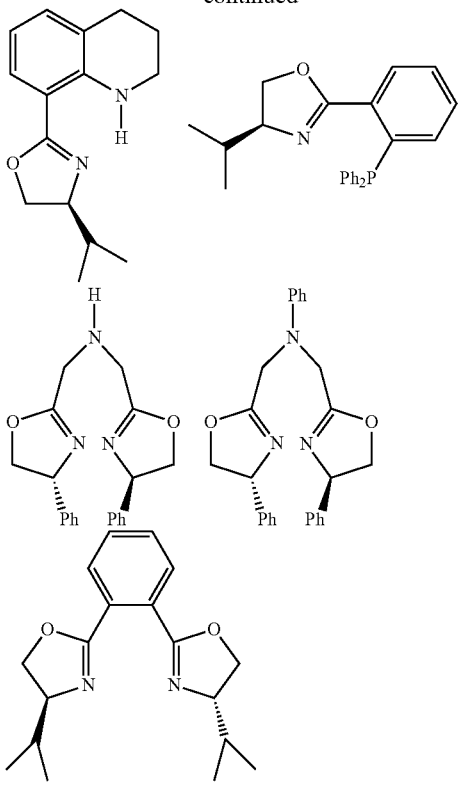

In some embodiments the chiral bridging ligand is not a derivative of a chiral N, N'-alkylenebis(salicylimine), a chiral N,N'-arylenebis(salicylimine), or a chiral 1,1'-bi-2-napthol (BINOL).

In some embodiments, the presently disclosed subject matter provides an asymmetric heterogeneous catalyst comprising a crystalline and porous MOF, wherein the MOF comprises periodic repeats of a metal-based SBU, wherein the SBU comprises a first metal, and a chiral bridging ligand, wherein the chiral bridging unit comprises a chiral phosphine, a chiral oxazoline, a chiral pyridine, and/or a chiral diene, and wherein the chiral bridging ligand is complexed to a second metal. In some embodiments, the first metal is selected from the group comprising Zr, Zn, Ti, and Cu. In some embodiments, the second metal is selected from the group comprising Fe, Co, Ni, Rh, Ru, Ir, Os, Pt or Pd. In some embodiments, the second metal is Rh or Ru. In some embodiments, the catalyst further comprises a non-chiral organic bridging ligand.

III. Catalytic Reactions

In some embodiments the presently disclosed subject matter provides uses of presently disclosed MOF-based catalysts, such as but not limited to, as catalysts for one or more of the asymmetric catalytic reactions shown in Scheme 5, below, or other related reactions in a batch mode, in conventional solvents, or in the absence of solvents, or in unconventional solvents, such as supercritical carbon dioxide. In some embodiments the presently disclosed subject matter provides uses of thus obtained chiral MOFs for asymmetric catalytic reactions shown in Scheme 5 or other related reactions in a flow reactor or a supercritical fluid reactor to enable green manufacturing of fine chemicals. In some embodiments the presently disclosed subject matter provides for the use of chiral MOFs to catalyze sequential or multistep reactions. In some embodiments the presently disclosed subject matter provides for the use of multiple chiral MOFs in the same system to catalyze sequential or multistep reactions.

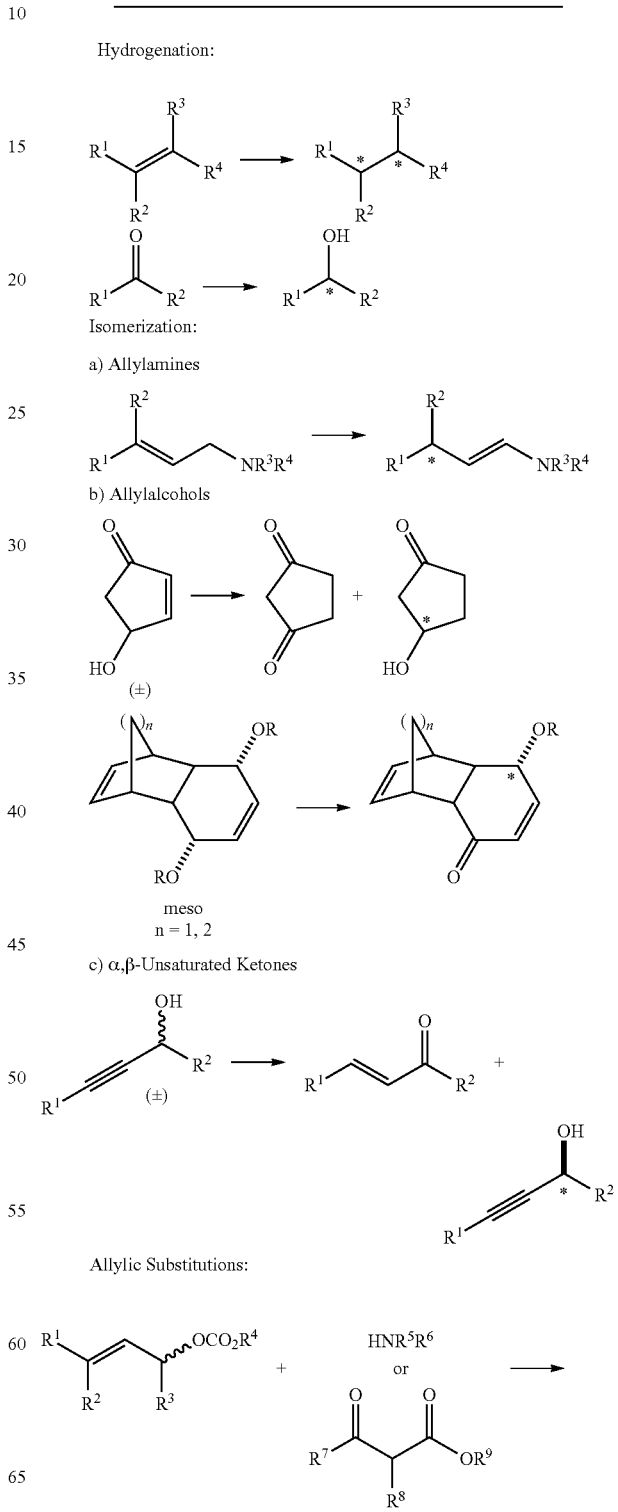

33

-continued

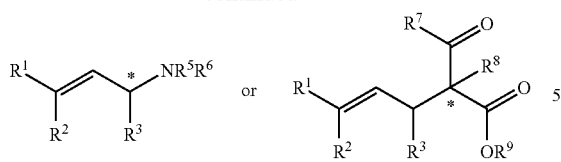

Coupling Reactions:

a) Buchwald-Hartwig Amination

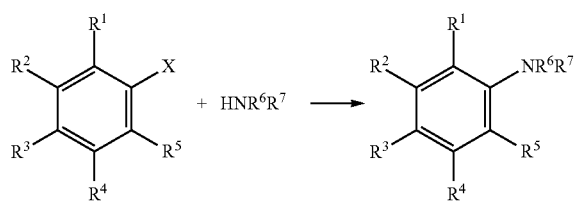

X = Br, OTf b) Heck Reaction

1) Intramolecular Reactions

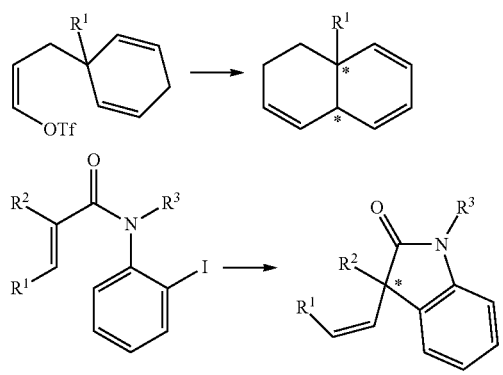

2) Intermolecular Reactions

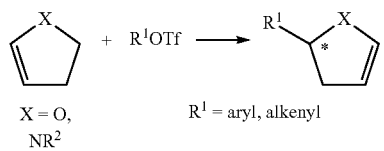

X = O, NR$^2$    R$^1$ = aryl, alkenyl

Conjugated Additions:

a) Michael Reaction

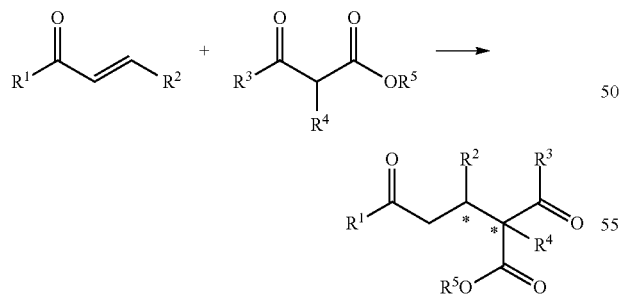

b) Aza-Michael Reaction

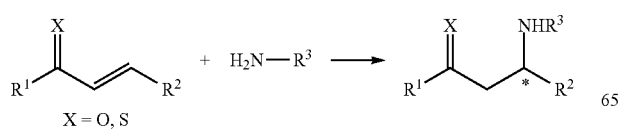

X = O, S

34

-continued c) Other Kinds of Conjugated Additions

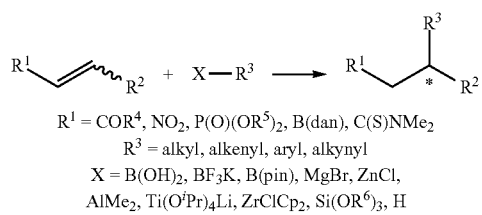

R$^1$ = COR$^4$, NO$_2$, P(O)(OR$^5$)$_2$, B(dan), C(S)NMe$_2$
R$^3$ = alkyl, alkenyl, aryl, alkynyl
X = B(OH)$_2$, BF$_3$K, B(pin), MgBr, ZnCl, AlMe$_2$, Ti(O$^i$Pr)$_4$Li, ZrClCp$_2$, Si(OR$^6$)$_3$, H Aldol Reactions:

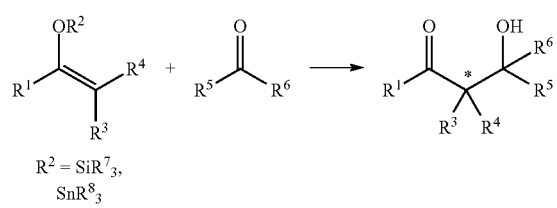

R$^2$ = SiR$^7{}_3$, SnR$^8{}_3$

Mannich-Type Reactions:

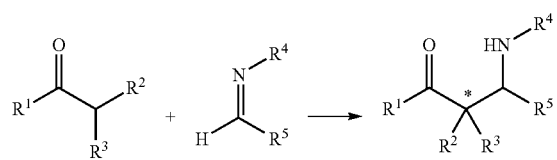

R$^2$ = CO$_2$R$^6$, CN

Nucleophilic Additions to Carbonyl and Imine Compounds:

a) Cyanation

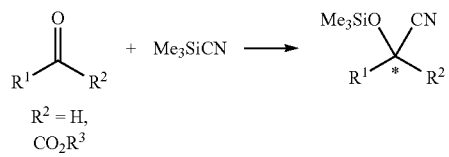

R$^2$ = H, CO$_2$R$^3$ b) Propargylation

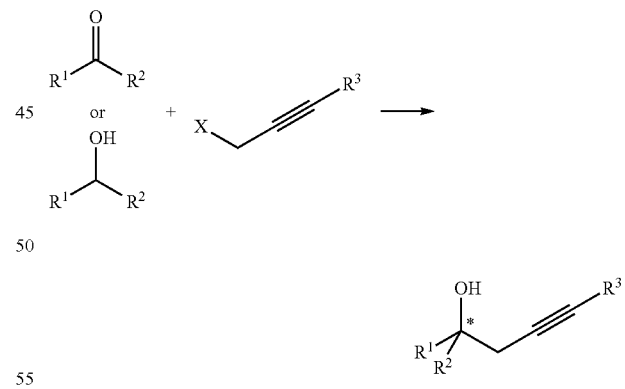

c) Allylation

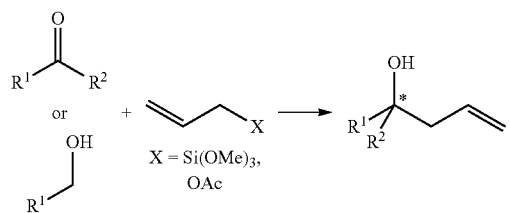

X = Si(OMe)$_3$, OAc

-continued
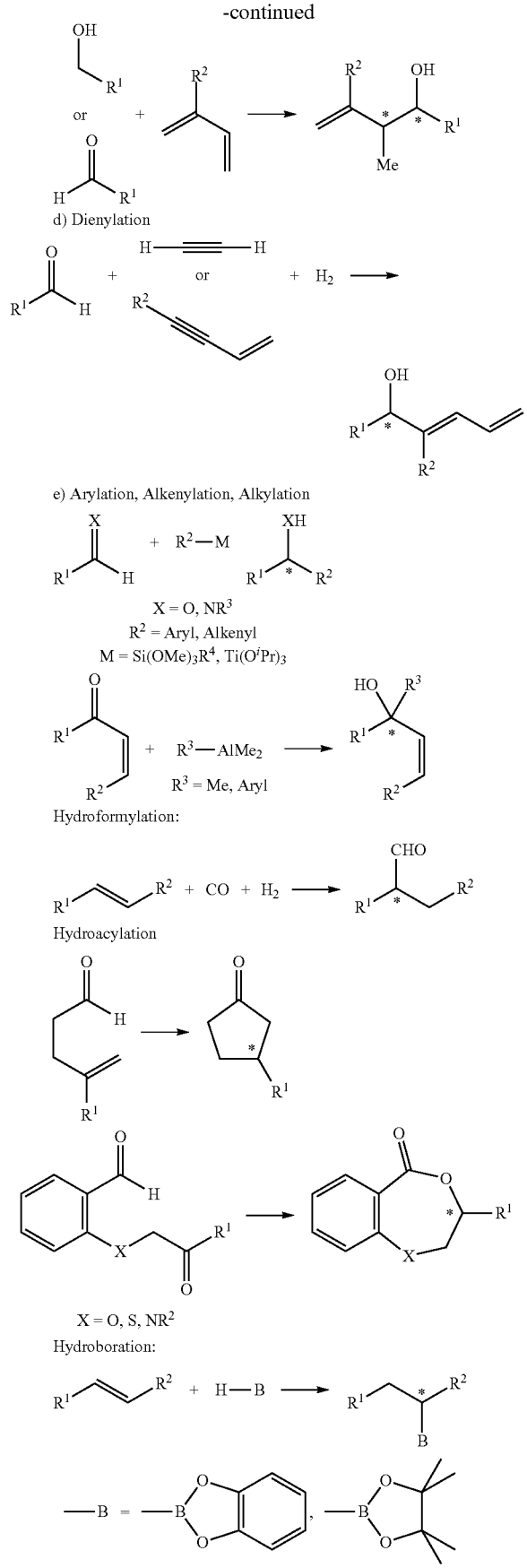
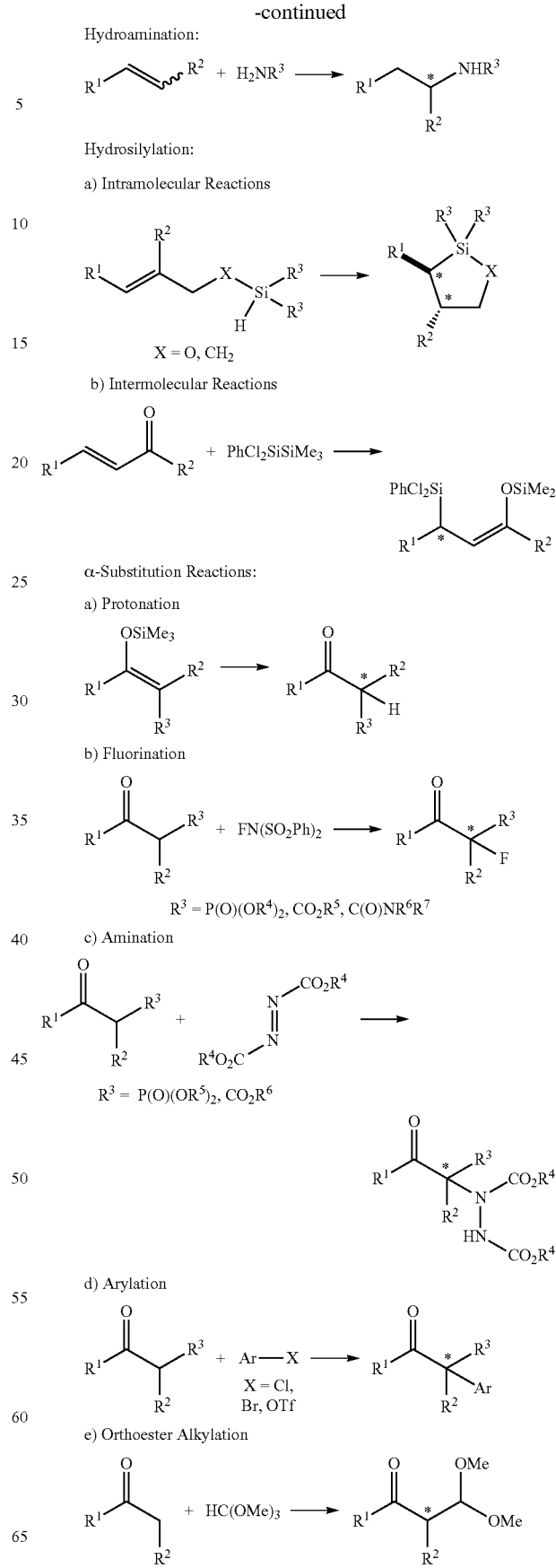

Ene Reaction:

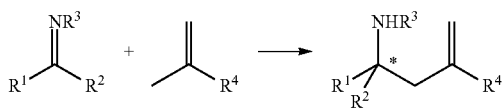

Diels-Alder Reactions:

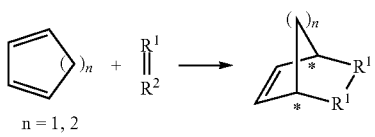

n = 1, 2

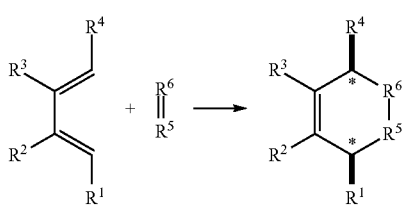

Pauson-Khand Reaction:

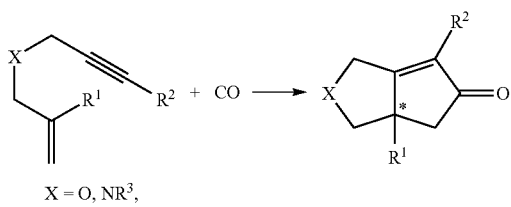

X = O, NR$^3$,
C(CO$_2$R$_4$)$_2$

Intramolecular Cyclization of Enynes:

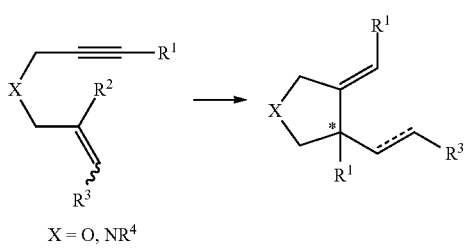

X = O, NR$^4$

[2 + 2 + 2] Cycloaddition

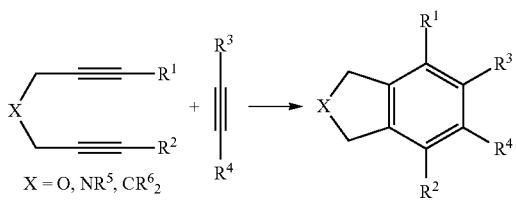

X = O, NR$^5$, CR$^6_2$

[3 + 2] Cycloaddition

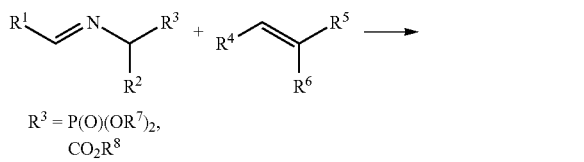

R$^3$ = P(O)(OR$^7$)$_2$,
CO$_2$R$^8$

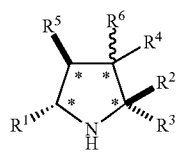

Ring-Opening Reactions:

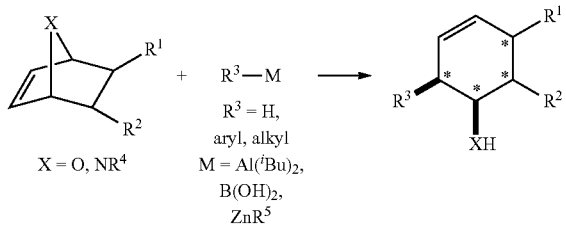

X = O, NR$^4$

R$^3$ = H, aryl, alkyl

M = Al($^i$Bu)$_2$,
B(OH)$_2$,
ZnR$^5$

In some embodiments, the presently disclosed MOF catalysts are not only highly enantioselective (up to >99% e.e.), but can be more active than their homogeneous counterparts (e.g., similar metal complexes, such as Ru or Rh complexes, that are not present in a MOF and that can be dissolved in a solution with the substrates involved in a reaction being catalyzed). These MOFs provide a versatile family of single-site solid catalysts for catalyzing a broad range of asymmetric organic transformations with up to more than 99% e.e., including the addition of aryl and alkyl groups to α,β-unsaturated ketones, the addition of arylboronic acids to α,β-unsaturated ketones and aldimines, and the hydrogenation of substituted alkene and carbonyl compounds. The MOFs can also be used to catalyze reductive cyclization, Pauson-Khand-type reactions, and intramolecular Alder-Ene reactions of 1,6-enynes with high yields and e.e.'s. In addition, the MOF catalysts are stable and recyclable.

For instance, in some embodiments, the presently disclosed subject matter provides a method for preparing an asymmetric compound comprising contacting a substrate (or substrates) capable of forming an asymmetric product by an asymmetric reaction with one of the presently disclosed asymmetric MOF-based catalysts. In some embodiments, the asymmetric reaction is selected from the group consisting of hydrogenation; isomerization, optionally the isomerization of an allylamine, an allyl alcohol, or an α,β-unsaturated ketone; allylic substitution; a coupling reaction, optionally wherein the coupling reaction is a Buchwald-Hartwig amination, an intramolecular Heck reaction, or an intermolecular Heck reaction; conjugate addition, optionally wherein the conjugate addition is a Michael addition or an azo-Michael addition; an aldol reaction; a Mannich-type reaction; nucleophilic addition, optionally wherein the nucleophilic addition is to a carbonyl or imine group and/or wherein the nucleophilic addition is a cyanation, a propargylation, an allylation, a dienylation, an arylation, an alkenylation, or an alkylation; hydroformylation; hydroacylation; hydroboration; hydroamination; intra- or intermolecular hydrosilylation; an α-substitution reaction, optionally wherein the α-substitution reaction is a protonation, a fluorination, an amination, an arylation, or an orthoester alkylation; an ene reaction; a Diels-Alder reaction; a Pauson-Khand reaction; an Alder-Ene reaction; an enyne intramolecular cyclization; a [2+2+2] cycloaddition; a [3+2] cycloaddition; and a ring-opening reaction. In some embodiments, the substrate is an α,β-unsaturated ketone, a β-keto ester, an aldimine, an alkene, or a 1,6-enyne. In some embodiments, the asymmetric reaction is selected from the group consisting of 1,4-addition of an arylboronic acid to an α,β-unsaturated ketone, 1,2-addition of trimethylaluminum to an α,β-unsaturated ketone, 1,2-addition of an arylboronic acid to an aldimine, hydrogenation of a β-keto ester, hydrogenation of a substituted alkene, reductive cyclization of a 1,6-enyne, an Alder-Ene reaction of a 1,6-enyne, and a Pauson-Khand reaction of a 1,6-enyne.

The contacting can take place in any suitable solvent, e.g., a solvent in which the substrate can be dissolved. In some embodiments, the solvent is an ether, such as tetrahydrofuran or dioxane; a halogenated alkene, such as dichloromethane, dichloroethane, or chloroform; an aromatic solvent, such as benzene, toluene, or xylene; an alcohol, such as methanol or ethanol; water, or mixtures thereof. In some embodiments, the solvent is an unconventional solvent, such as supercritical carbon dioxide. In some embodiments, no solvent is present. In some embodiments, the contacting takes place in the presence of a gas, such as hydrogen gas, and/or under pressure. In some embodiments, the contacting is done in conjunction with heating or cooling.

In some embodiments, the asymmetric reaction is done in a flow reactor, e.g., wherein the catalyst is present in a reaction chamber into which a solvent or solvents can be pumped in and out and wherein the solvent or solvents can comprise a substrate or substrates dissolved therein.

The presently disclosed catalysts can have high turnover number (TON). For example, in some embodiments, the presently disclosed MOF-based catalysts can have a TON of greater than about 50, greater than about 100, greater than about 200, or greater than about 400. In some embodiments, the presently disclosed catalysts can be used at low catalyst loadings, e.g., at less than about 10 mole %, less than about 5 mole %, less than about 3 mole %, less than about 1 mole %, less than about 0.5 mole %, or less than about 0.2 mole %. In some embodiments, the catalysts can be used at a catalyst loading of between about 0.001 mole % and about 3 mole %. Accordingly, in some embodiments, the contacting can be performed wherein the catalyst is present at about 3 mole % or less compared to the substrate.

Figure 16:
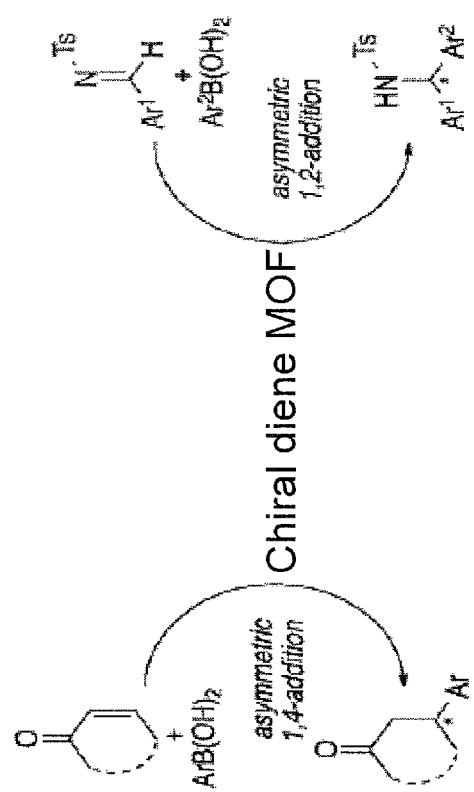
FIG. 16 is a schematic drawing showing some of the catalytic activities of presently disclosed metal-organic framework (MOF) catalysts comprising chiral diene-based organic bridging ligands.

In some embodiments, the presently disclosed subject matter provides for the use of a MOF catalyst comprising a chiral phosphine bridging ligand in catalyzing a reaction selected from an asymmetric 1,4 addition of an arylboronic acid to an α,β-unsaturated ketone, an asymmetric 1,2-addition of trimethylaluminum to an α,β-unsaturated ketone, an asymmetric hydrogenation of a β-keto ester, an asymmetric hydrogenation of a substituted alkene, an asymmetric reductive cyclization of a 1,6-enyne, an asymmetric Alder-Ene reaction of a 1,6-enyne, or a intramolecular Pauson-Khand reactions of a 1,6-enyne. See, e.g., FIG. 12. In some embodiments, the presently disclosed subject matter provides for the use of a MOF catalyst comprising a chiral diene bridging ligand in catalyzing a reaction selected from an asymmetric 1,4-addition of an arylboronic acid to an α,β-unsaturated ketone or a asymmetric 1,2-addition of an arylboronic acid to an aldimine. See FIG. 16.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods

Solvents were purchased from Fisher (Thermo Fisher Scientific, Waltham, Mass., United States of America) and used without further purification. All of the reactions and manipulations were carried out under nitrogen with the use of standard inert atmosphere and Schlenk techniques. $^1$H NMR spectra were recorded on a Bruker NMR 400 DRX spectrometer (Bruker Corporation, Billerica, Mass., United States of America) at 400 MHz and referenced to the proton resonance resulting from incomplete deuteration of the deuterated chloroform (δ 7.26). $^{13}$C{1H} NMR spectra were recorded at 100 MHz, and all of the chemical shifts are reported downfield in ppm relative to the carbon resonance of chloroform-d (δ 77.00). Thermogravimetric analysis (TGA) was performed in air using a Shimadzu TGA-50 (Shimadzu Corporation, Kyoto, Japan) equipped with a platinum pan. Single-crystal X-ray diffraction and powder X-ray diffraction (PXRD) patterns were collected on a Bruker SMART APEX II diffractometer (Bruker Corporation, Billerica, Mass., United States of America) using Cu radiation. The PXRD patterns were processed with the APEX 2 package using PILOT plug-in. Conversions and e.e. values were determined by gas chromatography (GC) and high performance liquid chromatography (HPLC) using a Shimadzu GC-2010 gas chromatograph (Shimadzu Corporation, Kyoto, Japan) equipped with a flame ionization detector (FID) and a Shimadzu SCL-10A HPLC (Shimadzu Corporation, Kyoto, Japan) equipped with a SPD-M10A photodiode array detector.

Example 2

Synthesis of 4,4'-DiiodoBINAP oxide

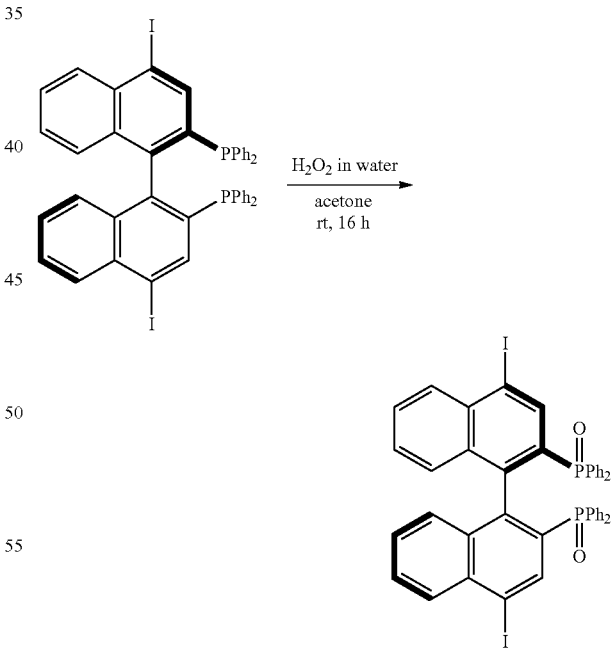

4,4'-DiiodoBINAP oxide was prepared from 4,4'-diiodoBINAP (Hu et al., Angew. Chem., Int. Ed., 2004, 43, 2501) as shown in Scheme 6. 4,4'-diiodoBINAP (1.14 g, 1.30 mmol) was charged into a 100 mL round bottom flask and dissolved in acetone (75 mL). 30 wt % hydrogen peroxide (8 mL) was added and the solution was stirred for 16 hours. Manganese dioxide was added to quench the reaction, and the mixture was allowed to stir for 30 min. The solid was filtered off, and the volatiles were removed in vacuo. The solution was then diluted with water to precipitate the product which was collected by vacuum filtration to yield a white powder (1.00 g, 85% yield) and was used without further purification. $^{31}$P NMR (CDCl$_3$): δ 27.12. $^1$H NMR (CDCl$_3$): δ 6.75 (d, J=8.5 Hz, 2H), 6.85 (t, J=7.5 Hz, 2H), 7.21-7.31 (m, 8H), 7.35-7.47 (m, 10H), 7.62 (dd, J=12.5, 7.5 Hz, 4H), 8.00 (d, J=11.5 Hz, 2H), 8.05 (d, J=8.5 Hz, 2H).

Example 3

Synthesis of 4,4'-Bis(methyl-4-carboxyphenylethynyl)BINAP oxide

Scheme 7. Synthesis of 4,4'-Bis(methyl-4-carboxyphenylethynyl)BINAP oxide.

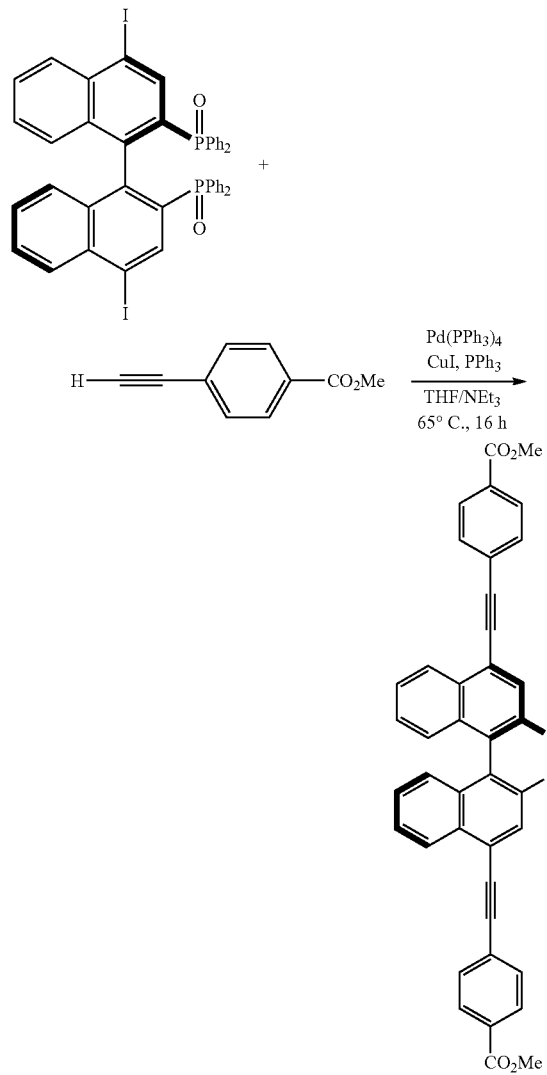

4,4'-Bis(methyl-4-carboxyphenylethynyl)BINAP oxide was prepared as shown in Scheme 7. 4,4'-diiodo-BINAP oxide (855 mg, 0.977 mmol), methyl-4-carboxyphenylacetylene (318 mg, 1.99 mmol), tetrakis(triphenylphosphine)palladium(0) (91.9 mg, 0.0795 mmol), and triphenylphosphine (25.0 mg, 0.0953 mmol) were charged into a 100 mL round bottom flask, and then THF (38 mL) and TEA (38 mL) were added. The solution was degassed for 30 minutes, and copper(I) iodide (28.8 mg, 0.151 mmol) was added. The solution was degassed further for 10 minutes and then heated under nitrogen at 65° C. for 15 h. The solution was then cooled to room temperature, and the volatiles were removed in vacuo. The remaining solids were then purified by column chromatography using 20% ethyl acetate in chloroform, giving pure 4,4'-bis(methyl-4-carboxyphenylethynyl)BINAP oxide as a white solid (612 mg, 0.632 mmol, 65% yield). $^{31}$P NMR (CDCl$_3$): δ 27.93. $^1$H NMR (CDCl$_3$): δ 3.98 (s, 6H), 6.81-6.88 (m, 4H), 7.29-7.35 (m, 16H), 7.42-7.51 (m, 12H), 8.10 (d, J=10 Hz, 4H), 8.45 (d, J=10 Hz, 2H). $^{13}$C NMR (CDCl$_3$): δ 52.25, 90.36, 94.18, 120.26 (d, J=14 Hz), 126.01, 126.50, 127.40, 127.83-128.78, 129.57-129.79, 131.18, 131.43-133.21, 133.68, 134.26, 143.59, 166.50.

Example 4

Synthesis of 4,4'-Bis(methyl-4-carboxyphenylethynyl)BINAP (Me$_2$L)

Scheme 8. Synthesis of 4,4'-Bis(methyl-4-carboxyphenylethynyl)BINAP (Me$_2$L).

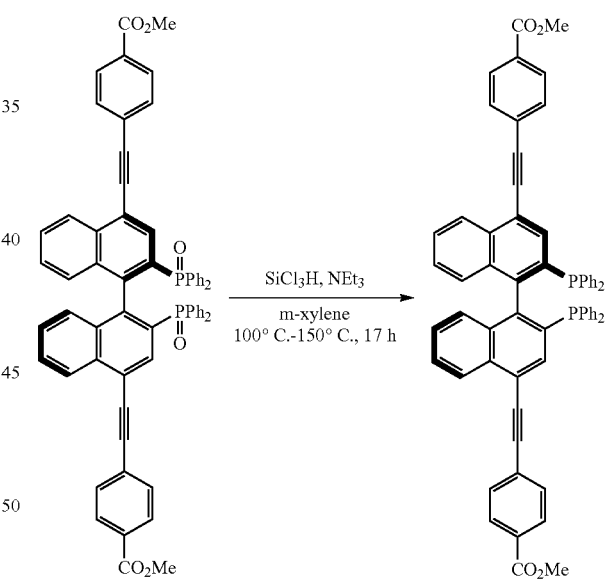

4,4'-Bis(methyl-4-carboxyphenylethynyl)BINAP was prepared as shown in Scheme 8. 4,4'-bis(methyl-4-carboxyphenylethynyl)BINAP oxide (636.5 mg, 0.656 mmol) was charged into a 25 mL reaction vessel and dissolved in anhydrous m-xylene (10 mL). TEA (0.325 mL, 2.61 mmol) was added, and the solution was degassed for 30 minutes. trichlorosilane (0.270 mL, 2.65 mmol) was added, and the reaction was sealed and heated to 100° C. for 1 h and then heated to 150° C. for 16 h. The reaction mixture was cooled to room temperature, and water (5 mL) and 6 M NaOH(aq) (5 mL) were added. The mixture was allowed to stir for 1 h, and then filtered. The organics were concentrated in vacuo. Methanol was then added to precipitate the white product, Me$_2$L (465 mg, 0.495 mmol, 76% yield). $^{31}$P NMR (CDCl$_3$): δ −15.15. $^1$H NMR (CDCl$_3$): δ 3.99 (s, 6H), 6.84 (d, J=8.8 Hz, 2H), 6.97 (t, J=6.8 Hz, 2H), 7.08-7.26 (m, 20H), 7.51 (t, J=8 Hz, 2H), 7.74 (d, J=8 Hz, 4H), 7.83 (s, 2H), 8.11 (d, J=8 Hz, 4H), 8.48 (d, J=8.4 Hz, 2H). $^{13}$C NMR (CD$_2$Cl$_2$): δ 55.22, 90.71, 94.08, 120.83, 125.88, 126.46, 127.52-128.72, 129.56, 131.55, 132.66-133.10, 134.22-134.82, 135.59-135.69, 136.22-136.34, 137.07-137.20.

Example 5

Synthesis of 4,4'-Bis(4-carboxyphenylethynyl)BINAP (H$_2$L)

Scheme 9. Synthesis of 4,4'-Bis(4-carboxyphenylethynyl)BINAP (H$_2$L).

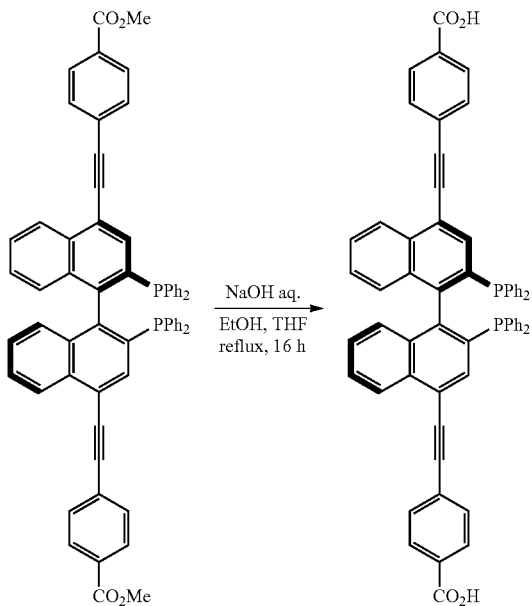

As described in Scheme 9, Me$_2$L (443 mg, 0.472 mmol) was dissolved in a mixture of THF (20 mL), EtOH (20 mL), and 6 M NaOH(aq) (20 mL), and the solution was degassed for 15 minutes. The reaction mixture was then heated at 75° C. under nitrogen for 16 h. The reaction mixture was then cooled to room temperature and poured into a concentrated solution of citric acid to precipitate the white product H$_2$L (410 mg, 0.450 mmol, 95% yield). $^{31}$P NMR (CDCl$_3$/MeOD): δ −11.37. $^1$H NMR (CDCl$_3$/MeOD): δ 6.92 (d, J=8.4 Hz, 2H), 7.06 (t, J=3.2 Hz, 2H), 7.19-7.38 (m, 20H), 7.61 (t, J=6.8 Hz, 2H), 7.84 (d, J=8.4 Hz, 4H), 7.89 (s, 2H), 8.01 (d, J=8.4 Hz, 4H), 8.79 (d, J=8.4 Hz, 2H). $^{13}$C NMR (CDCl$_3$/MeOD): δ 90.20, 93.90, 120.62, 125.62, 126.23, 127.29, 127.41, 127.58, 127.67, 127.85, 127.93, 127.97, 128.01, 128.04, 128.07, 128.50, 120.53, 129.98, 131.16, 131.25, 132.45, 132.55, 132.65, 132.69, 132.80, 132.85, 133.94, 134.01, 134.12, 134.23, 134.31, 134.50, 135.26, 135.89, 135.94, 136.01, 136.79, 145.33, 145.73, 175.00.

Example 6

Synthesis and Characterization of MOF 1

Synthesis of Zr$_6$(OH)$_4$O$_4$L$_6$·126DMF·156H$_2$O (1)

Figure 3B:
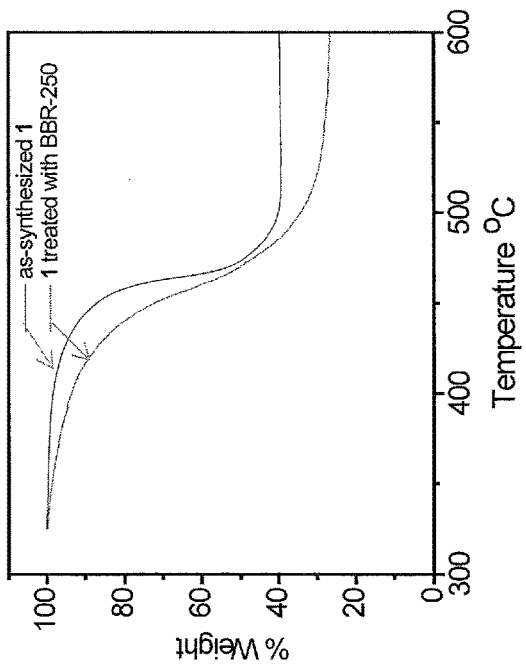
FIG. 3B is a graph showing the thermogravimetric analysis (TGA) of the metal-organic framework (MOF) 1 described for FIG. 3A and that of the same MOF treated with the organic dye BBR-250 overnight. A dye uptake of 13.5% was determined based on the organic weight loss at 325-600 degrees Celsius (° C.).
Figure 3A:
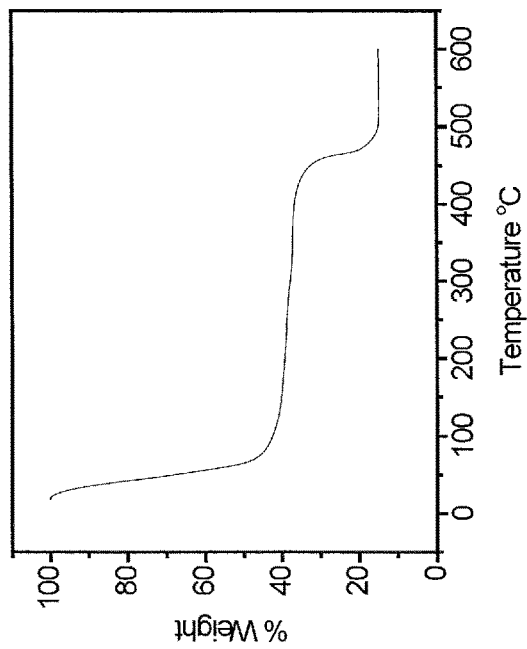
FIG. 3A is a graph showing the thermogravimetric analysis (TGA) of freshly prepared metal-organic framework (MOF) 1, comprising a (2,2'-bis(diphenylphosphino)-1,1-binaphthyl) (BINAP)-based organic bridging ligand and zirconium-oxo clusters. A solvent weight loss of 60% was observed in the room temperature to 100 degrees Celsius (° C.) range.

H$_2$L (12.0 mg, 13.2 μmol) and ZrCl$_4$ (3.0 mg, 13 μmol) were dissolved in DMF (1.8 mL). To this solution, trifluoroacetic acid (12 μL) was added. The solution was added to a glass tube and degassed by three successive freeze-pump-thaw cycles. After the third cycle, the solution was frozen and placed under vacuum, and the glass tube was sealed with a natural gas-O$_2$ torch. The sealed tube was then heated in a 120° C. oven for three days, resulting in colorless crystals of 1 (17.6 mg, 5.81 μmol, 44% yield). Solvent content calculated from proposed formula: 45.9% DMF; 14.0% H$_2$O. From solvent analysis: 46.0% DMF; 14.0% H$_2$O. TGA curves of freshly prepared 1 are shown in FIGS. 3A and 3B.

X-Ray Structure Determination of MOF 1:

Single crystal X-ray diffraction of 1 was collected on a Bruker APEX II CCD-based diffractometer (Bruker Corporation, Billerica, Mass., United States of America) with a Cu-target X-ray tube. The crystals were mounted inside a capillary tube (0.7 mm ID) with small amount of mother liquid to prevent solvent loss from the crystal frameworks. The frames were integrated with the Bruker SAINT© (Bruker Corporation, Billerica, Mass., United States of America) build in APEX II software package using a narrow-frame integration algorithm, which also corrects for the Lorentz and polarization effects. Absorption corrections were applied using SADABS. Structures were solved by direct methods and refined to convergence by least squares method on F$^2$ using the SHELXTL software suite.

Due to the disorder caused by the free rotation of the carbon-carbon single bonds around the ethynyl groups the L ligands, the naphthalene and phosphine fragments of the structure could not be located in the electron density map. These fragments were input at their optimized geometry and treated as rigid bodies in refinement cycles. SQUEEZE subroutine of the PLATON software suite was applied to remove the scattering from the highly disordered guest molecules. The resulting new HKL4 files were used to further refine the structures. Due to the relatively weak diffraction and low resolution, which is not uncommon for this kind of framework with very large solvent accessible void space, restraints (SIMU and DELU) on displacement parameters, and DFIX for bond lengths are applied. All benzene and naphthalene rings are constrained to ideal geometry. Non-hydrogen atoms are refined isotropically.

Single crystal datasets for Ru and Rh-metalated 1 were also collected on the same instrument. Cubic unit cells for both metalated MOFs were obtained. The cell dimensions are the same as 1 within acceptable error (a=46.076 Å for 1.Ru and 46.043 Å for 1.Rh), indicating the MOF structure did not change after metalation. Although the Zr$_6$(O)$_4$(OH)$_4$ SBUs and parts of the L ligands can be identified on the electron density maps, Ru or Rh atoms could not be located on the electron density maps due to the poor quality of the datasets as well as the intrinsic rotation disorder described above. Table 1, below, shows crystal data and structure refinements for MOF 1.

TABLE 1

Crystal data and structure refinements of MOF 1.

| Empirical formula | Zr$_6$(O)$_4$(OH)$_4$L$_6$ | Density (calcd. g/cm$^3$) | 0.416 |
|---|---|---|---|
| Formula weight | 6144.63 | Absorption coeff. (mm$^{-1}$) | 0.863 |

TABLE 1-continued

Crystal data and structure refinements of MOF 1.

| | | | |
|---|---|---|---|
| Temperature (K) | 298 | F(000) | 12608.0 |
| Wavelength (Å) | 1.54178 | Crystal size (mm) | |
| Crystal system | cubic | Crystal color & shape | |
| Space group | F23 | θ range data collection | 1.66-30.83 |
| Unit cell dimensions | a = 46.116(2) | Limiting indices | −30 <= h <= 29, |
| | b = 46.116(2) | | −18 <= k <= 30, |
| | c = 46.116(2) | | −28 <= l <= 26 |
| | α = 90 | Reflection collected | 23648 |
| | β = 90 | Independent reflections | 2557 |
| | γ = 90 | R(int) | 0.138 |
| | | Data/restraints/parameters | 2557/42/31 |
| | | Goodness-of-fit on $F^2$ | 1.375 |
| Volume (Å$^3$) | 98073(8) | Final R indices [I > 2σ(I)] | R1 = 0.1026, wR2 = 0.2456 |
| Z | 4 | R indices (all data) | R1 = 0.1383, wR2 = 0.2594 |

1 crystalizes in the F23 chiral space group. The asymmetric unit of 1 contains one half of the L ligand and one twelfth of the $Zr_6O_4(OH)_4$ SBU. The MOF contains both octahedral and tetrahedral cages with edges measuring 23 Å. See FIG. 2. However, the naphthyl and diphenylphosphino moieties could not be located on the electron density maps due to the free rotation of the C—C single bonds around the ethynyl groups of the L ligand. The solvent accessible void space was calculated to be 76.3% using PLATON. Thermogravimetric analysis (TGA) of 1 indicated a solvent content of 60% (see FIG. 3A), whereas a combination of TGA and NMR solvent analyses gave the complete formula of $Zr_6(OH)_4O_4L_6 \cdot 126DMF \cdot 156H_2O$ for 1. Dye uptake measurements showed that 13.5 wt % of brilliant blue R-250 could be loaded into the channels (see FIG. 3B), indicating the presence of large open channels in 1 that can accommodate large dye molecules and metalating agents. Nitrogen adsorption measurements, however, did not show porosity for 1, presumably due to framework distortion upon removal of solvent molecules, a phenomenon that has been observed frequently for mesoporous MOFs with large open channels. See Ma et al., Nat. Chem., 2010, 2, 838; and Férey et al., Acc. Chem. Res., 2005, 38, 217.

Example 7

Post-Synthetic Metalation of 1

Post-Synthetic Metalation of 1 with $Rh(Nbd)_2BF_4$:

Freshly prepared MOF 1 (7.6 mg, 2.5 μmol) was weighed onto a filter paper and then charged into a 1 dram vial. After addition of THF (2.0 mL) and $Rh(nbd)_2BF_4$ (100 μL, 2.5 μmol, 0.025M solution in $CH_2Cl_2$), the mixture was allowed to stand for overnight, and then the metalated 1 was centrifuged out of suspension and washed with THF.

Post-Synthetic Metalation of 1 with $Ru(Cod)(2-methyl-allyl)_2$

Freshly prepared MOF 1 (2.7 mg, 0.89 μmol) was weighed onto a filter paper and then charged into a 1 dram vial. Methanol was then added followed by Ru(cod)(2-methyl-allyl)$_2$ (1.4 mg, 4.4 μmol). The vials were sealed with a rubber septum and then degassed by repeated vacuum/N$_2$ cycles. HBr (151 μL, 43.8 μmol, 0.29 M solution in MeOH) was added to the solution and the solution degassed further. The now orange solution was then stirred for 16 h under N$_2$. The MOF was then centrifuged out of suspension and washed with $CH_2Cl_2$ and then MeOH.

Determination of the Amount of Metal Catalyst:

Amount of metal catalyst was calculated by the following way:

(Amount of Metal Catalyst)=(Weight of MOF)/(Molecular Weight of MOF)×(Number of Ligands in MOF formula)×(Ratio of Metal Catalyst to Ligand)

Figure 4B:
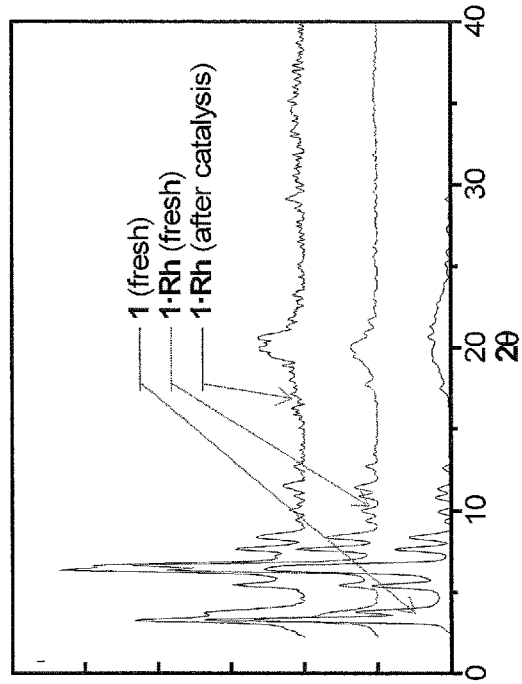
FIG. 4B is a graph showing powder x-ray diffraction (PXRD) patterns for metalated and unmetalated metal-organic framework (MOF) 1, containing a (2,2'-bis(diphenylphosphino)-1,1-binaphthyl) (BINAP)-based organic bridging ligand and zirconium-oxo clusters. The bottom pattern is a PXRD pattern for unmetalated MOF 1. The middle pattern is a PXRD pattern for MOF 1 metalated with rhodium (Rh), i.e., 1.Rh. The top pattern is for 1.Rh recovered from trimethylaluminum addition reactions. The broad peaks at about 20 θ are from glass capillary tubes.
Figure 4A:
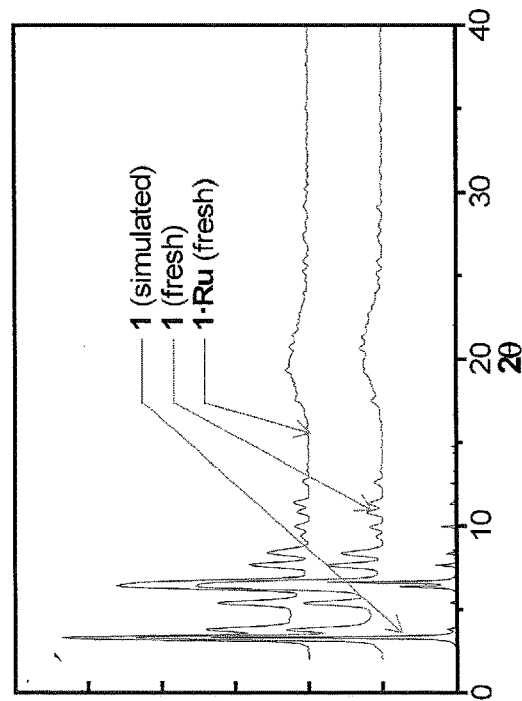
FIG. 4A is a graph showing powder x-ray diffraction (PXRD) patterns for metalated and unmetalated metal-organic framework (MOF) 1, containing a (2,2'-bis(diphenylphosphino)-1,1-binaphthyl) (BINAP)-based organic bridging ligand and zirconium-oxo clusters. The bottom pattern is a simulated PXRD pattern for unmetalated MOF 1. The middle pattern is an experimental PXRD pattern for unmetalated MOF 1. The top pattern is for MOF 1 metalated with ruthenium (Ru), i.e., 1.Ru.

For example, when the weight of MOF is 7.6 mg and the MOF was metalated by $[Rh(nbd)_2]BF_4$, the amount of rhodium catalyst is (7.6 mg)/(18166)×(6)×(0.33)=0.083 μmol Discussion:

The post-synthetic metalation of 1 was performed by treating 1 with one equiv of $[Rh(nbd)_2](BF_4)$ to afford 1.Rh or with 4.9 equiv of Ru(cod)(2-Me-allyl)$_2$ followed by HBr to afford 1.Ru (relative to the H$_2$L equivalents in 1). PXRD indicated that the crystallinity of 1 was maintained in both 1.Rh and 1.Ru after the metalation reactions. See FIGS. 4A and 4B. Inductively coupled plasma-mass spectrometry (ICP-MS) analyses of the Zr:Rh and Zr:Ru ratios of the digested metalated MOFs gave Rh and Ru loadings of 33% and 50% for 1.Rh and 1.Ru, respectively. Although 1.Rh and 1.Ru appear to remain single crystalline, the rotational disorder of the L ligands and the partial metalation make it difficult to study the Ru and Rh coordination environments by single crystal X-ray crystallography. Instead, X-ray absorption fine structure spectroscopy (XAFS) was used to determine the Ru coordination environment in 1.Ru. Ru K-edge spectra were collected for powder samples of both $Ru(Me_2L)(MeOH)_2Br_2$ and 1.Ru. Comparison of these data reveals nearly identical coordination environments of the Ru ions in the two systems.

Example 8

Synthesis of BINAP-Containing Dibenzoic Acid Ligand

A chiral BINAP-containing dibenzoic acid binding ligand, H$_2$DB-BINAP, can be prepared as described in Scheme 10, below.

Scheme 10. Synthesis of BINAP-containing dibenzoic acid (H₂DB-BINAP).

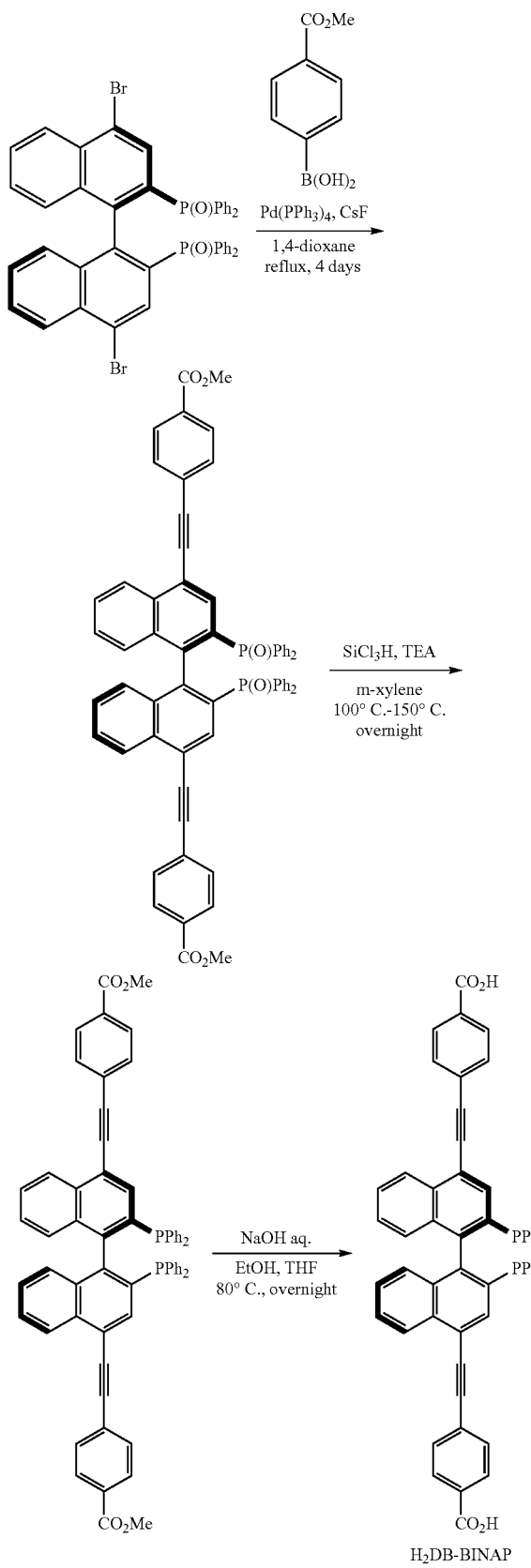

H₂DB-BINAP

Dimethyl 4,4'-(2,2'-bis(diphenylphosphoryl)-[1,1'-binaphthalene]-4,4'-diyl)dibenzoate: (4,4'-dibromo-[1,1'-binaphthalene]-2,2'-diyl)bis(diphenylphosphine oxide) (1.00 g, 1.23 mmol), 4-methoxycarbonylphenylboronic acid (764 mg, 4.25 mmol), were charged into a round bottom flask, and then 1,4-dioxane (46 mL) was added. The solution was degassed for 20 minutes, and tetrakis(triphenylphosphine)palladium(0) (320 mg, 0.277 mmol), and cesium fluoride (1.07 g, 7.04 mmol) were added. The solution was degassed further for 20 minutes and then stirred under reflux for 4 days. The solution was then cooled to room temperature, and the water was added to the mixture. After extraction with $CH_2Cl_2$, the combined organic extracts were dried over $MgSO_4$ and filtered. After evaporation of the solvent, the residue was subjected to flash column chromatography on silica gel (EtOAc and $CHCl_3$ as eluent) to afford dimethyl 4,4'-(2,2'-bis(diphenylphosphoryl)-[1,1'-binaphthalene]-4,4'-diyl)dibenzoate (350 mg, 0.379 mmol, 31% yield). $^{31}$P NMR ($CDCl_3$): δ 30.12. $^1$H NMR ($CDCl_3$): δ 3.97 (s, 6H), 6.94 (t, J=7.8 Hz, 2H), 7.03 (d, J=8.5 Hz, 2H), 7.18-7.29 (m, 8H), 7.31-7.50 (m, 12H), 7.58 (d, J=8.0 Hz, 4H), 7.68 (d, J=7.5 Hz, 2H), 7.70 (d, J=7.5 Hz, 2H), 7.84 (d, J=8.5 Hz, 2H), 8.16 (d, J=8.5 Hz, 4H).

Dimethyl 4,4'-(2,2'-bis(diphenylphosphanyl)-[1,1'-binaphthalene]-4,4'-diyl)dibenzoate: Dimethyl 4,4'-(2,2'-bis(diphenylphosphoryl)-[1,1'-binaphthalene]-4,4'-diyl)dibenzoate (300 mg, 0.325 mmol) was charged into a reaction vessel and dissolved in anhydrous m-xylene (5 mL). TEA (0.180 mL, 1.29 mmol) was added, and the solution was degassed for 30 minutes. trichlorosilane (0.130 mL, 1.29 mmol) was added, and the reaction was sealed and heated to 100° C. for 1 h and then heated to 150° C. for 16 h. The reaction mixture was cooled to room temperature, and water and 3 M NaOH(aq) were added. The mixture was allowed to stir for 10 min, and then filtered. The combined organic extracts were dried over $MgSO_4$ and filtered. After evaporation of the solvent, the residue was subjected to flash column chromatography (silica gel, hexanes/$CH_2Cl_2$=1/1) to give 4,4'-(2,2'-bis(diphenylphosphanyl)-[1,1'-binaphthalene]-4,4'-diyl)dibenzoate (261 mg, 0.293 mmol, 90% yield). $^{31}$P NMR ($CDCl_3$): δ−14.92. $^1$H NMR ($CDCl_3$): δ 3.97 (s, 6H), 6.95-7.04 (m, 4H), 7.07-7.17 (m, 18H), 7.17-7.22 (m, 2H), 7.32-7.37 (m, 2H), 7.41-7.44 (m, 2H), 7.58 (d, J=8.0 Hz, 4H), 7.90 (d, J=8.5 Hz, 2H), 8.14 (d, J=8.5 Hz, 4H).

4,4'-(2,2'-Bis(diphenylphosphanyl)-[1,1'-binaphthalene]-4,4'-diyl)dibenzoic acid (H₂DB-BINAP): Dimethyl 4,4'-(2,2'-bis(diphenylphosphanyl)-[1,1'-binaphthalene]-4,4'-diyl)dibenzoate (1.50 g, 1.68 mmol) was dissolved in a mixture of THF (60 mL), EtOH (60 mL), and 3 M NaOH(aq) (60 mL), and the solution was degassed for 15 minutes. The reaction mixture was then heated at 80° C. under nitrogen for overnight. The reaction mixture was then cooled to room temperature and poured into a concentrated solution of citric acid to precipitate the white product H₂DB-BINAP (966 mg, 1.12 mmol, 67% yield). $^{31}$P NMR (DMSO-$d_6$): δ −15.84. $^1$H NMR (DMSO-$d_6$): δ 6.89 (d, J=8.5 Hz, 2H), 7.00-7.13 (m, 8H), 7.19-7.31 (m, 16H), 7.45 (t, J=7.5 Hz, 2H), 7.61 (d, J=8.0 Hz, 4H), 7.85 (d, J=8.5 Hz, 2H), 8.10 (d, J=8.5 Hz, 4H).

Example 9

Synthesis of Non-Chiral Bridging Ligands

Synthesis of Dimethyl-4-4'-((2-nitro-[1,1'-biphenyl]-4,4'-diyl)bis(ethyne-2,1-dilyl))dibenzoate ($Me_2L_2$)

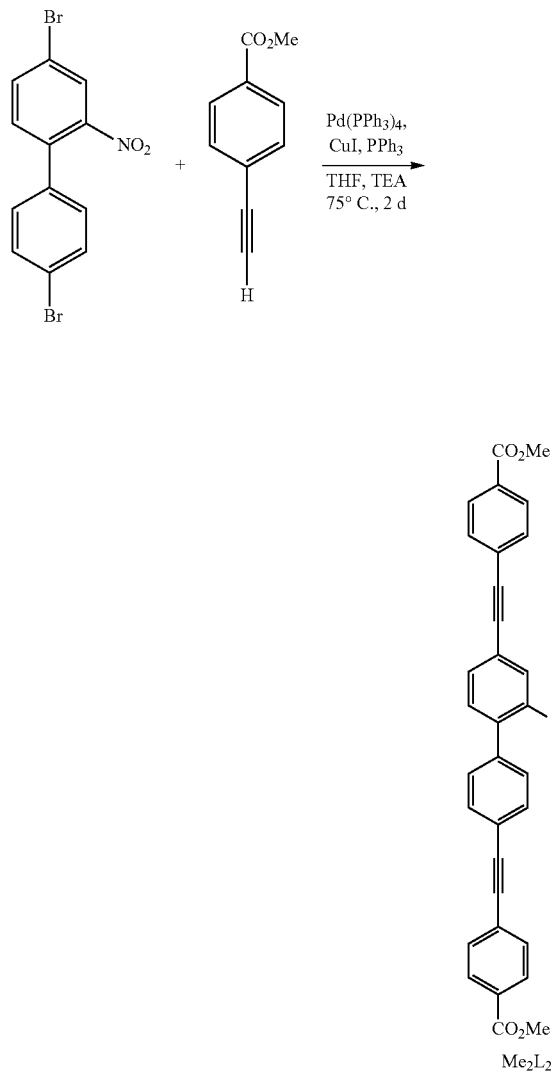

Dimethyl-4-4'4(2-nitro-[1,1'-biphenyl]-4,4'-diyl)bis(ethyne-2,1-dilyl))dibenzoate ($Me_2L_2$) was prepared as shown in Scheme 11, above. A mixture of tetrakis(triphenylphosphine)palladium(0) (288.9 mg, 0.2500 mmol), triphenylphosphine (78.7 mg, 0.300 mmol), and copper(I) iodide (95.2 mg, 0.500 mmol) was dissolved in THF (6.3 mL) and triethylamine (TEA, 6.3 mL). To the mixture were added 4,4'-dibromo-2-nitrobiphenyl (893 mg, 2.50 mmol) and methyl 4-ethynylbenzoate (1.20 g, 7.49 mmol), and the resulting mixture was stirred under nitrogen at 75° C. for 2 d. The solution was then cooled to room temperature, and the volatiles were removed in vacuo. The residue was extracted with $CHCl_3$ and water, and the combined organic extracts were dried over $MgSO_4$ and filtered. After evaporation of the solvent, the residue was subjected to flash column chromatography on silica gel ($CHCl_3$ as eluent) to afford $Me_2L_2$ (816.5 mg, 1.584 mmol, 63% yield). $^1$H NMR (500 MHz, $CDCl_3$): δ 3.94 (s, 3H), 3.95 (s, 3H), 7.34 (d, J=8.5 Hz, 2H), 7.47 (d, J=8.0 Hz, 1H), 7.58-7.65 (m, 6H), 7.77 (dd, J=8.0, 2.0 Hz, 1H), 8.04 (app d, J=8.0 Hz, 3H), 8.06 (d, J=8.5 Hz, 2H). $^{13}$C NMR (125 MHz, $CDCl_3$): δ 52.25, 52.33, 89.26, 89.98, 91.55, 91.62, 123.18, 123.65, 126.74, 127.27, 127.68, 127.96, 129.55, 129.64, 129.69, 130.29, 131.57, 131.71, 131.92, 132.10, 135.09, 135.45, 136.97, 148.97, 166.35, 166.50. ESI-MS: calcd for $C_{32}H_{22}NO_6$ $[M+H]^+$ 516.1. found 516.0.

Synthesis of 4,4'-((2-nitro-[1,1'-biphenyl]-4,4'-diyl)bis(ethyne-2,1-dilyl))dibenzoic acid ($H_2L_2$)

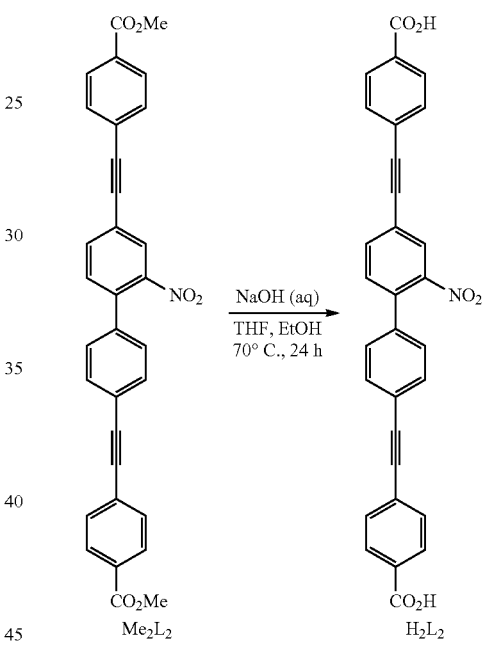

As shown in Scheme 12, above, $Me_2L_2$ (773 mg, 1.50 mmol) was dissolved in a mixture of THF (75 mL), EtOH (75 mL), and 3 M NaOH (aq) (75 mL). After the mixture was stirred at 70° C. for 24 h, 1 M HCl (aq) was slowly added at 0° C., and then the solid was filtered off. The filtrate was extracted with EtOAc, and the combined organic extracts were concentrated in vacuo. The residue was washed with water, hexanes, and MeOH to give pure compound $H_2L_2$ (520 mg, 1.07 mmol, 71% yield). $^1$H NMR (500 MHz, $d_6$-DMSO): δ 7.47 (d, J=8.0 Hz, 2H), 7.70 (app t, J=7.0 Hz, 5H), 7.75 (d, J=8.0 Hz, 2H), 7.95-8.04 (m, 5H), 8.28 (s, 1H), 13.21 (br, 2H). $^{13}$C NMR (125 MHz, $d_6$-DMSO): δ 89.33, 89.83, 91.21, 91.36, 122.10, 122.68, 125.74, 126.38, 127.07, 128.30, 129.61, 129.64, 130.75, 131.18, 131.64, 131.84, 131.98, 132.34, 134.52, 135.51, 136.89, 148.72, 166.63, 166.69. ESI-MS: calcd for $C_{30}H_{16}NO_6$ $[M-H]^-$ 486.1. found 486.2.

Synthesis of Nitro-Containing
Quaterphenyldicarboxylic acid (H₂QPDC)

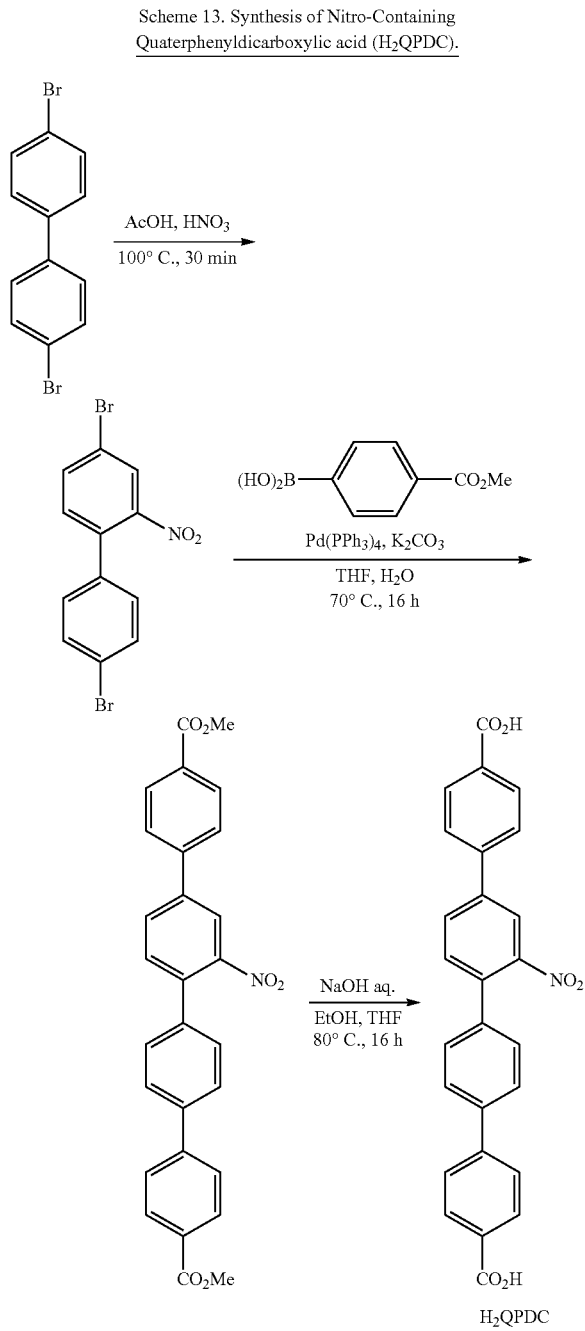

An alternative non-chiral bridging ligand, i.e., nitro-containing quaterphenyldicarboxylic acid (H₂QPDC), can be prepared as shown above in Scheme 13.

Dimethyl 2"-nitro-[1,1':4',1":4",1"'-quaterphenyl]-4,4"'-dicarboxylate: 4,4'-Dibromo-2-nitro-1,1'-biphenyl (3.00 g, 8.40 mmol) and methyl-4-carboxylphenyl boronic acid (3.48 g, 19.3 mmol) were charged to a 2-neck RB flask fitted with a reflux condenser, and then THF (210 mL) was added. The solution was degassed for 30 minutes, and tetrakis (triphenylphosphine)palladium(0) (485 mg, 0.421 mmol) was added. The solution was degassed further for 30 minutes. K₂CO₃ (4.65 g, 33.6 mmol) dissolved in degassed DI water (50 mL) was then added under N₂. The reaction mixture was then heated under N₂ at 90° C. for 48 h. The solution was cooled to room temperature, and the water layer was removed. The volatiles were removed in vacuo, and the remaining solids were purified by column chromatography using chloroform as the eluent, affording dimethyl 2"-nitro-[1,1':4',1":4",1"'-tetraphenyl]4,4"'-dicarboxylate as a light yellow solid (1.40 g, 3.00 mmol, 36% yield). ¹H NMR (500 MHz, CDCl₃): δ 3.96 (s, 3H), 3.97 (s, 3H), 7.47 (d, J=8.0 Hz, 2H), 7.60 (d, J=7.5 Hz, 1H), 7.67-7.78 (m, 6H), 7.90 (d, J=8.0 Hz, 1H), 8.10-8.16 (m, 3H), 8.18 (d, J=8.0 Hz, 2H). ¹³C NMR (125 MHz, CDCl₃): δ 52.15, 52.29, 122.82, 127.02, 127.04, 127.65, 128.49, 129.24, 130.17, 130.19, 130.46, 130.79, 132.50, 135.14, 136.66, 140.07, 140.55, 142.43, 144.65, 149.64, 166.57, 166.89.

2"-Nitro-[1,1':4',1":4",1"'-quaterphenyl]-4,4"'-dicarboxylic acid (H₂QPDC): A suspension of dimethyl 2"-nitro-[1,1':4',1":4",1"'-tetraphenyl]4,4"'-dicarboxylate (400 mg, 0.856 mmol) in THF (65 mL) was heated to 40° C. A solution of KOH (6.17 g, 110 mmol) dissolved in MeOH (20 mL) was then added, and the reaction mixture was stirred at 40° C. for 16 h. The suspension was cooled to room temperature, and the resulting precipitate was collected by centrifugation. The solid was washed with dry THF (20 mL) and re-collected by centrifugation. The solid was suspended in THF (20 mL) and trifluoroacetic acid (3 mL) was slowly added and stirred for 1.5 h at room temperature. H₂O (15 mL) was then added, and the yellow solid was isolated by centrifugation. The collected yellow solid was first washed with THF (10 mL), then Et₂O (10 mL), then dried in vacuo to obtain 2"-nitro-[1,1':4',1":4",1"'-tetraphenyl]4,4"'-dicarboxylic acid (328 mg, 0.746 mmol, 87% yield) as a light yellow powder. ¹H NMR (DMSO-d₆): δ 7.49 (d, J=8.0 Hz, 2H), 7.71 (d, J=8.0 Hz, 1H), 7.82 (d, J=8.0 Hz, 2H), 7.84 (d, J=8.0 Hz, 2H), 7.93 (d, J=8.5 Hz, 2H), 8.01 (d, J=8.5 Hz, 2H), 8.04 (d, J=8.5 Hz, 2H), 8.13 (dd, J=8.0, 1.8 Hz, 1H), 8.34 (d, J=1.5 Hz, 1H). ¹³C NMR (125 MHz, DMSO-d₆): 122.36, 126.88, 127.18, 127.42, 128.55, 129.98, 130.04, 130.12, 130.76, 130.97, 132.50, 133.84, 136.28, 138.97, 139.56, 141.33, 143.38, 149.51, 166.92, 167.06.

Example 10

Synthesis of Additional MOFs Including MOFs with Mixed Organic Bridging Ligands

Synthesis of Mixed Ligand MOF 11:

H₂L (2.3 mg, 2.6 μmol), H₂L₂ (5.0 mg, 10 μmol), and ZrCl₄ (3.0 mg, 13 μmol) were dissolved in DMF (1.8 mL). To this solution, trifluoroacetic acid (15 μL) was added. The solution was added to a glass tube and degassed by three successive freeze-pump-thaw cycles. After the third cycle, the solution was frozen and placed under vacuum, and the glass tube was sealed with a natural gas-O₂ torch. The sealed tube was then heated in a 100° C. oven for 7 days, resulting in crystals of MOF 11 (16.7 mg, 9.13 μmol, 71% yield). MOF 11 has 64% solvent weight based on TGA analysis. The ratio of H₂L to H₂L₂ is 0.13:0.87, which was determined by ¹H NMR after digestion of MOF 11.

Synthesis of Nitro-MOF:

For comparison to MOF 11, an MOF containing only H₂L₂ as the organic bridging ligand was prepared and designated Nitro-MOF. More particularly, Nitro-MOF was prepared as follows:

H$_2$L$_2$ (6.3 mg, 13 µmol), ZrCl$_4$ (3.0 mg, 13 µmol), DMF (1.8 mL), and trifluoroacetic acid (25 µL) were charged to a 1 dram vial. The vial was heated in a 90° C. oven for 7 days resulting in crystals which were washed with DMF (16.5 mg, 10.2 µmol, 79% yield). Nitro-MOF has 63% solvent weight based on TGA analysis).

Single crystal X-ray diffraction of nitro-MOF was collected Bruker APEX II CCD-based detector (Bruker Corporation, Billerica, Mass., United States of America). The crystals were mounted inside a capillary tube (0.2 mm ID) with a small amount of mother liquid to prevent solvent loss from the crystal. The frames were integrated with the Bruker SAINT© build in APEX II software package (Bruker Corporation, Billerica, Mass., United States of America) using a narrow-frame integration algorithm which also corrects for the Lorentz and polarization effects. Absorption corrections were applied using SADABS. Structures were solved by direct methods and refined to convergence by the least squares method on F$^2$ using the SHELXTL software suite.

Due to the disorder caused by the random orientation, the nitro group cannot be located in the electron density map and thus are not presented in the single crystal structure. SQUEEZE subroutine of the PLATON software suite was applied to remove the scattering from the highly disordered guest molecules. The resulting new HKL4 files were used to further refine the structures. Due to the relatively weak diffraction and low resolution, which is not uncommon for this kind of framework with very large solvent accessible void space, restraints (SIMU and DELU) on displacement parameters, and DFIX for bond lengths are applied. All benzene rings are constrained to ideal geometry. Carbon atoms are refined isotropically.

Table 2 provides the crystal data and structure refinements for the nitro-MOF.

The ratios of H$_2$QPDC and H$_2$DB-BINAP in MOF 12 were varied from 10:90 to 90:10. Importantly, Ru-functionalized MOF 12 was highly active for asymmetric hydrogenation of β-keto esters with complete conversions and up to 98% e.e.

For comparison to MOF 12, the MOFs containing only H$_2$QPDC or H$_2$DB-BINAP as the organic bridging ligand were also prepared as follows:

Synthesis of MOF 13.

H$_2$QPDC (20.0 mg, 45.5 µmol) and ZrCl$_4$ (10.6 mg, 45.5 µmol) were dissolved in DMF (2.0 mL). To this solution, trifluoroacetic acid (40 µL) was added. The solution was added to a sample tube and it was then heated in a 100° C. oven for five days, resulting in good yields of crystals.

Synthesis of MOF 14.

H$_2$DB-BINAP (20.0 mg, 23.2 µmol) and ZrCl$_4$ (5.4 mg, 23.2 µmol) were dissolved in DMF (1.5 mL). To this solution, trifluoroacetic acid (30 µL) was added. The solution was added to a sample tube and it was then heated in a 120° C. oven for five days, resulting in crystals.

Figure 5:
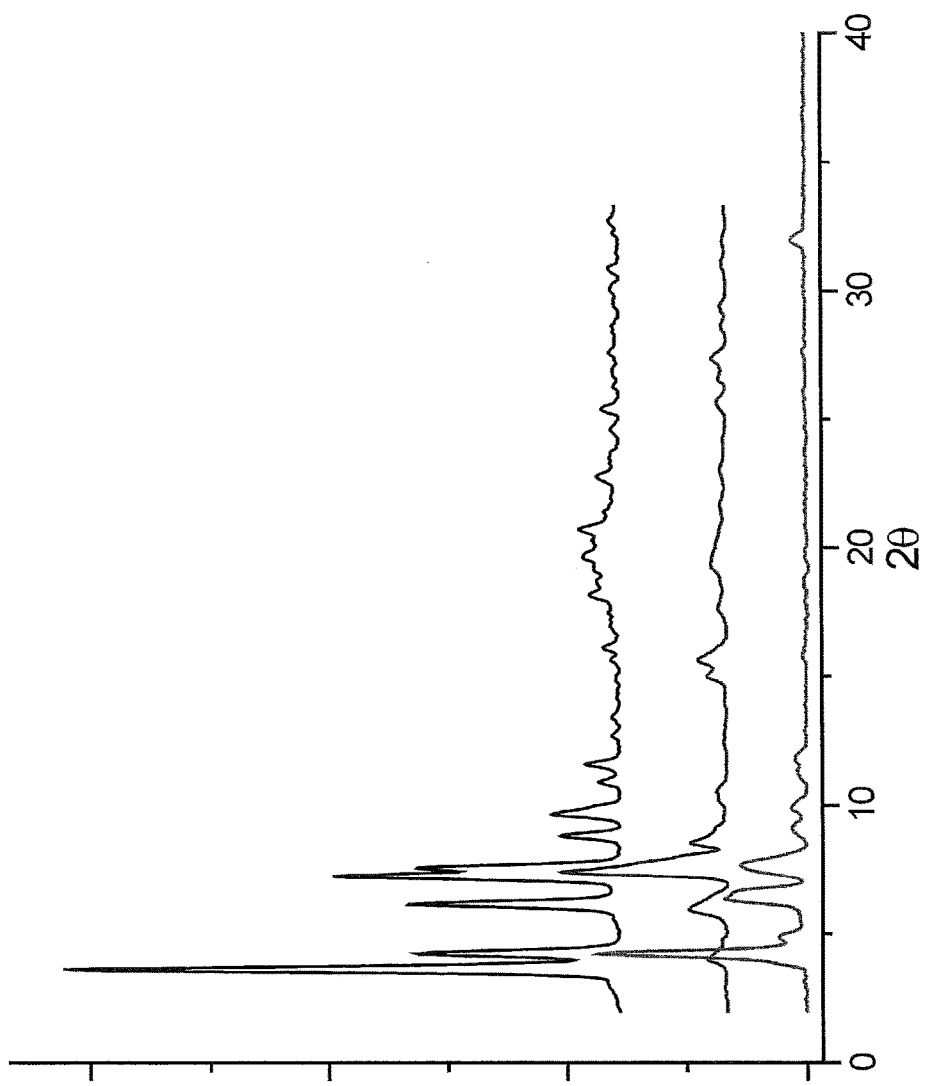
FIG. 5 is a graph showing the powder x-ray diffraction (PXRD) patterns for a metal-organic framework (MOF) containing both chiral and non-chiral organic binding ligands (MOF 12, top pattern), a MOF containing only chiral organic binding ligands (MOF 14, middle pattern), and a MOF containing only non-chiral organic binding ligands (MOF 13, bottom pattern). All three MOFs have the UiO structure.

PRXD of MOFs 12-14 indicated that they belong to the UiO structure. See FIG. 5.

Example 11

Catalysis of Asymmetric 1,4-Addition of Arylboronic Acids to 2-Cyclohexenone Exemplary Procedure for 1.Rh Catalyzed Asymmetric 1,4-Addition of Arylboronic Acids to 2-Cyclohexenone MOF 1 (7.6 mg, 2.5 µmol) was metalated with Rh(nbd)$_2$BF$_4$ (100 µL, 2.5 µmol, 0.025M solution in CH$_2$Cl$_2$) as described above. A mixture of 2-cyclohexenone (8.8 µL, 0.084 mmol), phenylboronic acid (30.6 mg, 0.251

TABLE 2

| Crystal data and structure refinements of nitro-MOF | | | |
|---|---|---|---|
| Empirical formula | Zr$_6$(O)$_4$(OH)$_4$(L$_2$)$_6$ | Density (calcd. g/cm$^3$) | 0.225 |
| Formula weight | 3321.92 | Absorption coeff. (mm$^{-1}$) | 0.091 |
| Temperature | 298 | F(000) | 6704 |
| Wavelength (Å) | 0.41328 | Crystal size (mm) | 0.08 × 0.08 × 0.08 |
| Crystal system | Cubic | Crystal color & shape | Colorless block |
| Space group | Fm$\bar{3}$m | θ range data collection | 0.73-14.18 |
| Unit cell dimensions | a = 46.098(8) | Limiting indices | −43 <= h <= 54, |
|  | b = 46.098(8) |  | −52 <= k <= 30, |
|  | c = 46.098(8) | Reflection collected | 109874 |
|  | α = 90 | Independent reflections | 25574036 |
|  | β = 90 | R(int) | 0.236 |
|  | γ = 90 | Data/restraints/parameters | 4036/34/34 |
|  |  | Goodness-of-fit on F$^2$ | 2.227 |
| Volume (Å$^3$) | 97958(29)( ) | Final R indices [I > 2σ(I)] | R1 = 0.1359, wR2 = 0.3705 |
| Z | 4 | R indices (all data) | R1 = 0.1614, wR2 = 0.3786 |

Synthesis of Mixed Ligand MOF 12:

H$_2$QPDC (15.0 mg, 34.3 µmol), H$_2$DB-BINAP (7.4 mg, 8.6 µmol), and ZrCl$_4$ (10.0 mg, 42.9 µmol) were dissolved in DMF (1.5 mL). After sonication for 5 min, the solution was filtered off with a syringe filter and the syringe filter was rinsed with DMF (0.3 mL). To this filtrate, trifluoroacetic acid (10 µL) was added. The solution was added to a glass tube and degassed by three successive freeze-pump-thaw cycles. After the third cycle, the solution was frozen and placed under vacuum, and the glass tube was sealed with a natural gas-O$_2$ torch. The sealed tube was then heated in a 70° C. oven for ten days, resulting in colorless crystals in good yields.

mmol), triethylamine (11.7 µL, 0.0839 mmol), 1.Rh (2.5 µmol), 1,4-dioxane (2.1 mL), H$_2$O (2.1 mL) was stirred under nitrogen atmosphere at 40° C. for 20 h. After addition of water, the mixture was extracted with Et$_2$O. The combined organic extracts were dried over MgSO$_4$, filtered, and concentrated on a rotary evaporator. The residue was subjected to preparative TLC (silica gel, hexanes/CHCl$_3$/ EtOAc=2/1/0.2) to give (R)-3-phenylcyclohexanone (11.7 mg, 0.0671 mmol, 80%, >99% ee). $^1$H NMR (CDCl$_3$): δ 1.73-1.92 (m, 2H), 2.05-2.12 (m, 1H), 2.12-2.20 (m, 1H), 2.38 (td, J=13.3, 5.8 Hz, 1H), 2.43-2.50 (m, 1H), 2.50-2.63 (m, 2H), 3.01 (tt, J=12.0, 3.8 Hz, 1H), 7.20-7.27 (m, 3H), 7.34 (t, J=7.5 Hz, 2H). The ee was measured by HPLC (Chicalpak AD, 0.6 mL/min, hexanes/2-propanol=99/1, 214 nm).

(R)-3-(3-Methoxycarbonylphenyl)cyclohexanone (85%, 99% ee): $^1$H NMR (CDCl$_3$) δ 1.74-1.84 (m, 1H), 1.93 (qd, J=12.5, 3.3 Hz, 1H), 2.06-2.13 (m, 1H), 2.14-2.22 (m, 1H), 2.40 (td, J=13.5, 6.2 Hz, 1H), 2.44-2.51 (m, 1H), 2.51-2.64 (m, 2H), 3.06 (tt, J=11.8, 4.1 Hz, 1H), 3.92 (s, 3H), 7.37-7.44 (m, 2H), 7.89-7.94 (m, 2H). The ee was measured by HPLC (Chiralpak AD, 0.6 mL/min, hexanes/2-propanol=97/3, 214 nm).

(R)-3-(4-Acetylphenyl)cyclohexanone (99%, 99% ee): $^1$H NMR (CDCl$_3$) δ 1.74-1.94 (m, 2H), 2.05-2.13 (m, 1H), 2.13-2.21 (m, 1H), 2.39 (td, J=13.3, 6.2 Hz, 1H), 2.45-2.52 (m, 1H), 2.52-2.64 (m, 2H), 2.59 (s, 3H), 3.08 (tt, J=11.8, 3.9 Hz, 1H), 7.33 (d, J=8.0 Hz, 2H), 7.94 (d, J=8.0 Hz, 2H). The ee was measured by HPLC (Chiralpak AD, 0.6 mL/min, hexanes/2-propanol=90/10, 254 nm).

Exemplary Procedure for Rh-BINAP Catalyzed Asymmetric 1,4-Addition of Arylboronic Acids to 2-Cyclohexenone:

A mixture of 2-cyclohexenone (14.5 μL, 0.150 mmol), phenylboronic acid (54.9 mg, 0.450 mmol), triethylamine (20.9 μL, 0.150 mmol), [Rh((R)-binap)(nbd)]BF$_4$ (1.4 mg, 1.5 μmol), 1,4-dioxane (3.8 mL), H$_2$O (3.8 mL) was stirred under nitrogen atmosphere at 40° C. for 20 h. After addition of water, the mixture was extracted with Et$_2$O. The combined organic extracts were dried over MgSO$_4$, filtered, and concentrated on a rotary evaporator. The residue was subjected to preparative TLC (silica gel, hexanes/CHCl$_3$/EtOAc=2/1/0.2) to give (R)-3-Phenylcyclohexanone (7.7 mg, 0.0442 mmol, 29%, >99% ee).

Discussion:

Scheme 14, below, shows the asymmetric addition of an arylboronic acid, 3, to 2-cyclohexenone, 2, to form a chiral 3-arylcyclohexanone, 4.

Scheme 14. Asymmetric Addition of Arylboronic Acids to 2-Cyclohexenone

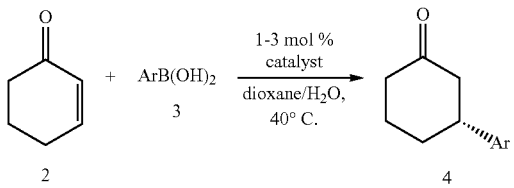

Table 3, below, describes results for catalysis of this addition reaction by 1.Rh or by homogeneous catalysts, e.g., Rh—H$_2$L, Rh-Me$_2$L or Rh-BINAP. At 1 mol % catalyst loadings, 1.Rh afforded the conjugate addition products (4) in nearly quantitative conversions with 80-99% isolated yields. See Table 3, Entries 1-3. Under the same conditions, neither the Rh-Me$_2$L nor Rh-H$_2$L control gave appreciable amounts of products due to their insolubility in the reaction solvents, whereas the Rh-BINAP homogeneous control gave modest isolated yields of 29-46%. See Table 3, Entries 6-8. 3 mol % of the Rh-BINAP catalyst was needed to afford the addition products in comparable yields (Table 3, Entries 9-11) to those produced by 1 mol % of 1.Rh. The e.e.'s of the conjugate addition products (99% or higher) are similar between 1.Rh and the homogeneous control, but the activity of 1.Rh is approximately 3 times as high as that of the homogeneous control. Without being bound to any one theory, it is believed that site isolation of the active catalysts in 1.Rh is responsible for its higher catalytic activity, by preventing any intermolecular catalyst deactivation pathways.

TABLE 3

Asymmetric additions of arylboronic acids to 2-cyclohexenone by 1•Rh and homogeneous catalysts$^a$

| entry | Ar | catalyst | catalyst % loading | Isolated yield | e.e. %$^b$ |
|---|---|---|---|---|---|
| 1 | Ph | 1•Rh | 1 mol % | 80% | >99 |
| 2 | m- | 1•Rh | 1 mol % | 85% | 99 |
| 3 | p-MeC(O)— | 1•Rh | 1 mol % | 99% | 99 |
| 4 | Ph | Rh—H$_2$L$^c$ | 3 mol % | 0% | N/A |
| 5 | Ph | Rh—Me$_2$L$^c$ | 3 mol % | 7%$^d$ | N/A |
| 6 | Ph | Rh-BINAP | 1 mol % | 29% | >99 |
| 7 | m- | Rh-BINAP | 1 mol % | 34% | >99 |
| 8 | p-MeC(O)— | Rh-BINAP | 1 mol % | 46% | >99 |
| 9 | Ph | Rh-BINAP | 3 mol % | 85% | >99 |
| 10 | m- | Rh-BINAP | 3 mol % | 87% | >99 |
| 11 | p-MeC(O)— | Rh-BINAP | 3 mol % | 87% | 99 |

$^a$Reaction conditions: 2 (1 equiv.), 3 (3 equiv.), NEt$_3$ (1 equiv.), catalyst (1 or 3 mol % Rh), 1,4-dioxane (0.04M), H$_2$O (0.04M) at 40° C. for 20 h.
$^b$Determined by chiral HPLC.
$^c$The Rh—H$_2$L and Rh—Me$_2$L complexes are insoluble in the reaction solvents.
$^d$Yield determined by NMR integration.

Example 12

Catalysis of Asymmetric 1,2-Addition of AlMe$_3$ to 2-Cyclohexenone and 2-Cycloheptenone Exemplary Procedure for 1.Rh Catalyzed Asymmetric 1,2-Addition of AlMe$_3$ to 2-Cyclohexenone and 2-Cycloheptenone:

MOF 1 (4.3 mg, 1.4 μmol) was metalated with Rh(nbd)$_2$BF$_4$ (56 μL, 1.4 μmol, 0.025M solution in CH$_2$Cl$_2$) as described above. To a suspension of 1.Rh (1.4 μmol) and THF (2.8 mL) was added 2-cyclohexeone (11 μL, 0.11 mmol) and AlMe$_3$ (89 μL, 0.18 mmol, 2.0 M solution in toluene) under nitrogen atmosphere at r.t. After the reaction was stirred at r.t. for 24 h, the solid catalyst was separated via centrifugation. Aqueous NH$_4$Cl was added to the supernatant at 0° C. and the mixture was extracted with Et$_2$O. The combined organic extract was dried over MgSO$_4$, filtered, and concentrated on a rotary evaporator. The residue was analyzed by Chiral GC and subjected to flash column chromatography (silica gel, CH$_2$Cl$_2$/Et$_2$O=20/1) to give (S)-1-methylcyclohex-2-enol (9.4 mg, 0.084 mmol, 71% yield). $^1$H NMR (CDCl$_3$) δ 1.28 (s, 3H), 1.56-1.80 (m, 5H), 1.88-1.98 (m, 1H), 1.98-2.08 (m, 1H), 5.63 (d, J=10.0 Hz, 1H), 5.75 (d, J=10.0, 3.6 Hz, 1H).

(S)-1-Methylcyclohept-2-enol $^1$H NMR (CDCl$_3$) δ 1.33 (s, 3H), 1.50-1.90 (m, 6H), 2.05-2.23 (m, 2H), 5.60-5.70 (m, 2H).

Exemplary Procedure for Rh-Me$_2$L Catalyzed Asymmetric 1,2-Additions of AlMe$_3$ to 2-Cyclohexenone:

A mixture of [Rh(nbd)$_2$]BF$_4$ (1.1 mg, 2.9 μmol) and Me$_2$L (3.1 mg, 3.3 μmol) in CH$_2$Cl$_2$ (2.0 mL) was stirred at room temperature for 3 h. After evaporation of the solvent, THF (18.8 mL) was added to the residue. To a solution was added 2-cyclohexeone (73 μL, 0.75 mmol) and AlMe$_3$ (563 μL, 1.13 mmol, 2.0 M solution in toluene) under nitrogen atmosphere at r.t. After the reaction was stirred at the same temperature for 24 h, aqueous NH$_4$Cl was added to the solution at 0° C. and the mixture was extracted with Et$_2$O. The combined organic extract was dried over MgSO$_4$, filtered, and concentrated on a rotary evaporator. The residue was analyzed by Chiral GC and subjected to flash column chromatography (silica gel, $CH_2Cl_2/Et_2O=20/1$) to give (S)-1-methylcyclohex-2-enol (39.0 mg, 0.345 mmol, 46% yield).

Discussion:

As shown in Scheme 15, the asymmetric addition of $AlMe_3$ to an α,β-unsaturated ketone, 5, provides a chiral allylic alcohol, 6.

Scheme 15. Asymmetric Addition of $AlMe_3$ to an α,β-Unsaturated Ketone

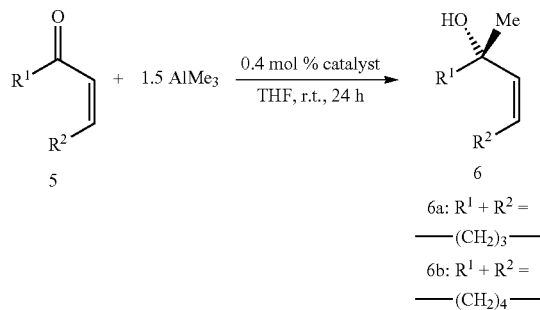

6a: $R^1 + R^2 = $ —$(CH_2)_3$—

6b: $R^1 + R^2 = $ —$(CH_2)_4$—

Table 4 below shows the results of additions of $AlMe_3$ to α,β-unsaturated ketones catalyzed by 1.Rh or by homogenous control catalyst $Rh-Me_2L$. At 0.4 mol % catalyst loadings, 1.Rh afforded allylic alcohols in nearly quantitative conversions and with 71% and 68% isolated yields for 6a and 6b, respectively. At the same catalyst loadings, the conversions and yields observed for 1.Rh are higher than those for the $Rh-Me_2L$ homogeneous control. The e.e.'s seen for 1.Rh are comparable to those for the $Rh-Me_2L$ homogeneous control.

TABLE 4

Asymmetric $AlMe_3$ Additions to α,β-Unsaturated Ketones Catalyzed by 1·Rh and Homogenous Control Catalyst.

| Entry | substrat | Catalyst | conv. %[a] | e.e. %[a] | Isolated yield[b] |
|---|---|---|---|---|---|
| 1 | O cyclohexenone | 1·Rh | 97 | 98 | 71% |
| 2 | | Rh—Me$_2$L | 82 | >99 | 46% |
| 3 | O cycloheptenone | 1·Rh | 97 | 98 | 68% |
| 4 | | Rh—Me$_2$L | 91 | >99 | <40% |

[a]Determined by GC.
[b]Isolated yields are much lower due to the relatively low boiling points of the allylic alcohols 6.

Example 13

"Heterogeneity" of 1.Rh

Studies were carried out to demonstrate the "heterogeneous" nature of 1.Rh. First, the PXRD of 1.Rh recovered from the reaction between $AlMe_3$ and 2-cyclohexenone remained the same as those of freshly prepared 1 and 1.Rh. See FIG. 4B. Second, at a 0.4 mol % catalyst loading, the 1.Rh catalyst could be recovered and reused for $AlMe_3$ addition to 2-cyclohexenone with only minor decrease in conversions and enantioselectivities. The conversions/e.e.'s for three consecutive runs (with recovered 1.Rh) are 96%/99%, 95%/98%, 87%/96%, respectively. Third, the amount of Rh and Zr leaching into the supernatant during the $AlMe_3$ addition reaction to 5 is less than 0.4% and 1.0% as determined by ICP-MS. Furthermore, the amount of Rh and Zr leaching into the supernatant during the phenylboronic acid addition reaction to 2 is less than 0.9% and 0.2% as determined by ICP-MS. Finally, 1.Rh recovered from the reaction between 2 and m-methylcarboxy-phenylboronic acid (85% isolated yield, 99% e.e.) could be reused to catalyze the addition of p-acetylphenyl boronic acid (65% isolated yield, 99% e.e.), whereas the removal of 1.Rh one hour after the reaction between 2 and m-methylcarboxy-phenylboronic acid completely stopped the reaction. Thus, it appears that 1.Rh is a recoverable and reusable, enantioselective single-site solid catalyst.

Example 14

Catalysis of Asymmetric Hydrogenation of β-Keto Esters

Exemplary Procedure for 1.Ru-Catalyzed Asymmetric Hydrogenation of β-Keto Esters:

MOF 1 (2.5 mg, 0.83 μmol) was metalated with Ru(cod)(2-methyl-allyl)$_2$ (1.3 mg, 4.1 μmol). A mixture of methyl acetoacetate (8.9 μL, 0.085 mmol), 1.Ru (0.83 μmol), and MeOH (2.5 mL) was loaded into a Parr pressure reactor in a nitrogen-filled glovebox. The reactor was then pressurized to 40 bar. After stirring at room temperature for 16 h, the mixture was passed through a 0.22 μm PTFE syringe filter. The sample was then analyzed by chiral GC for yield and enantioselectivity.

Exemplary Procedure for [Ru(Me$_2$L) (DMF)$_2$Cl$_2$] Catalyzed Asymmetric Hydrogenation of β-Keto Esters:

A mixture of methyl acetoacetate (21.6 μL, 0.200 mmol), [Ru(Me$_2$L)Cl$_2$(DMF)$_2$] (1.3 mg, 1.0 μmol), and MeOH (5.9 mL) was loaded into a Parr pressure reactor in a nitrogen-filled glovebox. The reactor was then pressurized to 40 bar. After stirring at room temperature for 16 h, the mixture was passed through a 0.22 μm PTFE syringe filter. The sample was then analyzed by chiral GC for yield and enantioselectivity.

Asymmetric Hydrogenation with 1.Ru Prepared by a Modified Metalation Method:

Freshly prepared MOF 1 (2.7 mg, 0.89 μmol) was weighed onto a filter paper and then charged into a 1 dram vial. Methanol was then added followed by Ru(cod)(2-methyl-allyl)$_2$ (0.28 mg, 0.89 μmol). The vials were sealed with a rubber septum and then degassed by repeated vacuum/N$_2$ cycles. HBr (25 μL, 7.1 μmol, 0.29 M solution in MeOH) was added to the solution and the solution degassed further. The now orange solution was then stirred for 16 h under N$_2$. The MOF was centrifuged out of suspension and washed with CH$_2$Cl$_2$ and then MeOH. A mixture of MOF, tert-butyl acetoacetate (14.8 μL, 0.0892 mmol) and EtOH (3.0 mL) was loaded into a Parr pressure reactor in a nitrogen-filled glovebox. The reactor was then pressurized to 40 bar. After stirring at room temperature for 16 h, the mixture was passed through a 0.22 μm PTFE syringe filter. The yield and enantioselectivity were determined by chiral GC (51% yield, 98% ee).

Discussion:

The hydrogenation of a β-keto ester, 7, to chiral alcohol, 8, is shown in Scheme 16.

Scheme 16. Hydrogenation of β-Keto Esters.

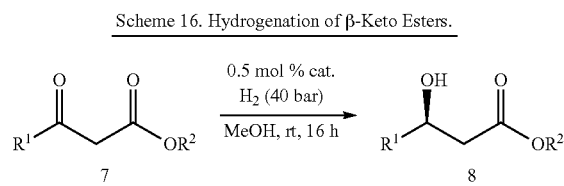

As indicated below, in Table 5, under an atmosphere of $H_2$ at 40 bar, 1.Ru converted methyl acetoacetate to the corresponding alcohol in a quantitative yield with e.e.'s as high as 94%. By varying the post-synthetic metalation conditions, e.e.'s as high as 98% could be obtained for the hydrogenation of t-butyl acetoacetate, albeit in lower yields (51%). 1.Ru is active in hydrogenating a broad range of β-keto esters, but the e.e.'s of the hydrogenation products are 5-6% lower than those obtained using $RU(Me_2L)_2(DMF)_2Cl_2$.

TABLE 5

Asymmetric hydrogenation of β-keto esters by 1•Ru and $Ru(Me_2L)(DMF)_2Cl_2$

| Entry | $R^1$ | $R^2$ | Catalyst | Yield[a] | ee %[a] |
|---|---|---|---|---|---|
| 1 | Me | Me | 1•Ru | quantitative | 93 |
| 2 | Et | Et | 1•Ru | quantitative | 94 |
| 3 | Me | $^tBu$ | 1•Ru | quantitative | 93 |
| 4 | Me | Me | $Ru(Me_2L)(DMF)_2Cl_2$ | quantitative | >99 |
| 5 | Et | Et | $Ru(Me_2L)(DMF)_2Cl_2$ | quantitative | >99 |
| 6 | Me | $^tBu$ | $Ru(Me_2L)(DMF)_2Cl_2$ | quantitative | >99 |

[a]Determined by GC.

Example 15

Catalysis of Asymmetric Hydrogenation of Substituted Alkenes

Exemplary Procedure for 1.Ru-Catalyzed Asymmetric Hydrogenation of Substituted Alkenes:

MOF 1 (2.7 mg, 0.89 µmol) was metalated with Ru(cod)(2-methyl-allyl)$_2$ (1.4 mg, 4.4 µmol). A mixture of dimethyl itaconate (14.1 mg, 0.0892 mmol), 1.Ru (0.89 µmol), and EtOH (3.0 mL) was loaded into a Parr pressure reactor in a nitrogen-filled glovebox. The reactor was then pressurized to 4 bar. After stirring at room temperature for 16 h, the mixture was passed through a 0.22 µm PTFE syringe filter. The sample was then analyzed by chiral GC for yield and enantioselectivity.

Exemplary Procedure for [$Ru(Me_2L)(DMF)_2Cl_2$] Catalyzed Asymmetric Hydrogenation of Substituted Alkenes:

A mixture of dimethyl itaconate (31.6 mg, 0.2 mmol), [$Ru(Me_2L)(DMF)_2Cl_2$] (1.3 mg, 1 µmol), and EtOH (6.7 mL) was loaded into a Parr pressure reactor in a nitrogen-filled glovebox. The reactor was then pressurized to 4 bar. After stirring at room temperature for 16 h, the mixture was passed through a 0.22 µm PTFE syringe filter. The sample was then analyzed by chiral GC for yield and enantioselectivity.

Supernatant of 1.Ru:

MOF 1 (2.6 mg, 0.86 µmol) was metalated with Ru(cod)(2-methyl-allyl)$_2$ (1.3 mg, 4.2 µmol). A mixture of dimethyl itaconate (12.1 µL, 0.0859 mmol), 1.Ru (0.86 µmol), and EtOH (2.9 mL) was loaded into a Parr pressure reactor in a nitrogen-filled glovebox. The reactor was then pressurized to 4 bar. After stirring at room temperature for 1 h, the MOF was filtered out of the reaction, and the supernatant was placed under a pressure of 4 bar and allowed to react overnight. The supernatant was analyzed for yield of the hydrogenated product both promptly after filtration and after stirring for one night under $H_2$.

Discussion:

The hydrogenation of a substituted alkene, 9, to provide a chiral alkene, 10, is shown below in Scheme 17.

Scheme 17. Hydrogenation of Substituted Alkenes.

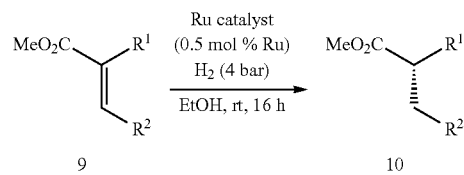

1.Ru catalyzed the hydrogenation of substituted alkenes at low pressures and room temperature. See Table 6, below. 0.5 mol % of 1.Ru catalyzed the hydrogenation of 8a-8c to afford 9a-9c in quantitative yields and 70-91% e.e.'s. As with the hydrogenation of β-keto esters, the e.e.'s of 9a-9c are 3-11% lower for the 1.Ru catalyzed reactions when compared to those catalyzed by $Ru(Me_2L)(DMF)_2Cl_2$. Without being bound to any one theory, it is believed that a small amount of achiral Ru complex might be trapped in the MOF channel, contributing to the racemic background reaction. Consistent with this, inductively coupled plasma-optical emission spectroscopy (ICP-OES) showed the leaching of 3.6% Ru but only 0.1% Zr from the substituted alkene (methyl 2-acetamidoacrylate) hydrogenation reaction. The much lower Zr concentration in the supernatant suggests that the Ru present in solution is more likely the result of either trapped achiral Ru complexes, such as Ru(cod)(2-methyl allyl)$_2$, or the Ru species dissociating from the L ligand, but not from dissolution of the MOF. This small amount of achiral Ru complex would have been below the sensitivity of the XAFS technique. Several tests also demonstrated the "heterogeneous" nature and the ability to reuse 1.Ru in asymmetric hydrogenation reactions.

TABLE 6

Asymmetric hydrogenation of substituted alkenes by 1•Ru and $Ru(Me_2L)(DMF)_2Cl_2$.

| Entry | $R^1$ | $R^2$ | catalyst | Yield[a] | ee %[a] |
|---|---|---|---|---|---|
| 1 | NHAc | H | 1•Ru | quant. | 85 |
| 2[b] | NHAc | Ph | 1•Ru | quant. | 70 |
| 3 | $CH_2CO_2$ | H | 1•Ru | quant. | 91 |
| 4 | NHAc | H | $Ru(Me_2L)(DMF$ | quant. | 88 |
| 5 | NHAc | Ph | $Ru(Me_2L)(DMF$ | quant. | 81 |
| 6 | $CH_2CO_2$ | H | $Ru(Me_2L)(DMF$ | quant. | 96 |

[a]Determined by GC.
[b]$H_2$ (40 bar)

Example 16

Catalysis of Asymmetric Reductive Cyclization of 1,6-Enynes

Figure 6:
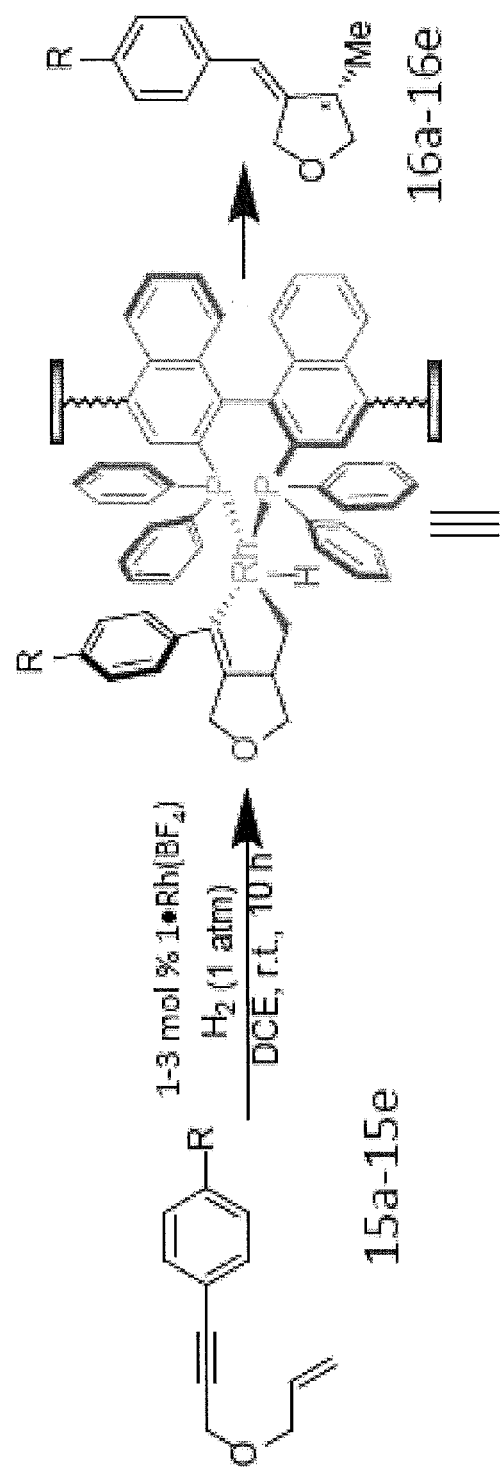
FIG. 6 is a drawing showing the use of an exemplary metal-organic framework (MOF) catalyst comprising a chiral phosphine organic bridging ligand in the asymmetric catalysis of the reductive cyclization of 1,6 enynes 15a-15e.

FIG. 6 shows the use of MOF 1 in catalysis of the reductive cyclization reactions of various 1,6-enynes, i.e., 1-(3-allyoxy)prop-1-yn-1-yl)-4-(methyl)benzene (15a), 1-(3-allyoxy)prop-1-yn-1-yl)benzene (15b), 1-(3-allyoxy)prop-1-yn-1-yl)-4-(methyoxy)benzene (15c), 1-(3-(allyloxy)prop-1-yn-1-yl)-4-(tert-butyl)benzene (15d); and 1-(3-(allyloxy)prop-1-yn-1-yl)-4-(trifluoromethyl)benzene (15e). 15a-15c and 15e were prepared according to, or analogously to, previously reported literature procedures. 15d was prepared as shown in Scheme 18, below.

Scheme 18. Preparation of
1-(3-(allyloxy)prop-1-yn-1-yl)-4-(tert-butyl)benzene (15d).

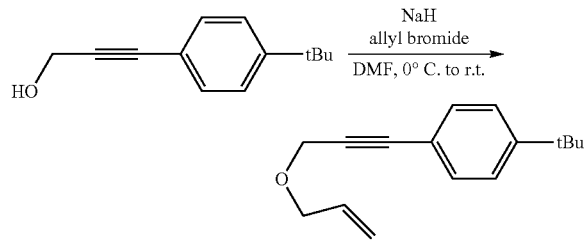

More particularly, to a cooled (0° C.) solution of 1-(2'-hydroxypropinyl)-4-tert-butylbenzene (500 mg, 2.66 mmol; see Kusaka et al., Chem. Asian J., 2013, 8, 723)) in N,N-dimethylformamide (DMF, 20 mL) was slowly added sodium hydride (60% dispersion in oil, 0.150 g, 3.45 mmol), which resulted in the evolution of hydrogen gas. The reaction mixture was stirred at 0° C. for 20 min and then allyl bromide (0.22 mL, 2.66 mmol) was added. The resulting mixture was warmed to room temperature and stirred overnight. The reaction was carefully quenched by the dropwise addition of water (5 mL) followed by saturated aqueous ammonium chloride (20 mL). The resulting mixture was extracted with $Et_2O$ (3×25 mL). The combined organic layers were dried with $Na_2SO_4$ and concentrated via rotovap. Flash chromatography (10:90 EtOAc:hexanes) gave 15d as a colorless oil (422 mg, 70%). $^1$H NMR (500 MHz, $CDCl_3$): δ 1.31 (s, 9H), 4.14 (app dt, J=5.8, 1.3 Hz, 2H), 4.38 (s, 2H), 5.21-5.27 (m, 1H), 5.35 (app dq, J=17.3, 1.3 Hz, 1H), 5.96 (ddt, J=17.3, 10.3, 5.8 Hz, 1H), 7.33 (d, J=8.3 Hz, 2H), 7.39 (d, J=8.3 Hz, 2H). $^{13}$C NMR (125 MHz, $CDCl_3$): δ 31.14, 34.74, 57.97, 70.61, 84.28, 86.36, 117.86, 119.60, 125.26, 131.48, 134.10, 151.67. ESI-MS: calcd for $C_{16}H_{21}O$ $[M+H]^+$ 229.2. found 229.2.

Exemplary Procedure for MOF 1 Catalyzed Asymmetric Reductive Cyclization Reactions:

MOF 1 (7.4 mg, 2.4 μmol) was metalated with $[Rh(nbd)_2]BF_4$ (98 μL, 2.4 μmol, 0.025 M solution in $CH_2Cl_2$) as described above in Example 7. A mixture of 1,6-enyne 15a (5.0 mg, 0.027 mmol) and 1.Rh (0.80 μmol Rh) in 1,2-dichloroethane (2.8 mL) was stirred under hydrogen atmosphere at rt for 10 h. 1.Rh was removed from the solution by centrifugation. The supernatant was transferred to a clean round-bottom flask, and the MOF was washed further with $CH_2Cl_2$. The combined organic extracts were concentrated on a rotary evaporator. The residue was subjected to preparative TLC (silica gel, hexane/ethyl acetate=5/1) to give 16a (95% NMR yield, 95% ee).

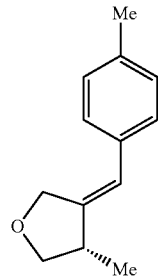 [SMILES: Cc1ccc(/C=C2\COC[C@H]2C)cc1]

16a (95% NMR yield, 95% ee): $^1$H NMR (500 MHz, $CDCl_3$): δ 1.21 (d, J=7.0 Hz, 3H), 2.34 (s, 3H), 2.84-2.96 (m, 1H), 3.38 (app t, J=8.0 Hz, 1H), 4.07 (app t, J=8.0 Hz, 1H), 4.61 (app dt, J=14.0, 2.1 Hz, 1H), 4.69 (dd, J=14.0, 1.0 Hz, 1H), 6.24-6.28 (m, 1H), 7.04 (d, J=8.0 Hz, 2H), 7.15 (d, J=8.0 Hz, 2H). $^{13}$C NMR (125 MHz, $CDCl_3$): δ 16.41, 21.10, 39.74, 70.29, 74.32, 119.70, 127.78, 129.18, 134.60, 136.21, 145.38. ESI-MS: calcd for $C_{13}H_{17}O$ $[M+H]^+$ 189.1. found 189.1. The ee was measured by HPLC (Chiralpak IA, 0.5 mL/min, hexanes/2-propanol=99/1, 255 nm, $t_1$=14.0 min (minor), $t_2$=15.1 min (major)).

16b-16e were prepared via analogous reactions using 15b-e as the substrate. Catalysis results are described below in Table 7.

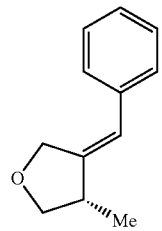 [SMILES: C[C@@H]1COC/C1=C\c1ccccc1]

16b (89% NMR yield, 96% ee): $^1$H NMR (500 MHz, $CDCl_3$): δ 1.23 (d, J=6.5 Hz, 3H), 2.86-2.97 (m, 1H), 3.39 (app t, J=7.8 Hz, 1H), 4.08 (app t, J=7.8 Hz 1H), 4.63 (d, J=14.3 Hz, 1H), 4.71 (d, J=14.3 Hz, 1H), 6.28-6.32 (m, 1H), 7.15 (d, J=7.8 Hz, 2H), 7.21 (t, J=7.8 Hz, 1H), 7.35 (t, J=7.8 Hz, 2H). The ee was measured by HPLC (Chiralcel OD-H, 0.6 mL/min, hexanes/2-propanol=500/1, 250 nm, $t_1$=27.3 min (major), $t_2$=29.1 min (minor)).

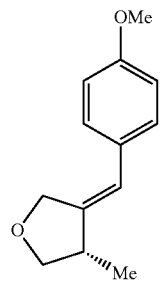 [SMILES: COc1ccc(/C=C2\COC[C@H]2C)cc1]

16c (87% NMR yield, 95% ee): $^1$H NMR (500 MHz, $CDCl_3$): δ 1.21 (d, J=7.0 Hz, 3H), 2.82-2.95 (m, 1H), 3.37 (app t, J=7.8 Hz, 1H), 3.81 (s, 3H), 4.07 (app t, J=7.8 Hz, 1H), 4.60 (d, J=14.0 Hz, 1H), 4.67 (d, J=14.0 Hz, 1H), 6.20-6.26 (m, 1H), 6.88 (d, J=8.8 Hz, 2H), 7.08 (d, J=8.8 Hz, 2H). The ee was measured by HPLC (Chiralcel OD-H, hexanes/2-propanol=99/1, 0.3 mL/min, 260 nm, $t_1$=34.1 min (minor), $t_2$=39.0 min (major)).

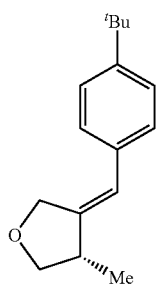

16d (82% NMR yield, 94% ee): $^1$H NMR (500 MHz, CDCl$_3$): δ 1.21 (d, J=6.5 Hz, 3H), 1.32 (s, 9H), 2.85-2.96 (m, 1H), 3.38 (app t, J=7.9 Hz, 1H), 4.07 (app t, J=7.9 Hz, 1H), 4.63 (app dt, J=14.0, 2.1 Hz, 1H), 4.71 (dd, J=14.0, 1.0 Hz, 1H), 6.25-6.30 (m, 1H), 7.09 (d, J=8.3 Hz, 2H), 7.37 (d, J=8.3 Hz, 2H). $^{13}$C NMR (125 MHz, CDCl$_3$): δ 16.47, 31.25, 34.48, 39.77, 70.33, 74.32, 119.57, 125.41, 127.61, 134.60, 145.60, 149.45. ESI-MS: calcd for $C_{16}H_{23}O$ [M+H]$^+$ 231.2. found 231.1. The ee was measured by HPLC (Chiralcel OJ, hexanes/2-propanol=97/3, 0.6 mL/min, 259 nm, $t_1$=12.1 min (minor), $t_2$=15.7 min (major)).

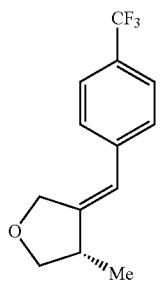

16e (70% NMR yield, 94% ee): $^1$H NMR (500 MHz, CDCl$_3$): δ 1.23 (d, J=7.0 Hz, 3H), 2.87-3.00 (m, 1H), 3.41 (app t, J=8.0 Hz, 1H), 4.10 (app t, J=8.0 Hz, 1H), 4.61 (d, J=14.5 Hz, 1H), 4.69 (d, J=14.5 Hz, 1H), 6.29-6.35 (m, 1H), 7.23 (d, J=8.3 Hz, 2H), 7.58 (d, J=8.3 Hz, 2H). $^{13}$C NMR (125 MHz, CDCl$_3$): 16.34, 40.03, 70.23, 74.27, 118.86, 124.18 (q, J=267.7 Hz), 125.42 (q, J=3.8 Hz), 127.96, 128.30 (q, J=32.3 Hz), 140.83 (q, J=1.4 Hz), 149.60. ESI-MS: calcd for $C_{13}H_{14}F_3O$ [M+H]$^+$ 243.1. found 243.1. The ee was measured by HPLC (Chiralcel OD-H, hexanes/2-propanol=99/1, 0.3 mL/min, 260 nm, $t_1$=21.0 min (major), $t_2$=22.3 min (minor)).

TABLE 7

Asymmetric Reductive Cyclization of 1,6-Enynes with MOF 1.

| entry | catalyst | R | Rh-loading (mol %) | yield (%)[b] | ee (%)[c] |
|---|---|---|---|---|---|
| 1 | 1·Rh(BF$_4$) | Me (15a) | 1 | 68 | 94 |
| 2[d] | Rh(Me$_2$L)BF$_4$ | Me (15a) | 1 | 10 | 91 |
| 3 | 1·Rh(BF$_4$) | Me (15a) | 3 | 95 | 95 |
| 4 | 1·Rh(BF$_4$) | H (15b) | 3 | 89 | 96 |
| 5 | 1·Rh(BF$_4$) | OMe (15c) | 3 | 87 | 95 |
| 6 | 1·Rh(BF$_4$) | $^t$Bu (15d) | 3 | 82 | 99 |
| 7 | 1·Rh(BF$_4$) | CF$_3$ (15e) | 3 | 70 | 94 |

[a]Reaction conditions: 15 (1 equiv.), catalyst, H$_2$ (1 atm) at r.t. for 10 h.
[b]Determined by $^1$H NMR integration with internal standard.
[c]Determined by chiral HPLC.
[d]Catalyst was generated in situ.

Figure 8:
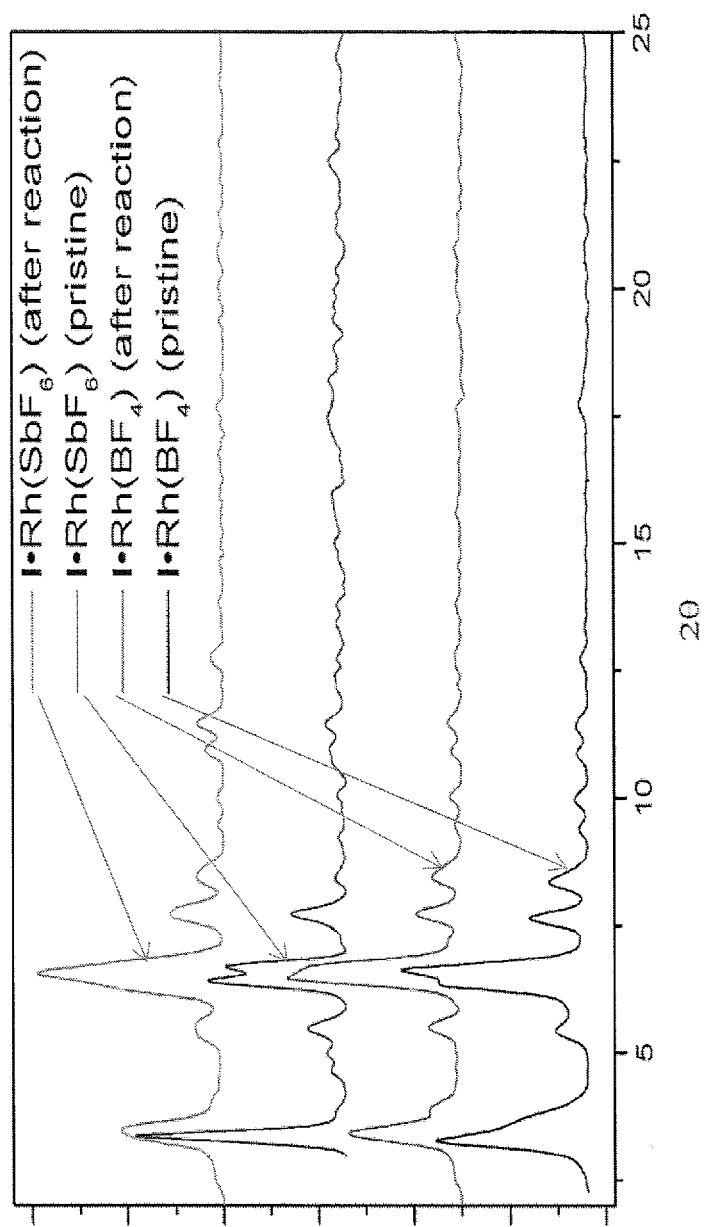
FIG. 8 is a graph showing the powder x-ray diffraction (PXRD) patterns of a freshly prepared metal-organic framework (MOF) containing a (2,2'-bis(diphenylphosphino)-1,1-binaphthyl) (BINAP)-based organic bridging ligand and zirconium oxoclusters (i.e., MOF 1), metalated with rhodium tetrafluoroboron, i.e., 1.Rh(BF$_4$) (bottom pattern); 1.Rh(BF$_4$) recovered from reductive cyclization reactions (pattern second from bottom); freshly prepared MOF 1 metalated with rhodium hexafluoroantimony, i.e., 1.Rh(SbF$_6$) (pattern third from bottom); and 1.Rh(SbF$_6$) recovered from Alder-Ene cyclization reactions (top pattern).

At 1 mol % 1·Rh(BF$_4$) loading (based on Rh), 1,6-enyne 15a was converted to monoalkylidene furan 16a in 68% yield and 94% ee in a H$_2$ atmosphere at r. t. See Table 7, entry 1). Without being bound to any one theory, it is believed that this cyclization reaction proceeded through the rhodacycle shown in FIG. 6 and as proposed by Krische and coworkers. See Jang et al., J. Am. Chem. Soc., 2004, 126, 7875; and Jang et al., J. Am. Chem. Soc., 2005, 127, 6174. Under similar conditions, the homogeneous control Rh(Me$_2$L)BF$_4$ was significantly less active, affording the cyclized product in only 10% yield and 91% ee. See Table 7, entry 2. Without being bound to any one theory, the enhanced catalytic activity of 1·Rh(BF$_4$) over Rh(Me$_2$L)BF$_4$ (by ~7 times) is likely due to the prevention of multimolecular catalyst deactivation via catalytic site isolation. At 3 mol % loading of 1·Rh(BF$_4$), 16a was obtained in nearly quantitative yield and 95% ee. See Table 7, entry 3. 1·Rh(BF$_4$) was also recyclable. See FIG. 8.

The scope of 1,6-enynes in the 1·Rh(BF$_4$)-catalyzed reductive cyclization reactions was also studied. 3 mol % of 1·Rh(BF$_4$) catalyzed cyclization of the un-substituted 1,6-enyne 15b afforded monoalkylidene furan 16b in 89% yield and 96% ee. See Table 7, entry 4. 1,6-enynes bearing either electron-donating groups or bulky substituents formed cyclic products in high ee's and good yields. See Table 7, entries 5 and 6. The highest ee of 99% was observed for the cyclized product 16d that bears the bulky tert-butyl group. Electron-withdrawing groups have a slightly deleterious effect on yields due to formation of undesired byproducts; fortunately, the ee remains high for the cyclized product. See Table 7, entry 7.

Example 17

Catalysis of Asymmetric Alder-Ene Cyclizations

Figure 7:
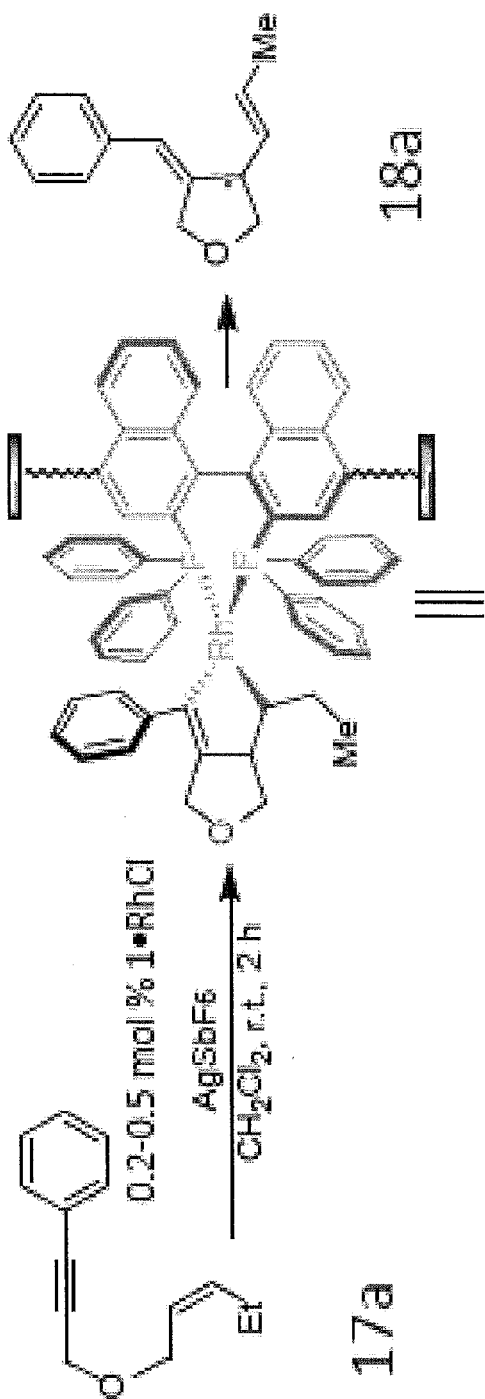

FIG. 7 shows the use of MOF 1 in the catalysis of the asymmetric Alder-Ene cyclization reactions of (Z)-(3-pent-2-en-1-yloxy)prop-1-yn-1-yl)benzene(17a). MOF 1 was also used in the asymmetric Alder-Ene cyclization reactions of (Z)-1-(methyl)-4-(3-(pent-2-en-1-yloxy)prop-1-yn-1-yl)benzene 1-(3-allyoxy)prop-1-yn-1-yl)benzene (17b), (Z)-1-(methoxy)-4-(3-(pent-2-en-1-yloxy)prop-1-yn-1-yl)benzene (17c), (Z)-1-(tert-butyl)-4-(3-(pent-2-en-1-yloxy)prop-1-yn-1-yl)benzene (17d); and (Z)-1-(trifluoromethyl)-4-(3-(pent-2-en-1-yloxy)prop-1-yn-1-yl)benzene (17e). 17a-17c and 17e were prepared according to, or analogously to, previously reported literature procedures. 17d was prepared as shown in Scheme 19, below.

Scheme 19. Preparation of (Z)-1-(tert-butyl)-4-(3-(pent-2-en-1-yloxy)prop-1-yn-1-yl)benzene (17d).

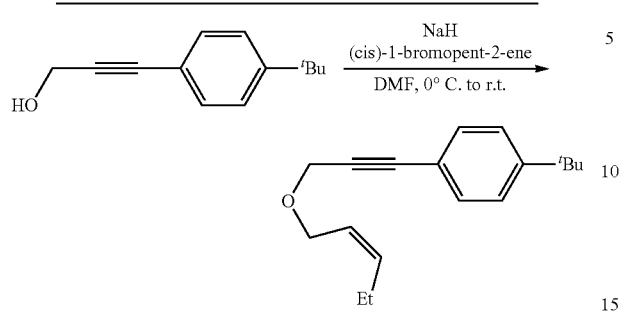

To a cooled (0° C.) solution of 1-(2'-hydroxypropinyl)-4-tert-butylbenzene (500 mg, 2.66 mmol; see Kusaka et al., Chem. Asian J., 2013, 8, 723) in N,N-dimethylformamide (DMF, 20 mL) was slowly added sodium hydride (60% in oil suspension, 0.150 g, 3.45 mmol), resulting in the evolution of hydrogen gas. The reaction mixture was stirred (10 min, 0° C.), and then (cis)-1-bromo-pent-2-ene (395 mg, 2.66 mmol) was added. The resulting mixture was warmed to room temperature and stirred overnight. The reaction was carefully quenched by the dropwise addition of water (5 mL) followed by saturated aqueous ammonium chloride (20 mL). The resulting mixture was extracted with $Et_2O$ (3×25 mL). The combined organic layers were dried with $Na_2SO_4$ and concentrated via rotovap. Flash chromatography on silica gel (10:90 EtOAc:hexanes) gave 17d as a colorless oil (380 mg, 56%). $^1$H NMR (500 MHz, $CDCl_3$): δ 1.00 (t, J=7.5 Hz, 3H), 1.31 (s, 9H), 2.11-2.17 (m, 2H), 4.20 (d, J=7.0 Hz, 2H), 5.51-5.56 (m, 1H), 5.63-5.68 (m, 1H), 7.33 (d, J=8.0 Hz, 2H), 7.39 (d, J=8.0 Hz, 2H). $^{13}$C NMR (125 MHz, $CDCl_3$): δ 14.26, 20.95, 31.18, 34.78, 57.70, 64.90, 84.54, 86.24, 119.71, 124.59, 125.30, 131.50, 136.48, 151.66. ESI-MS: calcd for $C_{18}H_{25}O$ [M+H]$^+$ 257.2. found 257.2.

Post-synthetic metalation of MOF 1 with [Rh(nbd)Cl]$_2$:

Freshly prepared MOF 1 (3.0 mg, 0.99 μmol) was weighed onto a filter paper in a nitrogen-filled glovebox and then charged into a 1 dram vial. After addition of THF (2.0 mL) and [RhCl(nbd)]$_2$ (19.9 μL, 0.50 μmol, 0.025 M solution in THF), the mixture was allowed to stand overnight, and then the metalated MOF was centrifuged out of suspension and washed with THF once then $CH_2Cl_2$ three times. ICP-MS analysis determined 18 mol % Rh-loading of $H_2L$.

Exemplary Procedure for 1.Rh Catalyzed Asymmetric Alder-Ene Reaction:

BINAP-MOF (3.0 mg, 0.99 μmol) was metalated with [Rh(nbd)Cl]$_2$ (19.9 μL, 0.50 μmol, 0.025M solution in THF) as described above. 1.Rh (0.18 μmol based on Rh suspended in 0.56 mL $CH_2Cl_2$) was added 1,6-enyne 17a (17.9 mg, 89.4 μmol) and $AgSbF_6$ (397 μL, 9.91 μmol, 0.025 M solution in THF). The reaction mixture was stirred under a nitrogen atmosphere at room temperature for 2 hours. 1.Rh was removed from the solution by centrifugation. The supernatant was transferred to a clean round-bottom flask, and the MOF was washed further with $CH_2Cl_2$ (3×1 mL). The combined organic extracts were concentrated in vacuo. The residue was purified by preparative TLC (5:95 EtOAc: hexanes) to afford cycloisomerized product 18a as a colorless oil (99% NMR yield).

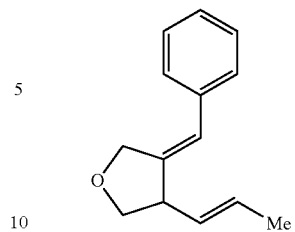

18a (99% yield, 99% ee): $^1$H NMR (500 MHz, $CDCl_3$): δ 1.76 (dd, J=6.5, 1.5 Hz, 3H), 3.41-3.49 (m, 2H), 4.08 (t, J=7 Hz, 1H), 4.58-4.59 (m, 1H), 4.72-4.75 (m, 1H), 5.31-5.36 (m, 1H), 5.65 (dq, J=15.0 Hz, 6.5 Hz), 6.23-6.24 (m, 1H), 7.14 (d, J=7.5 Hz, 2H), 7.21 (t, J=7.5 Hz, 1H), 7.33 (t, J=7.5 Hz, 2H). The ee was measured by HPLC (Chiralcel OJ, hexanes/2-propanol=99/1, 0.3 mL/min, 256 nm, $t_1$=24.1 min (major), $t_2$=25.9 min (minor)).

18b-18e were prepared via analogous reactions using 17b-e as the substrate. Catalysis results are described below in Tables 8 and 9.

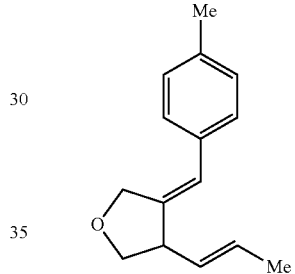

18b (99% yield, 99% ee): $^1$H NMR (500 MHz, $CDCl_3$): δ 1.76 (dd, J=6.5, 1.5 Hz, 3H), 2.34 (s, 3H), 3.49-3.42 (m, 2H), 4.07 (t, J=7.5 Hz, 1H), 4.39-4.36 (m, 1H), 4.73-4.70 (m, 1H), 6.21 (m, 1H), 7.04 (d, J=8.0 Hz, 2H), 7.15 (d, J=8.0 Hz, 2H). The ee was measured by HPLC (Chiralcel OJ, hexanes/2-propanol=99/1, 0.3 mL/min, 256 nm, $t_1$=24.6 min (minor), $t_2$=28.5 min (major)).

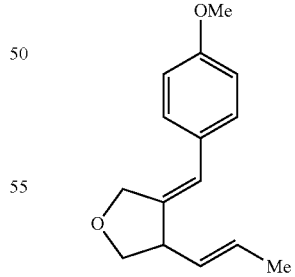

18c (99% yield, 99% ee): $^1$H NMR (500 MHz, $CDCl_3$): δ 2.36 (dd, J=6.5 Hz, 1.5 Hz, 3H), 3.41-3.49 (m, 2H), 3.81 (s, 3H), 4.07 (t, J=7.5 Hz, 1H), 5.31-5.36 (m, 1H), 5.62-5.67 (m, 1H), 6.18 (m, 1H), 6.88 (d, J=9.0 Hz, 2H), 7.08 (d, J=8.5 Hz, 2H). The ee was measured by HPLC (Chiralcel OJ, hexanes/2-propanol=93/7, 0.5 mL/min, 256 nm, $t_1$=20.9 min (minor), $t_2$=29.1 min (major)).

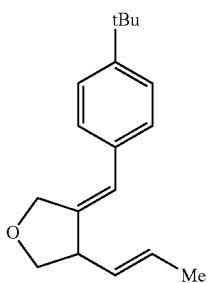 [SMILES: C/C=C/C1COC/C1=C\c1ccc(C(C)(C)C)cc1]

18d (99% NMR yield, 99% ee): $^1$H NMR (500 MHz, CDCl$_3$): δ 1.31 (s, 9H), 1.76 (dd, J=6.5 Hz, 1.5 Hz, 3H), 3.43-3.49 (m, 2H), 4.07 (t, J=7.0 Hz, 1H), 4.62-6.59 (m, 1H), 4.75-4.72 (m, 1H), 5.32-5.37 (unresolved dqq, 1H), 5.63-5.69 (m, 1H), 6.22 (m, 1H), 7.09 (d, J=8.0 Hz, 2H), 7.37 (d, J=8.5 Hz, 2H); $^{13}$C NMR (125 MHz, CDCl$_3$): δ 18.07, 31.29, 34.53, 49.65, 70.42, 72.68, 121.36, 125.45, 127.68, 128.70, 129.33, 134.53, 143.56, 149.60. ESI-MS: calcd for C$_{18}$H$_{25}$O [M+H]$^+$ 257.2. found 257.1. The ee was measured by HPLC (Chiralcel OJ, hexanes/2-propanol=99.6/0.4, 0.5 mL/min, 259 nm, t$_1$=26.4 min (minor), t$_2$=44.1 min (major)).

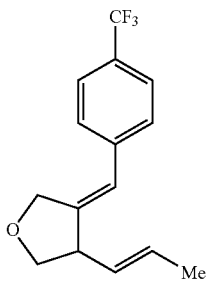 [SMILES: C/C=C/C1COC/C1=C\c1ccc(C(F)(F)F)cc1]

18e (99% yield, 99% ee): $^1$H NMR (500 MHz, CDCl$_3$): δ 1.77 (dd, J=6.5 Hz, 1.5 Hz, 1H), 3.46-3.51 (m, 2H), 4.11 (t, J=5.5 Hz, 1H), 4.57 (m, 1H), 4.72-4.75 (m, 1H), 5.30-5.35 (unresolved ddq, 1H), 5.73 (dq, J=13.0 Hz, 6.5 Hz, 1H), 6.28-6.27 (m, 1H), 7.23 (d, J=8.0 Hz, 2H), 7.58 (d, J=8.0 Hz, 2H). The ee was measured by HPLC (Chiralcel OJ, hexanes/2-propanol=99/1, 0.5 mL/min, 256 nm, t$_1$=14.7 min (minor), t$_2$=20.3 min (major)).

TABLE 8

Asymmetric Alder-Ene Cyclization of 17a.

| entry | Pre-catalyst | Rh loading (mol %) | yield (%)$^b$ | ee (%)$^c$ |
|---|---|---|---|---|
| 1$^d$ | 1•Rh(BF$_4$) | 0.5 | 0 | — |
| 2 | 1•Rh(SbF$_6$) | 0.2 | 99 | 99 |
| 3$^d$ | 1•RhCl | 0.2 | 0 | — |
| 4$^e$ | Rh(Me$_2$L)(SbF$_6$) | 0.2 | 26 | 99 |
| 5$^{e,f}$ | Rh(Me$_2$L)(SbF$_6$) | 0.2 | 26 | 99 |

$^a$Reaction conditions: 17a (1 equiv.), AgSbF$_6$ (10 equiv relative to Rh), catalyst at r.t. for 2 h.
$^b$Determined by $^1$H NMR integration with internal standard.
$^c$Determined by chiral HPLC.
$^d$No AgSbF$_6$ added.
$^e$Catalyst generated in situ.
$^f$Reaction time was 20 h.

TABLE 9

Asymmetric Alder-Ene Reactions with 17a-17e.

| entry | Substrate Aryl Substituent | Rh loading (mol %) | yield (%)$^b$ | ee (%)$^c$ |
|---|---|---|---|---|
| 1 | H (17a) | 0.2 | 99 (18a) | 99 |
| 2 | Me (17b) | 0.2 | 65 (18b) | 99 |
| 3$^d$ | Me (17b) | 0.5 | 99 (18b) | 99 |
| 4 | OMe (17c) | 0.2 | 60 (18c) | 99 |
| 5$^d$ | OMe (17c) | 0.5 | 99 (18c) | 99 |
| 6$^d$ | $^t$Bu (17d) | 0.5 | 99 (18d) | 99 |
| 7 | CF$_3$ (17e) | 0.2 | 99 (18e) | 99 |

$^a$Reaction conditions: 17a-e (1 equiv.), AgSbF$_6$ (10 equiv relative to Rh), catalyst at r.t., 20 h.
$^b$Determined by $^1$H NMR integration with internal standard.
$^c$Determined by chiral HPLC.
$^d$Reaction time was 20 h.

The Rh-catalyzed asymmetric Alder-ene cyclization is a powerful method for generating chiral heterocycles possessing the 1,4-diene products from 1,6-enynes. Without being bound to any one theory, the cyclized product is believed to form via the β-hydride elimination and reductive elimination sequence. While 1.Rh(BF$_4$) efficiently catalyzed the reductive cyclization of 1,6-enynes, it was ineffective in the Alder-ene cycloisomerization. See Table 8, entry 1. Instead, the 1.Rh(SbF$_6$) catalyst, with the less coordinating SbF$_6^-$ anion, generated in situ by treating 1.RhCl with AgSbF$_6$, afforded the cyclized 1,4-diene product in 99% yield and 99% ee. See Table 8, entry 2. The enhanced activity from site isolation in 1.Rh(SbF$_6$) is again demonstrated when comparing the catalytic activity of 1.Rh(SbF$_6$) and Rh(Me$_2$L)(SbF$_6$). See Table 8, entries 2 vs 4. 1.Rh(SbF$_6$) is at least 4 times more active than the homogeneous control. Without being bound to any one theory, it is believed that the Rh catalyst is significantly stabilized due to site isolation. The homogenous catalyst is deactivated within two hours and prolonging the reaction time did not lead to increased product formation. See Table 8, entries 4-5.

1.Rh(SbF$_6$)-catalyzed Alder-ene cycloisomerization also has excellent regioselectivity, which is surprising considering the high reactivity of both the starting enyne 17a and the product 18a under catalytic conditions. Zhang and co-workers reported that 1,6-enyne 17a readily isomerized to the 1,5-enyne in the presence of high loading of homogeneous catalysts (>20 mol %). See Cao et al., Angew. Chem., Int. Ed. 2000, 39, 4101. Additionally, cycloisomerized product 18a is susceptible to isomerization under prolonged reaction conditions forming the more stable conjugated 1,3-diene. Despite the enhanced catalytic activity of 1.Rh(SbF$_6$), isomerized byproducts were not observed and only 17a and 18a were detected in the $^1$H NMR spectrum of the crude reaction mixture.

Other substrates were also studies for 1.Rh catalyzed Alder-ene reactions. See Table 9. With 0.2 mol % catalyst, para-Me substituted enyne 17b was converted to cycloisomerized product 18b in 65% yield and 99% ee. See Table 9, entry 2. Increasing the catalyst loading (0.5 mol %) and reaction time (20 h) led to quantitative yields while maintaining excellent enantioselectivity. See Table 9, entry 3. At 0.5 mol % 1.Rh(SbF$_6$) loadings, cycloisomerized products 18c and 18d were obtained from para-OMe and para-$^t$Bu substituted enyne 17c and 17d in quantitative yields and 99% ee, respectively. See Table 9, entries 5 and 6. Enynes bearing electron-withdrawing groups were significantly more reactive; only 0.2 mol % catalyst loading was needed to convert para-CF$_3$ substituted enyne 17e to its cyclized product in quantitative yield and 99% ee in 2 h. See Table 9, entry 7. As was observed with enyne 17a, undesired isomerization or rearrangement was not observed from any of the 1.Rh(SbF$_6$)-catalyzed Alder-ene reactions.

The PXRD pattern of the recovered 1.Rh(BF$_4$) after the reductive cyclization reaction remained similar to that of freshly prepared 1.Rh(BF$_4$); this holds true for the recovered 1.Rh(SbF$_6$) after the Alder-ene reaction. See FIG. 8. These results indicate the framework of 1 is stable under asymmetric catalytic reaction conditions. However, the recovered 1.Rh(BF$_4$) and 1.Rh(SbF$_6$) showed low or no catalytic activity when re-subjected to reaction conditions with fresh substrates, suggesting that the BINAP-Rh complexes in the MOF slowly form stable but catalytically inactive species during the catalytic processes. Consistent with this, insignificant amounts of Rh and Zr species were leached from the MOFs as determined by ICP-MS.

For the reductive cyclization with 1.Rh(BF$_4$), 0.0% Zr and 3.7% rhodium were found in the supernatant. For the Alder-ene reaction with 1.Rh(SbF$_6$), <0.1% of Zr and Rh species was found in the supernatant.

Example 18

Catalysis of Asymmetric Pauson-Khand Reactions

1.Rh Catalyzed Asymmetric Intramolecular Pauson-Khand-Type Reaction:

Freshly prepared MOF 1 (1.6 mg, 0.53 μmol) was weighed onto a filter paper and then charged into a 1 dram vial. After addition of THF (2.0 mL) and [RhCl(nbd)]$_2$ (21 μL, 0.53 μmol, 0.025M solution in THF), the mixture was allowed to stand for overnight, and then the metalated MOF 1 was centrifuged out of suspension and washed with THF.

A mixture of 1,6-enyne 15b (3.0 mg, 0.018 mmol), cinnamaldehyde (0.13 mL, 1.1 mmol), 1.Rh (0.53 μmol) was stirred under nitrogen atmosphere at 120° C. for 20 h. After the solid catalyst was separated via centrifugation, the supernatant was evaporated. The residue was subjected to preparative TLC (silica gel, hexanes/EtOAc=3/1) to give 6-phenyl-3a,4-dihydro-1H,3H-cyclopenta[c]furan-5-one (100% Conv., 87% ee).

Post-Synthetic Metalation of MOF 11 with [RhCl(Nbd)]$_2$:

Freshly prepared MOF 11 (24.8 mg, 1.72 μmol) was weighed onto a filter paper in a nitrogen-filled glovebox and then charged into a 1 dram vial. After addition of THF (2.0 mL) and [Rh(nbd)Cl]$_2$ (247 μL, 6.18 μmol Rh, 0.025 M solution in THF), the mixture was allowed to stand overnight, and then the metalated 11 was centrifuged out of suspension and washed with THF. ICP-MS analysis determined 61 mol % Rh-loading of H$_2$L.

Exemplary Procedure for 11.Rh Catalyzed Asymmetric Pauson-Khand Reactions:

MOF 11 (24.8 mg, 1.72 μmol) was metalated with [RhCl (nbd)]$_2$ (247 μL, 6.18 μmol Rh, 0.0125 M solution in THF) as described above. A mixture of the 1,6-enyne 1-(3-(allyloxy)prop-1-yn-1-yl)-4-(chloro)benzene 15f (21.4 mg, 0.104 mmol), trans-cinnamaldehyde (0.79 mL, 6.2 mmol) and 11.Rh (1.05 μmol Rh) was stirred under nitrogen atmosphere at 120° C. for 20 h. 11.Rh was removed from the solution by centrifugation. The supernatant was transferred to a clean round-bottom flask, and the MOF was washed further with Et$_2$O. The combined organic extracts were concentrated on a rotary evaporator. The residue was subjected to flash column chromatography (silica gel, hexane/ethyl acetate=10/1 to 2/1), preparative TLC (silica gel, CHCl$_3$/EtOAc=10/1) to give 19f (19.6 mg, 0.0835 mmol, 80% yield, 82% ee).

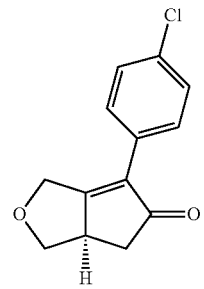 [SMILES: O=C1C[C@H]2COCC2=C1c1ccc(Cl)cc1]

19f (80% yield, 82% ee): $^1$H NMR (500 MHz, CDCl$_3$): δ 2.35 (dd, J=17.5, 3.5 Hz, 1H), 2.86 (dd, J=17.5, 6.5 Hz, 1H), 3.25 (dd, J=11.5, 7.8 Hz, 1H), 3.30-3.38 (m, 1H), 4.39 (t, J=7.8 Hz, 1H), 4.58 (d, J=16.3 Hz, 1H), 4.93 (d, J=16.3 Hz, 1H), 7.39 (d, J=8.5 Hz, 2H), 7.48 (d, J=8.5 Hz, 2H). The ee was measured by HPLC (Chiralpak AD, 0.6 mL/min, hexanes/2-propanol=85/15, 0.6 mL/min, 270 nm, t$_1$=16.7 min (major), t$_2$=18.9 min (minor)).

19b-c and 19e were prepared in a similar manner from 15b-c and 15e.

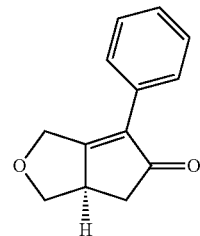 [SMILES: O=C1C[C@H]2COCC2=C1c1ccccc1]

19b (79% yield, 87% ee): $^1$H NMR (500 MHz, CDCl$_3$): δ 2.36 (dd, J=17.5, 3.8 Hz, 1H), 2.86 (dd, J=17.5, 6.5 Hz, 1H), 3.25 (dd, J=11.0, 7.6 Hz, 1H), 3.30-3.39 (m, 1H), 4.39 (t, J=7.6 Hz, 1H), 4.61 (d, J=16.3 Hz, 1H), 4.95 (d, J=16.3 Hz, 1H), 7.36 (t, J=7.5 Hz, 1H), 7.42 (t, J=7.5 Hz, 2H), 7.53 (d, J=7.5 Hz, 2H). The ee was measured by HPLC (Chiralpak AD, 0.8 mL/min, hexanes/2-propanol=90/10, 0.8 mL/min, 260 nm, t$_1$=14.2 min (major), t$_2$=19.5 min (minor)).

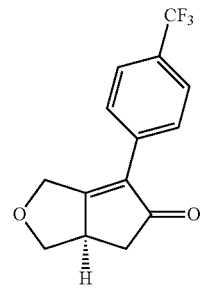

19e (80% yield, 55% ee): $^1$H NMR (500 MHz, CDCl$_3$): δ 2.38 (dd, J=17.5, 3.8 Hz, 1H), 2.89 (dd, J=17.5, 6.3 Hz, 1H), 3.28 (dd, J=11.0, 8.0 Hz, 1H), 3.34-3.44 (m, 1H), 4.42 (t, J=8.0 Hz, 1H), 4.61 (d, J=16.5 Hz, 1H), 4.98 (d, J=16.5

Hz, 1H), 7.65 (d, J=8.8 Hz, 2H), 7.68 (d, J=8.8 Hz, 2H). The ee was measured by HPLC (Chiralcel OD-H, 0.6 mL/min, hexanes/2-propanol=80/20, 254 nm, $t_1$=18.1 min (major), $t_2$=23.2 min (minor)).

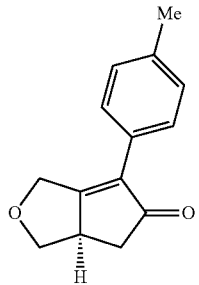 [SMILES: Cc1ccc(C2=C3COC[C@@H]3CC2=O)cc1]

19a (62% yield, 67% ee): $^1$H NMR (500 MHz, CDCl$_3$): δ 2.33 (dd, J=17.5, 3.5 Hz, 1H), 2.37 (s, 3H), 2.84 (dd, J=17.5, 6.0 Hz, 1H), 3.23 (dd, J=11.5, 7.8 Hz, 1H), 3.27-3.36 (m, 1H), 4.37 (t, J=7.8 Hz, 1H), 4.59 (d, J=16.5 Hz, 1H), 4.93 (d, J=16.5 Hz, 1H), 7.22 (d, J=8.0 Hz, 2H), 7.42 (d, J=8.0 Hz, 2H). The ee was measured by HPLC (Chiralpak AD, 0.6 mL/min, hexanes/2-propanol=85/15, 230 nm, $t_1$=14.0 min (major), $t_2$=15.8 min (minor)).

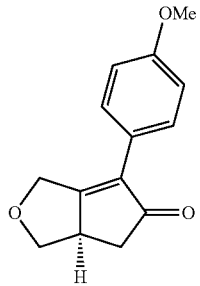 [SMILES: COc1ccc(C2=C3COC[C@@H]3CC2=O)cc1]

19c (67% yield, 83% ee): $^1$H NMR (500 MHz, CDCl$_3$): δ 2.32 (dd, J=17.5, 3.5 Hz, 1H), 2.83 (dd, J=17.5, 6.0 Hz, 1H), 3.22 (dd, J=11.0, 7.6 Hz, 1H), 3.26-3.35 (m, 1H), 3.83 (s, 3H), 4.37 (t, J=7.6 Hz, 1H), 4.59 (d, J=16.3 Hz, 1H), 4.92 (d, J=16.3 Hz, 1H), 6.94 (d, J=8.8 Hz, 3H), 7.49 (d, J=8.8 Hz, 2H). The ee was measured by HPLC (Chiralpak AD, 0.6 mL/min, hexanes/2-propanol=85/15, 285 nm, $t_1$=21.3 min (major), $t_2$=24.2 min (minor)).

Recyclability Test for 11.Rh Catalyzed Asymmetric Pauson-Khand Reaction:

MOF 11 (24.8 mg, 1.72 μmol) was metalated with [RhCl(nbd)]$_2$ (247 μL, 6.18 μmol Rh, 0.025 M solution in THF) as described above. A mixture of 1,6-enyne 15f (21.4 mg, 0.104 mmol), trans-cinnamaldehyde (0.79 mL, 6.24 mmol), 11.Rh (1.04 μmol Rh) was stirred under nitrogen atmosphere at 120° C. for 20 h. 11.Rh was removed from the solution by centrifugation. The supernatant was transferred to a clean round-bottom flask, and the MOF was washed further with Et$_2$O. The combined organic extracts were concentrated on a rotary evaporator. The solid catalyst was separated via centrifugation, and then the supernatant was worked up and subjected to flash column chromatography (silica gel, hexanes/ethyl acetate=10/1 to 2/1), preparative TLC (silica gel, CHCl$_3$/EtOAc=10/1) to give 19f (19.6 mg, 0.0832 mmol, 80% yield, 82% ee). The solid catalyst was added to a solution of 1,6-enyne 15f (21.4 mg, 0.104 mmol), trans-cinnamaldehyde (0.79 mL, 6.24 mmol). After stirring at 120° C. for 20 h, the mixture was worked up and subjected to flash column chromatography (silica gel, hexanes/ethyl acetate=10/1 to 2/1), preparative TLC (silica gel, CHCl$_3$/EtOAc=10/1) to give 19f (10.2 mg, 0.0435 mmol, 42% yield, 79% ee).

Procedure for Catalyzed Asymmetric Pauson-Khand Reaction Under Carbon Monoxide.

Scheme 20. Asymmetric Pauson-Khand reaction with carbon monoxide

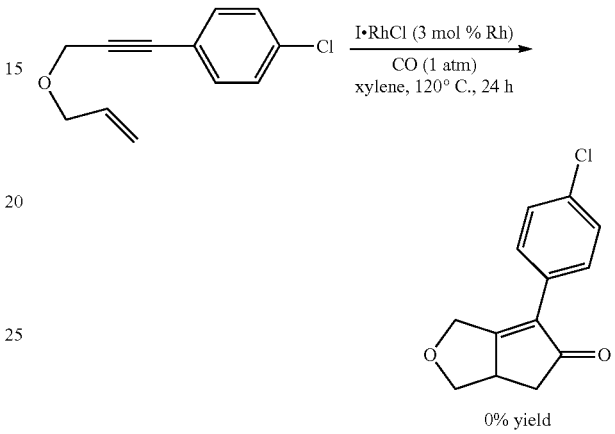

0% yield

MOF 1 (6.0 mg, 2.0 μmol) was metalated with [Rh(nbd)Cl]$_2$ (40.0 μL, 1.00 μmol, 0.025M solution in THF) as described above. As shown in Scheme 20, above, 1.Rh (0.36 μmol based on Rh suspended in 1.00 mL m-xylene) was added to 1,6-enyne 15f (2.5 mg, 12 μmol). The reaction mixture was stirred under a carbon monoxide atmosphere at 120° C. for 24 hours. 1.Rh was removed from the solution by centrifugation. The supernatant was transferred to a clean round-bottom flask, and the MOF was washed further with EtOAc. The combined organic extracts were concentrated on a rotary evaporator. (0% $^1$H NMR yield)

Discussion:

The Pauson-Khand reaction is a useful carbonylative alkene-alkyne coupling method to afford chiral bicyclic heterocycles from relatively simple starting materials, but can be sterically demanding. Based on the success of catalyzing reductive cyclization of 1,6-enynes, Pauson-Khand reactions under an atmosphere of CO with 1.Rh were studied. Attempts at a Pauson-Khand reaction with para-Cl substituted enyne 15f and CO were unsuccessful. Without being bound to any one theory, the inability to perform Pauson-Khand reactions with particular MOF catalysts was attributed to limited solubility and permeability of CO under the heated reaction conditions. As an alternative method to introduce CO, aldehydes can be used as both solvent and CO source for metal-catalyzed Pauson-Khand type reactions. See Morimoto et al., J. Am. Chem. Soc., 2002, 124, 3806; Shibata et al., Org. Lett., 2002, 4, 1619; and Shibata et al., J. Org. Chem., 2002, 67, 7446. In addition to the obvious advantage of generating CO in situ, Shibata and co-workers found Rh-phosphine catalysts generated Pauson-Khand products in significantly higher yields using cinnamaldehyde as the CO source versus carrying out the reaction in an atmosphere of CO. See Shibata et al., J. Org. Chem., 2002, 67, 7446. Unfortunately, the 1.Rh catalyzed asymmetric Pauson-Khand reaction of 15f and cinnamaldehyde affords the desired bicyclic product 19f in low yield (<5%). See FIG. 9A. Without being bound to any one theory, it is believed that the low catalytic activity of 1.Rh is resultant of insufficient reaction space required to accommodate the large bicyclic rhodacycle intermediate. To increase the reaction space through modification of the effective pore space, a new BINAP-doped MOF was prepared from a mixture of functionalized and unfunctionalized linkers of identical lengths. See FIG. 9B.

The asymmetric Pauson-Khand type reaction of 1,6-enyne 15f and trans-cinnamyl aldehyde (60 equiv.) with 11.RhCl (0.5 mol % Rh) afforded the chiral bicyclic product 19f in 67% yield and 80% ee. See Table 10, entry 2. The inclusion of unfunctionalized $H_2L_2$ linkers in 11 creates more open space around the BINAP-Rh active sites, allowing the generation of sterically demanding bicyclic rhodacycle intermediates. Additionally, random distribution of $H_2L$ linkers affords more homogeneous distribution of Rh upon post-metalation. The ability of 11.RhCl in catalyzing this reaction has interesting mechanistic implications. Shibata and co-workers proposed that the cinnamaldehyde decarbonylation-Pauson-Khand reaction did not occur through the formation of CO gas as an intermediate, but instead involved a direct CO transfer between two independent Rh-mediated catalytic cycles. See Shibata et al., J. Org. Chem., 2002, 67, 7446. With the mixed-linker MOF 11.RhCl as a single-site solid catalyst, such a direct CO transfer mechanism cannot be operative. Thus, the presently disclosed results are suggestive of a Pauson-Khand type reaction via CO generation from cinnamaldehyde.

To further assess the impact of site isolation on the Pauson-Khand type reaction, the activity of 11.RhCl was compared to the homogeneous control; at 0.5 mol % catalyst loading of homogeneous Rh(Me$_2$L)Cl, less than 5% product 19f was obtained. See Table 10, entry 3. Increasing the Rh(Me$_2$L)Cl loading to 5 mol % led to the formation of 19f in 69% yield. 11.RhCl thus appears to be about 10 times more active than the homogeneous control (see Table 10, entries 2 vs 4), and exhibits similar enantioselectivity as the homogeneous catalyst. A higher yield of 19f (80%) was obtained when 1 mol % of 11.RhCl was used. See Table 10, entry 6.

With optimized conditions for the 11.RhCl catalyzed Pauson-Khand reaction of 15f in hand, other 1,6-enyne substrates bearing either electron withdrawing or electron donating substituents were also studied. See Table 11. Substrates bearing electron-withdrawing substituents, such as para-Cl 15f and para-CF$_3$ 15e, afford the desired bicyclic products in good yield and modest enantioselectivity. With electron-donating substituents such as para-Me (15a) and para-OMe (15c), the Pauson-Khand products were obtained in lower yields but slightly higher ee's. See Table 11, entries 3-4. At 0.5 mol % 11.RhCl, un-substituted enyne 15b afforded the bicyclic product in 79% yield and 87% ee. See Table 11, entry 5.

Figure 11:
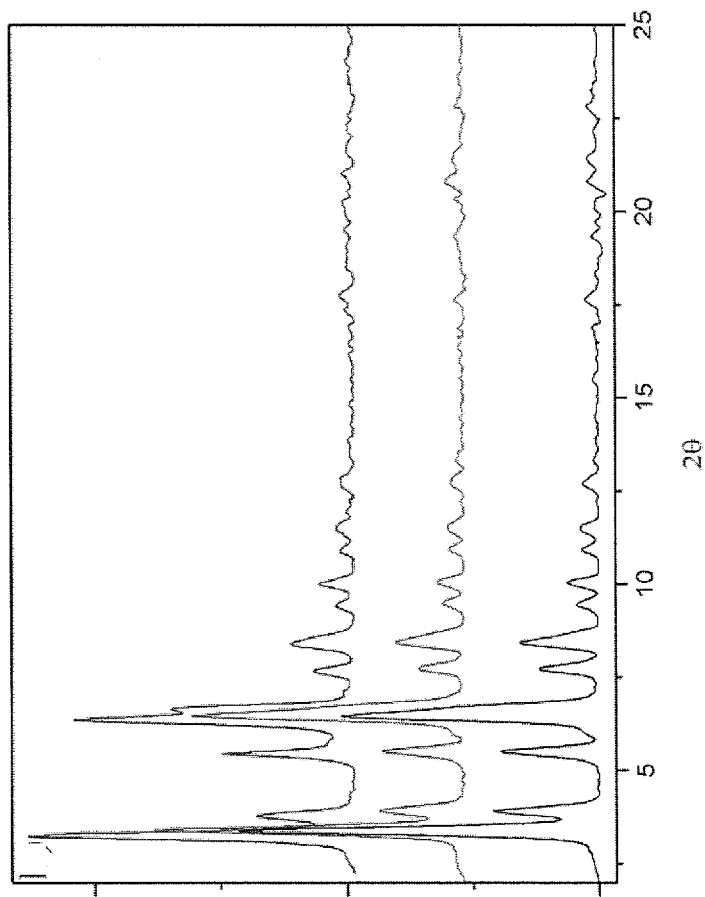
FIG. 11 is a graph showing the powder x-ray diffraction (PXRD) patterns for a metal-organic framework containing mixed organic binding ligands, including a (2,2'-bis(diphenylphosphino)-1,1-binaphthyl) (BINAP)-based organic bridging ligand and a nonchiral nitro-group containing organic bridging ligand, and zirconium oxoclusters (i.e., MOF 11, bottom; MOF 11 after metalation with rhodium chloride (middle); and the metalated MOF 11 after recovery from Pauson-Khand reactions (top).

The heterogeneous nature of 11.RhCl was confirmed by the following experiments. PXRD of 11.RhCl recovered from the Pauson-Khand reaction with 15f indicated that the crystallinity of 11.RhCl was maintained throughout the course of the reaction. See FIG. 11. CP-MS analyses indicated that <0.5% Zr and 5.1% Rh species had leached into the supernatant of the 11.RhCl-catalyzed Pauson-Khand reaction of 15f. Finally, the recovered 11.RhCl catalyst remained active for the second round of Pauson-Khand reaction albeit affording the product in lower yield (42% isolated yield, 79% ee).

TABLE 10

Asymmetric Pauson-Khand Type Reactions of 1,6-Enyne 15f.

| entry | catalyst | cat. loading (mol %) | yield (%) | ee (%)[b] |
|---|---|---|---|---|
| 1 | 1•RhCl | 0.5 | <5[c] | —[d] |
| 2 | 11•RhCl | 0.5 | 67 | 80 |
| 3 | Rh(Me$_2$L)Cl | 0.5 | <5[c] | —[d] |
| 4 | Rh(Me$_2$L)Cl | 5.0 | 69 | 77 |
| 5 | Rh(Me$_2$L)Cl | 10 | 84 | 77 |
| 6 | 11•RhCl | 1.0 | 80 | 82 |

[a]Reaction conditions: 15f (1 equiv.), trans-cinnamaldehyde (60 equiv.), catalyst at 120° C. for 20 h.
[b]Determined by chiral HPLC.
[c]Determined by $^1$H NMR integration.
[d] Not determined

TABLE 11

Asymmetric Pauson-Khand Type Reactions of 1,6-Enynes with 11•RhCl.

| entry | Substrate Aromatic Substituent | yield (%)[b] | ee (%)[c] |
|---|---|---|---|
| 1 | Cl (15f) | 80 (19f) | 82 |
| 2 | CF$_3$ (15e) | 80(19e) | 55 |
| 3 | Me (15a) | 62 (19a) | 67 |
| 4 | OMe (15c) | 67 (19c) | 83 |
| 5[d] | H (15b) | 79 (19b) | 87 |

[a]Reaction conditions: 15 (1 equiv.), trans-cinnamaldehyde (60 equiv.), catalyst 11•RhCl (1 mol % Rh) at 120° C. for 20 h.
[b]Isolated yield.
[c]Determined by chiral HPLC.
[d]0.5 mol % Rh.

Example 19

General Procedures for Studies Related to the Chiral Diene MOFs

All anaerobic and moisture-sensitive manipulations were carried out with standard Schlenk techniques under predried nitrogen or with glovebox techniques under nitrogen. $^1$H NMR spectra were recorded on a Bruker NMR 500 DRX spectrometer (Bruker Corporation, Billerica, Mass., United States of America) at 500 MHz and referenced to the proton resonance resulting from incomplete deuteration of the CDCl$_3$ (δ 7.26) or DMSO-d$_6$ (δ 2.50). $^{13}$C NMR spectra were recorded at 125 MHz, and all of the chemical shifts are reported downfield in ppm relative to the carbon resonance of CDCl$_3$ (δ 77.00) or DMSO-d$_6$ (δ 39.50). The following abbreviations are used; s: singlet, d: doublet, t: triplet, q: quartet, m: multiplet, br: broad, app: apparent. Mass spectra were obtained with an Agilent 1100 LC-MSD Mass Spectrometer (Agilent Technologies, Santa Clara, Calif., United States of America) and Agilent 6224 Accurate-Mass TOF-MS (Agilent Technologies, Santa Clara, Calif., United States of America). Thermogravimetric analysis (TGA) was performed in air using a Shimadzu TGA-50 (Shimadzu Corporation, Kyoto, Japan) equipped with a platinum pan. Single-crystal X-ray diffraction were collected with a Bruker APEX II CCD-based detector (Bruker Corporation, Billerica, Mass., United States of America). Powder X-ray diffraction (PXRD) patterns were collected on a Bruker D8 Venture, dual microsource (Cu and Mo) diffractometer (Bruker Corporation, Billerica, Mass., United States of America) with a CMOS detector. Cu Kα radiation was used.

The PXRD patterns were processed with the APEX 2 package using PILOT plug-in. ICP-MS data were obtained with an Agilent 7700x ICP-MS (Agilent Technologies, Santa Clara, Calif., United States of America) and analyzed using ICP-MS MassHunter version B01.03. Samples were diluted in a 2% $HNO_3$ matrix and analyzed with a 159Tb internal standard against a six-point standard curve over the range from 0.1 ppb to 1000 ppb. The correlation coefficient was >0.9997 for all analyses of interest. Data collection was performed in Spectrum Mode with five replicates per sample and 100 sweeps per replicate. Enantiomeric excess (ee) values were determined by chiral high performance liquid chromatography (HPLC) using a Shimadzu SCL-10A HPLC (Shimadzu Corporation, Kyoto, Japan) equipped with a SPD-M10A photodiode array detector. 1,4-Dioxane was distilled over Na under $N_2$. Toluene was purified by passing through a neutral alumina column under $N_2$. 2-Cyclohexen-1-one, 2-cyclohepten-1-one, 2-cyclopenten-1-one, 4-hexen-3-one were purchased and distilled before use. [RhCl$(C_2H_4)]_2$, Rh(acac)$(C_2H_4)_2$, phenylboronic acid, 4-fluorophenylboronic acid, and 4-methoxyphenylboronic acid were used as received. N-(4-Chlorophenyl)methylidene-4-methylbenzenesulfonamide, N-phenylmethylidene-4-methylbenzenesulfonamide, N-(4-methoxyphenyl)methylidene-4-methylbenzenesulfonamide, dimethyl 4,4'-((2-nitro-[1,1'-biphenyl]-4,4'-diyl)bis(ethyne-2,1-diyl)) dibenzoate, and (1R,4R,7R)-7-isopropyl-5-methylbicyclo [2.2.2]octa-2,5-diene-2-carboxylic acid were prepared according or analogous to reported procedures. See e.g., Okamoto et al., Chem. Commun., 2009, 4815; Pattison et al., J. Am. Chem. Soc., 2010, 132, 14373; Love et al., Synlett, 1994, 493.

Example 20

Synthesis of Dimethyl 4,4'-((2-amino-[1,1'-biphenyl]-4,4'-diyl)bis-(ethyne-2,1-diyl)dibenzoate As shown in Scheme 21, above, a mixture of dimethyl 4,4'-((2-nitro-[1,1'-biphenyl]-4,4'-diyl)bis(ethyne-2,1-diyl)) dibenzoate (1.289 g, 2.500 mmol) and zinc powder (3.269 g, 50.00 mmol) was dissolved in acetic acid (8.3 mL), MeOH (50 mL) and THF (75 mL) under nitrogen. After stirring at rt for 3 h, saturated sodium bicarbonate was added at 0° C. The solution was extracted with $CHCl_3$, and then the combined organic extracts were dried over $Na_2SO_4$ and filtered. After evaporation of the solvent, the residue was subjected to flash column chromatography (silica gel, hexane/$CHCl_3$/EtOAc=10/10/1) to give dimethyl 4,4'-((2-amino-[1,1-biphenyl]-4,4'-diyl)bis(ethyne-2,1-diyl))dibenzoate (658.4 mg, 1.356 mmol, 54% yield). $^1$H NMR ($CDCl_3$): δ 3.93 (s, 3H), 3.94 (s, 3H), 6.96 (d, J=1.3 Hz, 1H), 7.03 (dd, J=7.8, 1.3 Hz, 1H), 7.13 (d, J=7.8 Hz, 1H), 7.49 (d, J=8.0 Hz, 2H), 7.56-7.66 (m, 6H), 8.03 (d, J=8.5 Hz, 2H), 8.04 (d, J=8.5 Hz, 2H). $^{13}$C NMR ($CDCl_3$): δ 52.22, 52.25, 88.52, 89.30, 92.03, 92.44, 118.51, 121.86, 122.30, 122.92, 127.32, 127.86, 128.05, 128.97, 129.51, 129.54, 130.41, 131.51, 131.53, 132.24, 139.27, 143.44, 166.53, 166.57. HRMS(ESI): calcd for $C_{32}H_{24}NO_4$ [M+H]$^+$ 486.1705. found 486.1693.

Example 21

Synthesis of Dimethyl 4,4'-((2-((1R,4R,7R)-7-isoporpyl-5-methylbicyclo[2.2.2] octa-2,5-diene-2-carboxamido)-[1,1'-biphenyl]-4,4'-diyl)bis(ethyne-2, 1-diyl)dibenzoate Scheme 22. Synthesis of Dimethyl 4,4'-((2-((1R,4R,7R)-7-isoporpyl-5-methylbicyclo[2.2.2] octa-2,5-diene-2-carboxamido)-[1,1'-biphenyl]-4,4'-diyl)bis(ethyne-2,1-diyl)dibenzoate (LMe$_2$)

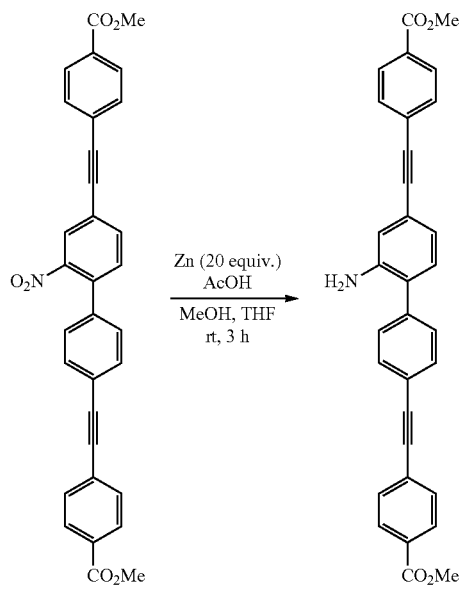

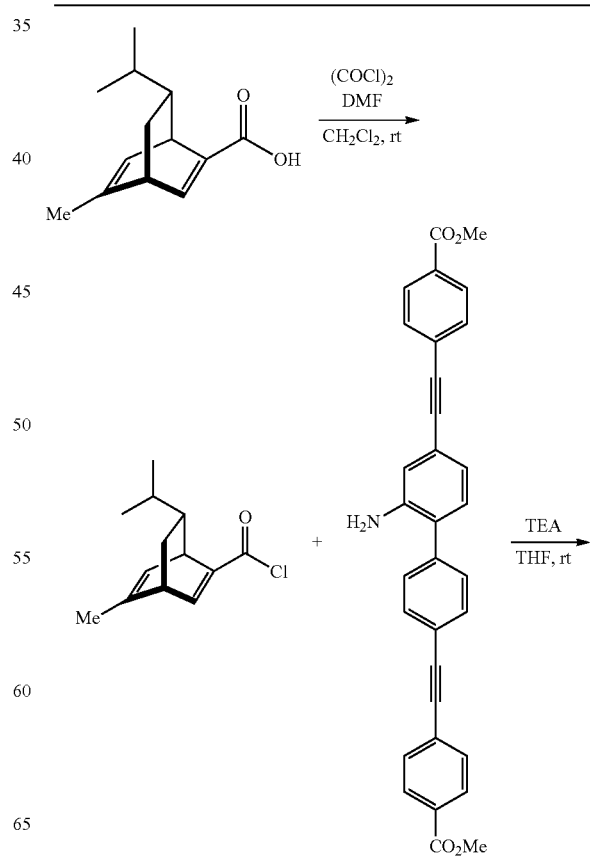

-continued

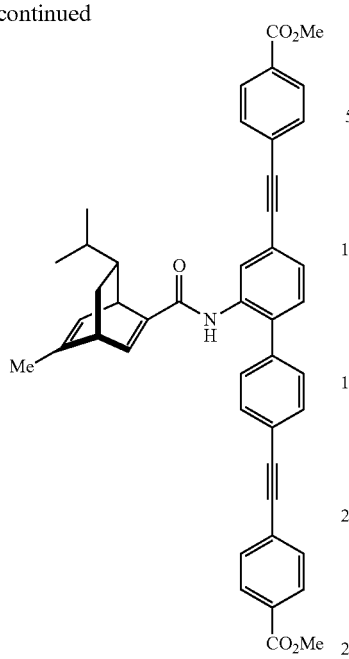

As shown in Scheme 22, above, to a solution of (1R,4R,7R)-7-isopropyl-5-methylbicyclo[2.2.2]octa-2,5-diene-2-carboxylic acid (84.3 mg, 0.409 mmol) in CH$_2$Cl$_2$ was added oxalyl chloride (42 µL, 0.49 mmol) and DMF (3 drops) at 0° C. The mixture was stirred at room temperature for 3 h, and then the residue was added to a mixture of dimethyl 4,4'4 (2-amino-[1,1'-biphenyl]-4,4'-diyl)bis(ethyne-2,1-diyl))dibenzoate (198.4 mg, 0.4086 mmol), TEA (85 µL, 0.61 mmol), and THF (41 mL). After stirring at room temperature for 24 h, saturated NH$_4$Cl was slowly added at 0° C. The mixture was extracted with Et$_2$O, and the combined organic extracts were dried over MgSO$_4$ and filtered. After evaporation of the solvent, the residue was subjected to flash column chromatography (silica gel, hexanes/CHCl$_3$/EtOAc=20/20/1) to give LMe$_2$ (157.1 mg, 0.2332 mmol, 57% yield). $^1$H NMR (CDCl$_3$): δ 0.80 (d, J=6.5 Hz, 3H), 0.92-0.98 (m, 1H), 0.93 (d, J=6.5 Hz, 3H), 1.01-1.12 (m, 1H), 1.12-1.20 (m, 1H), 1.50-1.58 (m, 1H), 1.80 (d, J=1.0 Hz, 3H), 3.30-3.37 (m, 1H), 3.93 (s, 3H), 3.94 (s, 3H), 3.96-4.03 (m, 1H), 5.78 (d, J=6.0 Hz, 1H), 6.65 (dd, J=6.5, 1.5 Hz, 1H), 7.22 (d, J=7.8 Hz, 1H), 7.33 (dd, J=7.8, 1.3 Hz, 1H), 7.42 (d, J=8.3 Hz, 2H), 7.54 (s, 1H), 7.59 (d, J=8.0 Hz, 2H), 7.62 (d, J=8.0 Hz, 2H), 7.68 (d, J=8.3 Hz, 2H), 8.02 (d, J=8.0 Hz, 2H), 8.05 (d, J=8.0 Hz, 2H), 8.73 (d, J=1.3 Hz, 1H). $^{13}$C NMR (CDCl$_3$): δ 18.85, 21.19, 21.74, 31.61, 33.67, 39.76, 43.74, 47.75, 52.15, 52.22, 89.13, 89.87, 91.50, 92.11, 122.79, 123.23, 123.82, 123.98, 127.02, 127.49, 127.87, 129.30, 129.41, 129.46, 129.54, 129.73, 129.86, 131.15, 131.50, 132.46, 135.03, 137.87, 139.53, 143.70, 144.97, 163.27, 166.40, 166.51. HRMS (ESI): calcd for C$_{45}$H$_{40}$NO$_5$ [M+H]$^+$ 674.2906. found 674.2892.

Example 22

Synthesis of 4,4'-((2-((1R,4R,7R)-7-isopropyl-5-methylbicyclo[2.2.2]octa-2,5-diene-2-carboxamido)-[1,1'-biphenyl]-4,4'-diyl)bis(ethyne-2,1-diyl)dibenzoic acid (LH$_2$)

Scheme 23. Synthesis of 4,4'-((2-((1R,4R,7R)-7-isopropyl-5-methylbicyclo[2.2.2]octa-2,5-diene-2-carboxamido)-[1,1'-biphenyl]-4,4'-diyl)bis(ethyne-2,1-diyl))dibenzoic acid (LH$_2$)

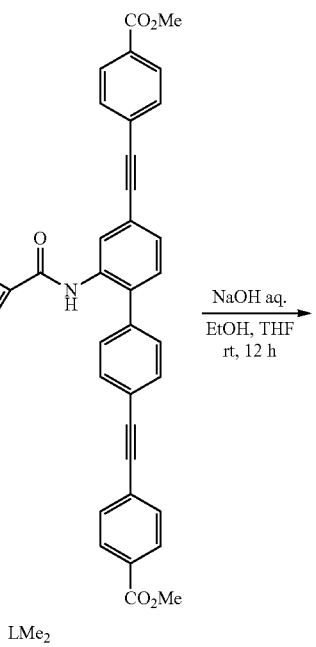

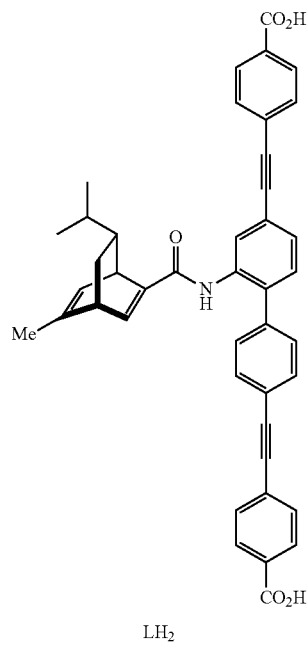

As shown in scheme 23, LMe$_2$ (223.8 mg, 0.3321 mmol) was dissolved in a mixture of THF (17 mL), EtOH (17 mL), and 1 M NaOH (aq) (17 mL). After stirring at room temperature for 12 h, 1 M HCl (aq) was slowly added at 0° C. The filtrate was extracted with EtOAc, and the combined organic extracts were concentrated in vacuo. The residue was washed with water, hexanes, MeOH, and EtOAc to give compound $LH_2$ (165.7 mg, 0.2566 mmol, 77% yield). $^1H$ NMR ($CDCl_3$): δ 0.79 (d, J=5.5 Hz, 3H), 0.84-0.93 (m, 1H), 0.89 (d, J=5.5 Hz, 3H), 0.95-1.04 (m, 1H), 1.45-1.55 (m, 1H), 1.78 (s, 3H), 3.91 (d, J=5.5 Hz, 1H), 5.76 (d, J=6.0 Hz, 1H), 6.98 (d, J=7.0 Hz, 1H), 7.46 (d, J=8.0 Hz, 1H), 7.47 (d, J=8.3 Hz, 2H), 7.54 (dd, J=8.0, 1.0 Hz, 1H), 7.62 (d, J=8.3 Hz, 2H), 7.68 (d, J=8.0 Hz, 2H), 7.712 (d, J=8.0 Hz, 2H), 7.714 (s, 1H), 7.98 (d, J=8.0 Hz, 2H), 9.26 (s, 1H), 13.17 (br, 2H). $^{13}C$ NMR ($CDCl_3$): δ 18.78, 21.18, 21.70, 30.41, 31.33, 33.37, 42.98, 47.37, 89.25, 89.31, 91.31, 91.88, 120.84, 121.46, 123.70, 126.44, 126.55, 128.98, 129.58, 129.59, 130.31, 130.60, 130.67, 131.51, 131.54, 131.61, 135.50, 137.15, 139.15, 139.69, 143.46, 143.68, 163.89, 166.68. ESI-MS: calcd for $C_{43}H_{35}NO_5$ $[M]^-$ 645.3. found 644.9.

Example 23

Preparation and Characterization of Chiral Diene MOF ($E_2$-MOF)

$LH_2$ (8.3 mg, 13 μmol) from Example 22, $ZrCl_4$ (3.0 mg, 13 μmol), DMF (1.8 mL), and trifluoroacetic acid (10 μL) were charged in a vial. The vial was then heated in a 70° C. oven for 5 days, resulting in colorless crystals (15.4 mg, 5.43 μmol, 42% yield). $E_2$-MOF had 73% solvent weight based on TGA analysis, suggestive of a highly porous framework structure.

Single crystal X-ray diffraction of $E_2$-MOF was collected with a Bruker APEX II CCD-based detector (Bruker Corporation, Billerica, Mass., United States of America). The crystals were mounted inside a capillary tube (0.2 mm ID) with a small amount of mother liquid to prevent solvent loss from the crystal. The frames were integrated with the Bruker SAINT© build in APEX II software package (Bruker Corporation, Billerica, Mass., United States of America) using a narrow-frame integration algorithm which also corrects for the Lorentz and polarization effects. Absorption corrections were applied using SADABS. Structures were solved by direct methods and refined to convergence by the least squares method on $F^2$ using the SHELXTL software suite. See Sheldrick, Acta Crystallogr., Sect. A, 2008, 64, 112.

Due to the disorder caused by random orientations, the diene moiety cannot be located in the electron density map and are thus are modeled in the single crystal structure. SQUEEZE subroutine of the PLATON software suite was applied to remove the scattering from the highly disordered guest molecules. The resulting new HKL4 files were used to further refine the structures. Due to the relatively weak diffraction and low resolution, which is not uncommon for this kind of framework with very large solvent accessible void space, restraints (SIMU and DELU) on displacement parameters, and DFIX for bond lengths are applied. Carbon atoms are refined isotropically.

Crystal data and structure refinements of $E_2$-MOF are described in Table 12, below. $E_2$-MOF crystallizes in the Fm3m space group and adopts the UiO structure. The chiral diene moieties are believed to be randomly distributed in the structure. 1H NMR spectrum of digested $E_2$-MOF confirms that the chiral diene groups remain intact during the MOF crystal growth.

TABLE 12

Crystal data and structure refinements of $E_2$-MOF.

| Empirical formula | $Zr_6(O)_4(OH)_4L_6$ | Density (calcd. g/cm$^3$) | 0.225 |
|---|---|---|---|
| Formula weight | 4541.81 | Absorption coeff. (mm$^{-1}$) | 0.091 |
| Temperature (K) | 296(2) | F(000) | 6496 |
| Wavelength (Å) | 0.51800 | Crystal size (mm) | 0.08 × 0.08 × 0.08 |
| Crystal system | Cubic | Crystal color & shape | Colorless block |
| Space group | Fm3m | θ range data collection | 0.65-15.75 |
| Unit cell dimensions | a = 45.887(8) | Limiting indices | −47 <= h <= 48, |
|  | b = 45.887(8) |  | −42 <= k <= 48, |
|  | c = 45.887(8) |  | −33 <= l <= 47 |
|  | α = 90 | Reflection collected | 159296 |
|  | β = 90 | Independent reflections | 2870 |
|  | γ = 90 | R(int) | 0.1528 |
|  |  | Data/restraints/parameters | 2870/118/68 |
|  |  | Goodness-of-fit on $F^2$ | 1.468 |
| Volume (Å$^3$) | 96622(28) | Final R indices [I > 2σ(I)] | R1 = 0.1012, wR2 = 0.2841 |
| Z | 4 | R indices (all data) | R1 = 0.1257, wR2 = 0.3038 |

X-Ray Absorption Spectroscopy:

X-ray absorption spectra were collected at the Rh K-edge (23220 eV) in transmission mode. The X-ray beam was monochromatized by a Si(111) monochromater and detuned by 25% to minimize harmonics. In an inert environment, 11-37 mg dry Rh samples (sufficient to achieve 1-2 absorption edges) were ground thoroughly with a mortar and pestle, then blended with polyethylene glycol (PEG) and pressed into pellets for XAFS analysis. A Rh foil was used as the reference for energy calibration and was measured simultaneously while collecting data for experimental samples. The incident beam intensity ($I_0$) and transmitted beam intensity ($I_t$) were measured by ionization chambers with 100% $N_2$ gas composition. The beam was masked to 1 mm. Data were collected in three regions, with all energies listed relative to the environmental Rh K-edge (23220 eV):

a pre-edge region, −150 to −20 eV (5 eV step size, 1.0 s dwell time); XANES region, −10 to 25 eV (0.5 eV step size, 1.0 s dwell time); and EXAFS region, 2.56 Å$^{-1}$ to 13 Å$^{-1}$ (0.05 Å$^{-1}$ step size, 1.0 s dwell time). Three spectra were collected at room temperature for [RhCl(nbd)]$_2$, RhCl—H$_2$L, and E$_2$-MOF.RhCl.

Prior to averaging, data were aligned to the first and largest peak in the smoothed first derivative of the absorption spectrum, background removed, and spectra processed to obtain a normalized unit edge step. Data were processed and fit with k$^2$-weighting in R-space. All single-scattering and multiple-scattering paths with relative intensity greater than 10% of the first single scattering path and half-path length (R$_{eff}$) less than 5 Å were used for fitting. [RhCl(nbd)]$_2$ was fit with ΔR=1.25-5 Å, and Δk=2.0-12, yielding 23 independent points. E$_2$-MOF.RhCl was fit with ΔR=1-5.4. Å, and Δk=2.0-11.2, yielding 25 independent points. For all fits, the number of parameters used was less than ⅔ the total number of independent points, as determined by the Nyquist Equation. Fits were performed in R-space. Refinement was performed by optimizing an amplitude factor S$_0^2$ and energy shift parameter E$_0$ which are common to all paths, in addition to parameters for bond length (ΔR) and mean squared relative displacement (σ$^2$). [RhCl(nbd)]$_2$ was fitted with the corresponding crystal structure ZOWVUC obtained from the Cambridge Crystallographic Database.

Figure 14B:
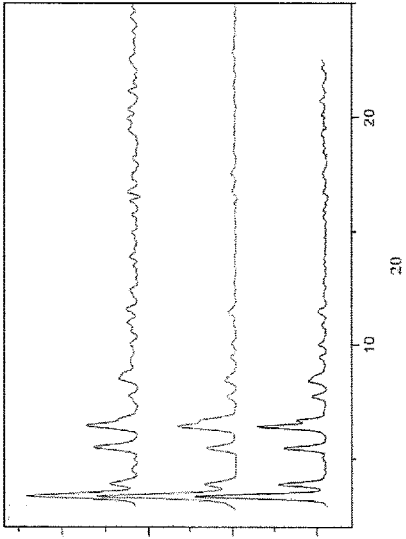
FIG. 14B is a graph showing the powder x-ray diffraction (PXRD) patterns of a chiral diene-containing metal-organic framework ($E_2$-MOF) catalyst of the presently disclosed subject matter. The pattern at the bottom is for $E_2$-MOF metalated with rhodium acetylacetonate (Rh(acac)), but prior to use as a catalyst. The middle pattern is for the metalated MOF recovered from a 1,2 addition reaction. The top pattern is for the metalated MOF recovered after eight uses in a 1,2 addition reactions.
Figure 14A:
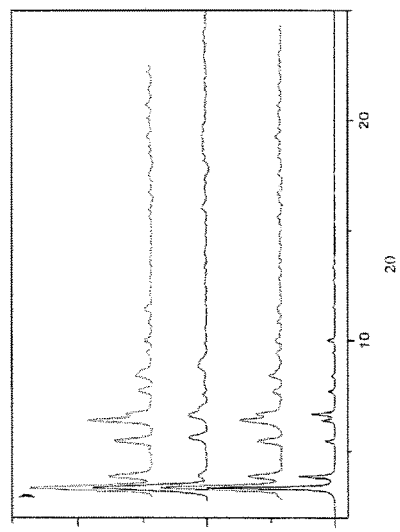
FIG. 14A is a graph showing the PXRD patterns of a chiral diene-containing metal-organic framework ($E_2$-MOF) of the presently disclosed subject matter. The bottom pattern is the simulated pattern. The pattern second from the bottom was obtained experimentally. The pattern third from the bottom shows $E_2$-MOF after metalation with rhodium chloride (RhCl), i.e., $E_2$-MOF.RhCl. The top pattern shows the MOF after metalation with rhodium acetylacetonate (Rh (acac)), i.e., $E_2$-MOF.Rh(acac).

Discussion:

Postsynthetic metalation of E$_2$-MOF was carried out by treatment with 1 equiv of [RhCl(C$_2$H$_4$)$_2$]$_2$ or 1 equiv of Rh(acac)(C$_2$H$_4$)$_2$, respectively (based on the Rh equivalent with respect to the L equivalents in E$_2$-MOF, SI; acac is acetylacetonate). Powder X-ray diffraction (PXRD) studies indicated that E$_2$-MOF.RhCl and E$_2$-MOF.Rh(acac) remained crystalline and adopted the same structure as E$_2$-MOF. See FIG. 14A. Inductively coupled plasma mass spectrometry (ICP-MS) was used to determine the extent of metalation in E$_2$-MOF based on the Rh to Zr ratios. E$_2$-MOF.RhCl achieved 66% metalation whereas E$_2$-MOF.Rh(acac) only had 13% of the L ligands metalated.

Figure 14D:
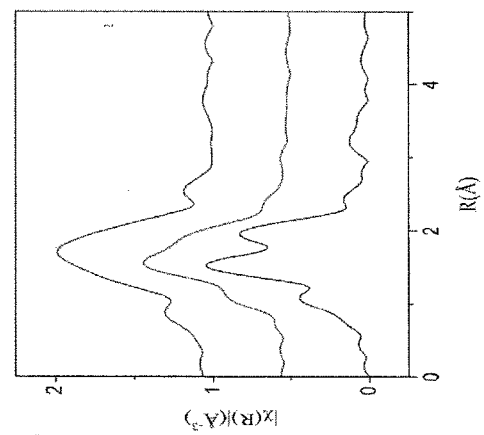
FIG. 14D is a graph showing the comparison of the extended x-ray absorption fine structure (EXAFS) data for a chiral diene-containing metal-organic framework ($E_2$-MOF) metalated with ruthenium chloride (RhCl; top data line); ruthenium chloride complexed to the chiral diene-containing dibenzoate organic ligand used to prepare the $E_2$-MOF (middle data line); and a ruthenium chloride norbornadiene (nbd) dimer ([$RhCl(nbd)_2$]; bottom data line).
Figure 14C:
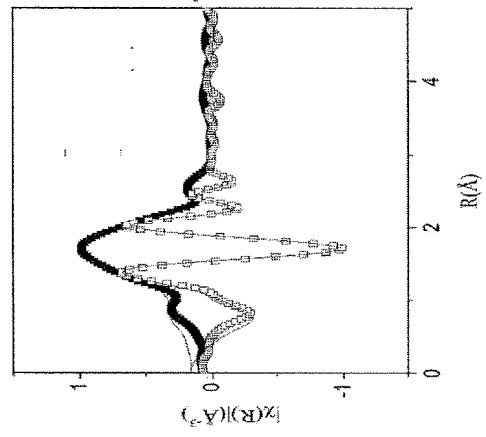
FIG. 14C is a graph showing the extended x-ray absorption fine structure (EXAFS) data (squares) and best fits (lines) for a chiral diene-containing metal-organic framework ($E_2$-MOF) of the presently disclosed subject matter. Data is displayed in R-space containing both magnitude of Fourier Transform (filled squares) and real (open squares) components. An R-factor of 0.01 was obtained for the fit.

Due to the positional disorder and incomplete metalation of the diene moiety, investigation of the Rh-coordination environment could not be performed by traditional crystallographic techniques. X-ray absorption fine structure spectroscopy (XAFS) at the Rh K-edge was used to investigate the local coordination environment of Rh in E$_2$-MOF.RhCl, as well as Rh-metalated H$_2$L, and the dimeric [RhCl(nbd)]$_2$ standard. Data were processed and analyzed using the Athena and Artemis programs of the IFEFFIT package (see Ravel et al., Synchrotraon Radiat., 2005, 12, 537) based on FEFF 6. See Rehr et al., Rev. Mod. Phys., 2000, 72, 621. E$_2$-MOF.RhCl was fitted with a monomeric model where the Rh coordination sphere is occupied by norbornadiene, chloride, and a THF solvent molecule. See FIG. 14C. The spectra for [RhCl(nbd)]$_2$ was fitted by the corresponding crystal structure. A significant peak was observed at approximately 2 Å, attributable to a second Rh—Cl direct scattering path, clearly differentiating it from the spectra of E$_2$-MOF.RhCl. Amplitude from Rh—Rh direct scattering paths can be observed at ~3.2 Å. The RhCl—H$_2$L system was best fitted with a combination of monomeric (~85%) and dimeric (~15%) models (See FIG. 14D), which was confirmed by $^1$H NMR spectroscopy.

Example 24

Catalysis of Asymmetric 1,4-Addition Reactions of Arylboronic Acids to α,β-Unsaturated Ketones with Chiral Diene MOF Post-Synthetic Metalation of E$_2$-MOF with [RhCl(C$_2$H$_4$)$_2$]$_2$:

Freshly prepared E$_2$-MOF (1.50 mg, 0.529 μmol) was weighed onto a filter paper and then charged into a 1 dram vial. After addition of THF (1.5 mL) and [RhCl(C$_2$H$_4$)$_2$]$_2$ (42 μL, 0.53 μmol, 0.0125 M solution in THF), the mixture was allowed to stand overnight, and then the metalated E$_2$-MOF was centrifuged out of suspension and washed with THF. ICP-MS analysis gave 66% Rh-loading of the chiral organic ligand.

Exemplary Procedure for E$_2$-MOF.RhCl Catalyzed Asymmetric 1,4-Addition Reactions:

E$_2$-MOF (1.50 mg, 0.529 μmol) was metalated with [RhCl(C$_2$H$_4$)$_2$]$_2$ (42 μL, 0.53 μmol, 0.0125 M solution in THF) as above. A mixture of 2-cyclohexenone (20a) (340 μL, 3.49 mmol), phenylboronic acid (21a) (510.6 mg, 4.188 mmol), E$_2$-MOF.RhCl (0.349 μmol Rh) in toluene (1.2 mL) and H$_2$O (2.3 mL) was refluxed under nitrogen atmosphere at 100° C. for 40 h. The mixture was extracted with Et$_2$O. After evaporation of the solvent, the residue was subjected to column chromatography on silica gel (hexane/CHCl$_3$/ethyl acetate=20/10/1) to give (R)-3-phenylcyclohexanone (97% yield, 93% ee).

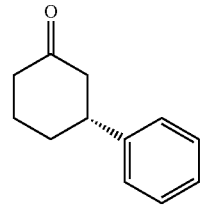 [SMILES: O=C1CCC[C@@H](c2ccccc2)C1]

(R)-3-Phenylcyclohexanone. $^1$H NMR (CDCl$_3$): δ 1.73-1.92 (m, 2H), 2.05-2.12 (m, 1H), 2.12-2.20 (m, 1H), 2.38 (td, J=13.3, 5.8 Hz, 1H), 2.43-2.50 (m, 1H), 2.50-2.63 (m, 2H), 3.01 (tt, J=12.0, 3.8 Hz, 1H), 7.20-7.27 (m, 3H), 7.34 (t, J=7.5 Hz, 2H). The ee was measured by HPLC (Chiralpak AD, 0.6 mL/min, hexanes/2-propanol=99/1, 210 nm, t$_1$=20.3 min (minor), t$_2$=24.8 min (major)).

Analogous reactions were performed using 2-cyclohexenone (20a), 2-cyclopentenone (20b), 2-cycloheptenone (20c), or 4-hexen-3-one (20d) with phenylboronic acid (21a), 4-fluorophenylboronic acid (21b), or 4-methoxyphenylboronic acid (21c) as the substrates to provide:

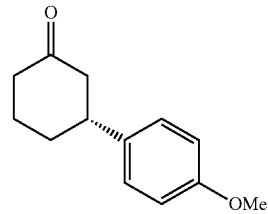 [SMILES: COc1ccc([C@@H]2CCCC(=O)C2)cc1]

(R)-3-(4-Methoxy)cyclohexanone. $^1$H NMR (CDCl$_3$): δ 1.70-1.87 (m, 2H), 2.02-2.09 (m, 1H), 2.09-2.18 (m, 1H), 2.37 (td, J=13.0, 5.8 Hz, 1H), 2.41-2.53 (m, 2H), 2.57 (ddt, J=14.0 Hz, 4.3, 2.0 Hz, 1H), 2.96 (tt, J=11.8, 3.8 Hz, 1H), 3.80 (s, 3H), 6.87 (d, J=8.8 Hz, 2H), 7.14 (d, J=8.8 Hz, 2H). The ee was measured by HPLC (Chiralcel OD-H, 0.6 mL/min, hexanes/2-propanol=97/3, 210 nm, t$_1$=22.3 min (major), t$_2$=23.7 min (minor)).

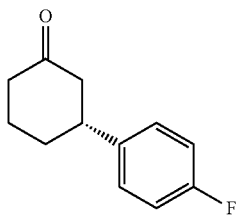 [SMILES: O=C1CCC[C@@H](c2ccc(F)cc2)C1]

(R)-3-(4-Fluorophenyl)cyclohexanone. $^1$H NMR (CDCl$_3$): δ 1.71-1.87 (m, 2H), 2.03-2.10 (m, 1H), 2.10-2.18 (m, 1H), 2.37 (td, J=13.3, 6.5 Hz, 1H), 2.42-2.52 (m, 2H), 2.57 (ddt, J=14.0, 4.0, 2.0 Hz, 1H), 2.99 (tt, J=11.8, 3.8 Hz, 1H), 7.01 (app t, $J_{H-F}$=8.9 Hz, $J_{H-H}$=8.9 Hz, 2H), 7.17 (dd, $J_{H-F}$=5.3 Hz, $J_{H-H}$=8.9 Hz, 2H). The ee was measured by HPLC (Chiralpak AD, 0.6 mL/min, hexanes/2-propanol=95/5, 210 nm, $t_1$=11.9 min (minor), $t_2$=14.4 min (major)).

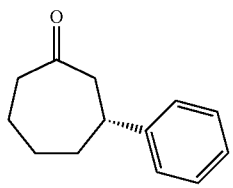 [SMILES: O=C1CCCC[C@@H](c2ccccc2)C1]

(R)-3-Phenylcycloheptanone. $^1$H NMR (CDCl$_3$): δ 1.44-1.56 (m, 1H), 1.66-1.80 (m, 2H), 1.95-2.15 (m, 3H), 2.59 (dd, J=9.5, 4.2 Hz, 2H), 2.62-2.67 (m, 1H), 2.86-2.93 (m, 1H), 2.94 (t, J=12.5 Hz, 1H), 7.15-7.23 (m, 3H), 7.30 (t, J=7.5 Hz, 2H). The ee was measured by HPLC (Chiralcel OD-H, 0.6 mL/min, hexanes/2-propanol=95/5, 210 nm, $t_1$=15.0 min (minor), $t_2$=16.3 min (major)).

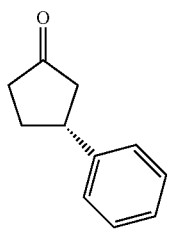 [SMILES: O=C1CC[C@@H](c2ccccc2)C1]

(R)-3-Phenylcyclopentanone. $^1$H NMR (CDCl$_3$): δ 1.96-2.08 (m, 1H), 2.28-2.42 (m, 2H), 2.43-2.54 (m, 2H), 2.70 (dd, J=18.0, 7.5 Hz, 1H), 3.40-3.50 (m, 1H), 7.25-7.31 (m, 3H), 7.37 (t, J=7.5 Hz, 2H). The ee was measured by GC (γ-dex 225. Inj: 250° C. Det: 250° C. Column temp: 80° C., ramp of 1° C./min to 200° C. and held for 10 min. Column flow: 1.0 mL/min).

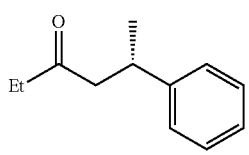

(S)-5-Phenyl-3-hexanone. $^1$H NMR (CDCl$_3$): δ 0.99 (t, J=7.3 Hz, 3H), 1.26 (d, J=7.0 Hz, 3H), 2.29 (dq, J=17.5, 7.3 Hz, 1H), 2.35 (dq, J=17.5, 7.3 Hz, 1H), 2.63 (dd, J=16.0, 8.0 Hz, 1H), 2.73 (dd, J=16.0, 6.5 Hz, 1H), 3.27-3.38 (m, 1H), 7.16-7.21 (m, 1H), 7.21 (d, J=7.3 Hz, 2H), 7.29 (t, J=7.3 Hz, 2H). The ee was measured by HPLC (Chiralpak AD, 0.6 mL/min, hexanes/2-propanol=99.8/0.2, 210 nm, $t_1$=17.1 min (major), $t_2$=18.4 min (minor)).

Discussion:

E$_2$-MOF.RhCl is a highly effective catalyst for 1,4-additions of arylboronic acids to α,β-unsaturated ketones with high turnover numbers (TON). The reaction of 2-cyclohexenone (20a) with phenylboronic acid (21a) in the presence of E$_2$-MOF.RhCl(0.01 mol % Rh) gave the addition product in 97% yield and 93% ee. See Table 13, entry 1. At 0.005 mol % Rh loading, the reaction proceeded to give the addition product in 67% yield and 94% ee, leading to a high TON of 13400. See Table 13, entry 2. These results are comparable with those of the homogeneous control catalyst. See Table 13, entry 3. E$_2$-MOF.RhCl catalyzed 1,4-addition reactions have a substrate variability for both arylboronic acids and α,β-unsaturated ketones. Both electron donating groups and electron withdrawing groups can be installed to the aromatic ring of arylboronic acids, giving the addition products in high yields and high ee's. See Table 13, entries 4 and 5. For α,β-unsaturated ketones, the reactions proceeded with five-membered ring and seven-membered ring substrates (see Table 13, entries 6 and 7) as well as with a linear ketone (84% yield, 90% ee; Table 13, entry 8). Heterogeneity of the 1,4-addition reaction was confirmed by ICP-MS, which indicates the leaching of only small amounts of Rh (1.3%) and Zr (<0.01%) into the solution. However, recovered E$_2$-MOF.RhCl from the reaction mixture did not show high catalytic activity, which might be due to the gradual loss of MOF crystallinity during the course of the reaction.

TABLE 13

Asymmetric 1,4-additions of Arylboronic Acids to α,β-Unsaturated Ketones with E2-MOF•RhCl and Homogeneous Catalysts.

| entry | enone | aryl boronic acid | catalyst loading (mol % Rh) | yield (%)[b] | ee (%)[c] |
|---|---|---|---|---|---|
| 1 | 20a | 21a | 0.01 | 97 | 93 |
| 2 | 20a | 21a | 0.005 | 67 | 94 |
| 3[d] | 20a | 21a | 0.005 | 80 | 95 |
| 4 | 20a | 21b | 0.025 | 90 | 94 |
| 5 | 20a | 21c | 0.01 | 84 | 96 |
| 6 | 20b | 21a | 0.1 | 82 | 89 |
| 7[e] | 20c | 21a | 0.1 | 93 | 70 |
| 8[e] | 20d | 21a | 0.25 | 84 | 90 |

[a] Reaction conditions: 20 (1 equiv.), 21 (1.2 equiv.), toluene, H$_2$O at 100° C. for 40 h.
[b] Isolated yield.
[c] Determined by chiral HPLC.
[d] [RhCl(C$_2$H$_4$)$_2$]$_2$ and Me$_2$L were used as catalyst.
[e] 2.0 equiv of PhB(OH)$_2$.

Example 25

Catalysis of Asymmetric 1,2-Addition Reactions of Arylboronic Acids to Aldimines with Chiral Diene MOF Post-Synthetic Metalation of E$_2$-MOF with Rh(Acac)(C$_2$H$_4$)$_2$:

Freshly prepared E$_2$-MOF (6.0 mg, 2.12 μmol) was weighed onto a filter paper and then charged into a 1 dram vial. After addition of THF (1.5 mL) and Rh(acac)(C$_2$H$_4$)$_2$ (169 μL, 2.12 μmol, 0.0125 M solution in THF), the mixture was allowed to stand overnight, and then the metalated E$_2$-MOF was centrifuged out of suspension and washed with THF. ICP-MS analysis gave 13% Rh-loading of the organic bridging ligand.

Exemplary Procedure for E$_2$-MOF.Rh(Acac) Catalyzed Asymmetric Addition Reactions of Aldimines:

E$_2$-MOF (6.0 mg, 2.12 μmol) was metalated with Rh(acac)(C$_2$H$_4$)$_2$ (169 μL, 2.12 μmol, 0.0125 M solution in THF) as above. A mixture of N-(4-chlorophenyl)methylidene-4-methylbenzenesulfonamide 22a (2.8 mg, 9.5 μmol), phenylboronic acid 21a (2.3 mg, 19 mmol), E$_2$-MOF.Rh(acac) (0.29 μmol Rh) in 1,4-dioxane (0.24 mL) was stirred under nitrogen atmosphere at 100° C. for 20 h. After centrifugation, MeOH was added to the supernatant and the mixture was stirred for 30 min. After evaporation of the solvent, the residue was subjected to preparative TLC (silica gel, hexane/ethyl acetate=3/1) to give (S)-N-[(4-chlorophenyl)phenylmethyl]-4-methylbenzenesulfonamide (99% yield, 98% ee).

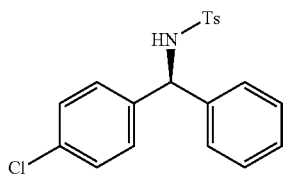 [SMILES: Cc1ccc(S(=O)(=O)N[C@@H](c2ccccc2)c2ccc(Cl)cc2)cc1]

(S)-N-[(4-chlorophenyl)phenylmethyl]-4-methylbenzenesulfonamide (23a). $^1$H NMR (CDCl$_3$): 2.39 (s, 3H), 5.11 (d, J=7.0 Hz, 1H), 5.53 (d, J=7.0 Hz, 1H), 7.02-7.08 (m, 4H), 7.13-7.20 (m, 4H), 7.20-7.24 (m, 3H), 7.55 (d, J=8.5 Hz, 2H). The ee was measured by HPLC (Chiralcel OD-H, 0.5 mL/min, hexanes/2-propanol=80/20, 230 nm, t$_1$=15.8 min (major), t$_2$=20.7 min (minor)).

Analogous reactions were performed using N-(4-chlorophenyl)methylidene-4-methylbenzenesulfonamide 22a, N-(phenyl)methylidend-4-methylbenzenesulfonamide 22b, or N-(4-methoxyphenyl)methylidne-4-methylbenzenesulfonamide 22c as the aldimine and phenylboronic acid (21a), 4-fluorophenylboronic acid (21b), or 4-methoxyphenylboronic acid (21c) as the boronic acid to provide:

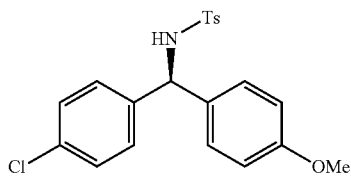 [SMILES: COc1ccc([C@H](NS(=O)(=O)c2ccc(C)cc2)c2ccc(Cl)cc2)cc1]

(S)-N-[(4-Chlorophenyl)(4-methoxyphenyl)methyl]-4-methylbenzenesulfonamide. $^1$H NMR (CDCl$_3$): 2.39 (s, 3H), 3.74 (s, 3H), 5.31-5.38 (br, 1H), 5.48 (d, J=7.5 Hz, 1H), 6.72 (d, J=8.8 Hz, 2H), 6.94 (d, J=8.8 Hz, 2H), 7.06 (d, J=8.3 Hz, 2H), 7.15 (app t, J=8.5 Hz, 4H), 7.54 (d, J=8.3 Hz, 2H). The ee was measured by HPLC (Chiralcel OD-H, 0.5 mL/min, hexanes/2-propanol=80/20, 230 nm, t$_1$=26.1 min (minor), t$_2$=35.1 min (major)).

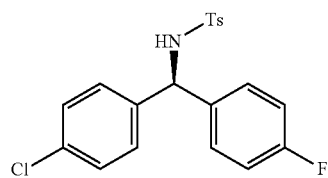 [SMILES: Cc1ccc(S(=O)(=O)N[C@@H](c2ccc(F)cc2)c2ccc(Cl)cc2)cc1]

(S)-N-[(4-Chlorophenyl)(4-fluorophenyl)methyl]-4-methylbenzenesulfonamide. $^1$H NMR (CDCl$_3$): 2.40 (s, 3H), 5.42 (d, J=7.5 Hz, 1H), 5.52 (d, J=7.5 Hz, 1H), 6.89 (app t, =8.8 Hz, J$_{H-F}$=8.8 Hz, 2H), 6.98-7.05 (m, 4H), 7.14 (d, J=8.3 Hz, 2H), 7.17 (d, J=8.5 Hz, 2H), 7.53 (d, J=8.3 Hz, 2H); $^{13}$C NMR (CDCl$_3$): 21.4, 60.0, 115.5 (J$_{C-F}$=21.6 Hz), 127.1, 128.6, 128.7, 129.0 (J$_{C-F}$=8.3 Hz), 129.4, 133.6, 135.8 (J$_{C-F}$=3.3 Hz), 137.0, 138.7, 143.5, 162.1 (J$_{C-F}$=247.2 Hz). HRMS (ESI) calcd for [M+Na] C$_{20}$H$_{17}$ClFNO$_2$SNa 412.0550. found 412.0550. The ee was measured by HPLC (Chiralcel OD-H, 0.5 mL/min, hexanes/2-propanol=80/20, 230 nm, t$_1$=18.7 min (major), t$_2$=20.9 min (minor)).

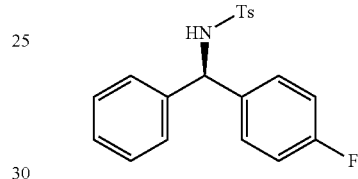

(R)-N-[(4-Fluorophenyl)phenylmethyl]-4-methylbenzenesulfonamide. $^1$H NMR (CDCl$_3$): 2.38 (s, 3H), 5.12-5.31 (br, 1H), 5.55 (d, J=7.0 Hz, 1H), 6.89 (app t, =8.8 Hz, J$_{H-F}$=8.8 Hz, 2H), 7.03-7.12 (m, 4H), 7.14 (d, J=8.3 Hz, 2H), 7.18-7.25 (m, 3H), 7.55 (d, J=8.3 Hz, 2H). The ee was measured by HPLC (Chiralcel OD-H, 0.5 mL/min, hexanes/2-propanol=80/20, 235 nm, t$_1$=15.4 min (minor), t$_2$=18.2 min (major)).

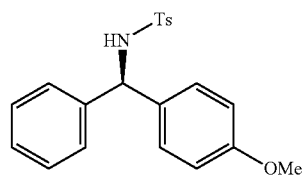 [SMILES: COc1ccc([C@H](NS(=O)(=O)c2ccc(C)cc2)c2ccccc2)cc1]

(R)-N-[(4-Methoxyphenyl)phenylmethyl]-4-methylbenzenesulfonamide $^1$H NMR (CDCl$_3$): 2.38 (s, 3H), 3.75 (s, 3H), 5.08 (d, J=7.0 Hz, 1H), 5.52 (d, J=7.0 Hz, 1H), 6.73 (d, J=8.8 Hz, 2H), 6.99 (d, J=8.8 Hz, 2H), 7.08-7.12 (m, 2H), 7.14 (d, J=8.0 Hz, 2H), 7.16-7.23 (m, 3H), 7.55 (d, J=8.0 Hz, 2H). The ee was measured by HPLC (Chiralcel OD-H, 0.5 mL/min, hexanes/2-propanol=80/20, 210 nm, t$_1$=19.7 min (minor), t$_2$=30.0 min (major)).

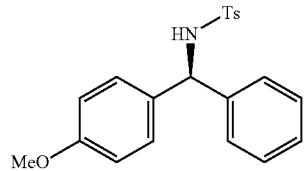 [SMILES: COc1ccc([C@@H](NS(=O)(=O)c2ccc(C)cc2)c2ccccc2)cc1]

(S)-N-[(4-Methoxyphenyl)phenylmethyl]-4-methylbenzenesulfonamide. The ee was measured by HPLC (Chiralcel OD-H, 0.5 mL/min, hexanes/2-propanol=80/20, 210 nm, $t_1$=19.3 min (major), $t_2$=30.5 min (minor)).

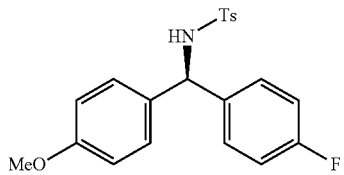 [SMILES: COc1ccc([C@@H](NS(=O)(=O)c2ccc(C)cc2)c2ccc(F)cc2)cc1]

(R)-N-[(4-Fuluorophenyl)(4-methoxyphenyl)methyl]-4-methylbenzenesulfon-amide. $^1$H NMR (CDCl$_3$): 2.38 (s, 3H), 3.75 (s, 3H), 5.10-5.28 (br, 1H), 5.49 (d, J=7.0 Hz, 1H), 6.72 (d, J=8.5 Hz, 2H), 6.85-6.91 (m, 2H), 6.95 (d, J=8.5 Hz, 2H), 7.08 (dd, $J_{H-H}$=8.5, $J_{H-F}$=5.0 Hz, 2H), 7.14 (d, J=8.3 Hz, 2H), 7.54 (d, J=8.3 Hz, 2H). The ee was measured by HPLC (Chiralcel OD-H, 0.5 mL/min, hexanes/2-propanol=80/20, 210 nm, $t_1$=21.8 min (major), $t_2$=31.8 min (minor)).

Recyclability Test for E$_2$-MOF.Rh(Acac) Catalyzed Asymmetric 1,2-Addition of Aldimine:

increasing the catalyst loading but the ee's decrease as the catalyst loading increased. The ee's of the E$_2$-MOF.Rh (acac)-catalyzed reactions remained constant at different catalyst loadings. Without being bound to any one theory, this difference can be attributed to the desirable site isolation provided by the MOF, which affords the desired monomeric Rh species. In contrast, the homogeneous control can form oligomeric species which might be less enantioselective.

E$_2$-MOF.Rh(acac)-catalyzed 1,2-addition reactions have a broad substrate scope for both arylboronic acids and aldimines to give addition products with excellent ee's (ranging from 97% to >99%). The reaction works with aldimines and arylboronic acids having electron donating groups or electron withdrawing groups. See Table 15, entries 1-6.

Figure 15:
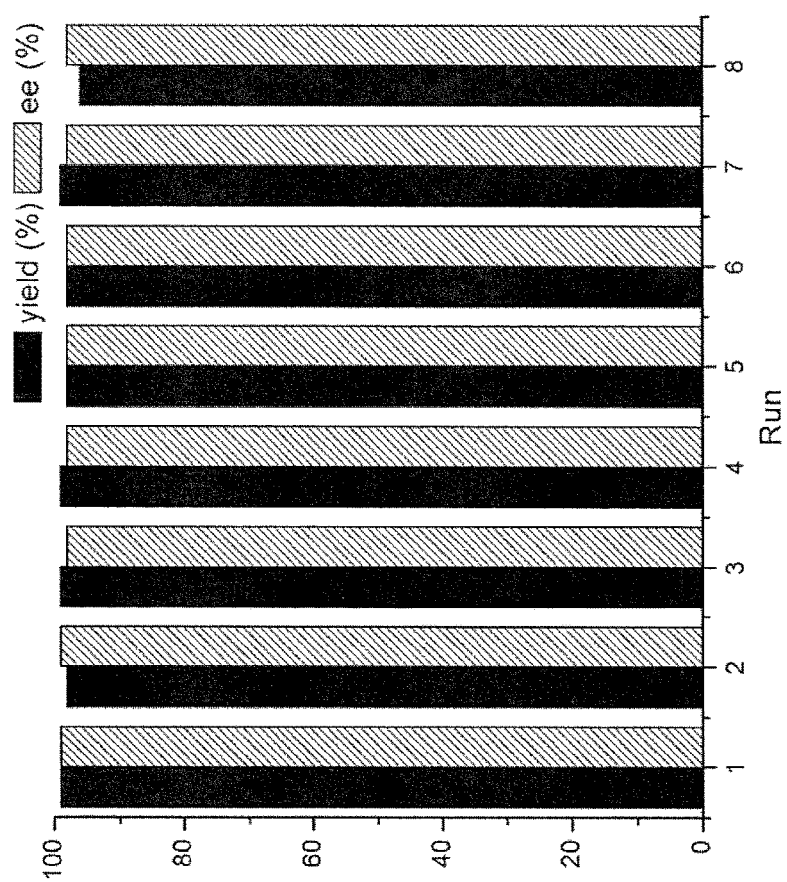
FIG. 15 is a bar graph showing the yield (percentage, %) and enantiomeric excess (e.e.) (%) of 1,2-addition product prepared using a chiral diene-containing metal-organic framework ($E_2$-MOF) catalyst, either for the first time (run 1) or recycled for additional reaction runs (runs 2-8).

Several studies proved that E$_2$-MOF.Rh(acac) is a truly heterogeneous and reusable catalyst. First, the MOF catalyst (6 mol % Rh) could be recycled and reused for at least 7 times without loss of yield and ee. See FIG. 15. Second, the crystallinity of the MOF catalyst recovered from the first and eighth runs was still maintained as the PXRD of the recovered catalyst remained the same as the freshly prepared E$_2$-MOF.Rh(acac). See FIG. 14B. ICP-MS analysis showed negligible leaching of Rh (0.49%) and Zr (0.07%) during the

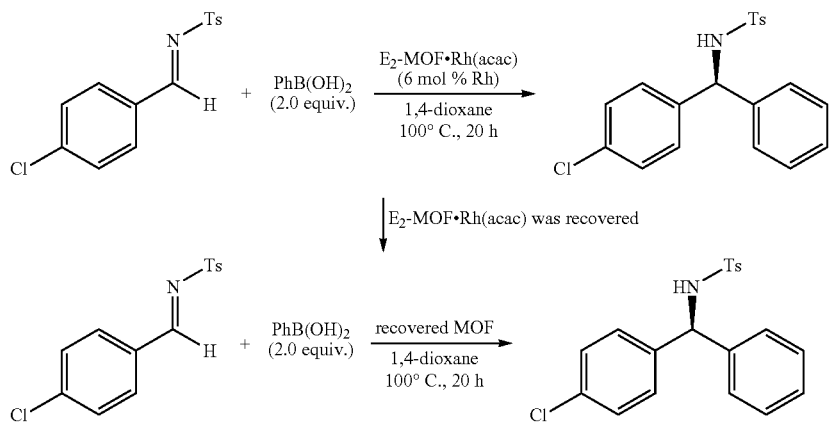

Scheme 24. Recycle of E$_2$-MOF•Rh(acac) for the 1,2-addition reaction of boronic acid 21a to aldimine 22a E$_2$-MOF (21.7 mg, 7.66 µmol) was metalated with Rh(acac)(C$_2$H$_4$)$_2$ (612 µL, 7.66 µmol, 0.0125 M solution in THF) as described above. As shown in Scheme 24, above, a mixture of aldimine 22a (5.0 mg, 17.2 µmol), phenyboronic acid (21a) (4.2 mg, 34.4 mmol), and E$_2$-MOF.Rh(acac) (1.03 µmol Rh) in 1,4-dioxane (0.86 mL) was stirred under nitrogen atmosphere at 100° C. for 20 h. The solid catalyst was separated via centrifugation, and then the supernatant was concentrated on a rotary evaporator and subjected to preparative TLC (silica gel, hexanes/ethyl acetate=3/1) to give 23a. The recovered solid catalyst was used for subsequent reactions.

Discussion:

Asymmetric 1,2-addition of arylboronic acids to aldimines proceeded in the presence of E$_2$-MOF.Rh(acac). At 0.2 mol % Rh loading, the reaction gave the addition product in 55% yield and 98% ee. See Table 14, entry 1. Quantitative yield of the addition product was obtained at 3 mol % Rh loading. See Table 14, entry 3. Interestingly, E$_2$-MOF.Rh(acac) performed better than the homogeneous control catalyst both in terms of yields and ee's. For the homogeneous control, the product yield can be increased by reaction. Also, the progress of the reaction was stopped by removing the MOF catalyst from the reaction mixture, indicating that the supernatant is inactive in catalyzing the 1,2-addition reactions.

TABLE 14

Asymmetric 1,2-Addition of Aldimine 22a with E$_2$-MOF•Rh(acac) and homogeneous control catalyst.

| entry | catalyst | catalyst loading | yield (%)$^b$ | ee (%)$^c$ |
|---|---|---|---|---|
| 1 | E$_2$-MOF•Rh(acac) | 0.2 mol % | 55 | 98 |
| 2 | E$_2$-MOF•Rh(acac) | 0.6 mol % | 71 | 98 |
| 3 | E$_2$-MOF•Rh(acac) | 3 mol % | 99 | 98 |
| 4 | Rh(acac)/LMe$_2$ | 0.2 mol % | 11 | 94 |
| 5 | Rh(acac)/LMe$_2$ | 0.6 mol % | 55 | 89 |
| 6 | Rh(acac)/LMe$_2$ | 3 mol % | 87 | 83 |

$^a$ 22a (1.0 equiv.), 21a (2.0 equiv.), catalyst, 1,4-dioxane, 100° C., 20 h.
$^b$NMR yield based on internal standard.
$^c$Determined by chiral HPLC analysis.
Ts = p-toluenesulfonyl

TABLE 15

Asymmetric Addition of Arylboronic Acids to N-Tosylaldimines.

| entry | Aryl Substituent on Aldimine | Aryl Substituent on Boronic Acid | yield (%)[b] | ee (%)[c] |
|---|---|---|---|---|
| 1 | Cl (22a) | H (21a) | 99 | 98 |
| 2 | Cl (22a) | F (21b) | 95 | 99 |
| 3 | Cl (22a) | OMe (21c) | 80 | 98 |
| 4 | H (22b) | F (21b) | 97 | 99 |
| 5 | H (22b) | OMe (21c) | 96 | 97 |
| 6 | OMe (22c) | H (21a) | 98 | 99 |
| 7 | OMe (22c) | F (21b) | 99 | >99 |

[a] 22 (1.0 equiv.), 21 (2.0 equiv.), E$_2$-MOF•Rh(acac) (3 mol % Rh), 1,4-dioxane, 100° C., 20 h.
[b] NMR yield based on internal standard.
[c] Determined by chiral HPLC analysis.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An asymmetric heterogeneous catalyst comprising a crystalline and porous metal-organic framework (MOF), wherein said crystalline and porous MOF comprises periodic repeats of a coordination complex comprising (a) a metal-based secondary building unit (SBU), wherein said metal-based SBU comprises a first metal, and (b) a chiral bridging ligand, wherein said chiral bridging ligand is coordinatively bonded to more than one SBU, wherein said chiral bridging ligand is further complexed to a second metal to provide a catalytic moiety, and wherein said chiral bridging ligand is a dicarboxylate-substituted chiral bisphosphine or a dicarboxylate-substituted chiral bicyclo[2.2.2]octane-2,5-diene.

2. The catalyst of claim 1, wherein said catalyst is prepared by providing the chiral bridging ligand, contacting the chiral bridging ligand with a first metal source to obtain a MOF, and further comprising contacting the MOF with a second metal source to metalate the organic bridging ligand.

3. The catalyst of claim 1, further comprising a non-chiral bridging ligand, optionally wherein the non-chiral bridging ligand is 4,4'((2-nitro-[1,1'-biphenyl]-4,4'-diyl)bis(ethyne-2,1-diyl))dibenzoic acid or 4,4'-(2-nitro[1,1'-biphenyl])bisbenzoic acid.

4. The catalyst of claim 1, wherein the SBU is a Zr-oxo cluster.

5. The catalyst of claim 1, wherein the second metal is Ru or Rh.

6. A method for preparing the asymmetric heterogeneous catalyst of claim 1, said method comprising providing the chiral bridging ligand; contacting the chiral bridging ligand with a first metal source to obtain the crystalline and porous MOF; and contacting the crystalline and porous MOF with a second metal source to metalate the chiral bridging ligand.

7. The method of claim 6, wherein the first metal source is ZrCl$_4$.

8. The method of claim 6, wherein the second metal source is Ru(cyclooctadiene)(2-Me-allyl)$_2$, Rh(norbornadiene)$_2$BF$_4$, [RhCl(C$_2$H$_2$)$_2$]$_2$, or Rh(acetylacetonate)(C$_2$H$_4$)$_2$.

9. The method of claim 6, wherein the chiral bridging ligand and the first metal source are contacted in a solvent or mixture of solvents selected based on solvent molecule size, such that the sizes and/or shapes of internal pores, cavities, and/or open channels in the crystalline and porous MOF can be tailored to enhance catalytic activity and selectivity.

10. The method of claim 9, wherein the solvent comprises dimethylformamide (DMF).

11. A method for preparing an asymmetric compound comprising contacting a substrate capable of forming an asymmetric product by an asymmetric reaction with an asymmetric heterogeneous catalyst of claim 1.

12. The method of claim 11, wherein the asymmetric reaction is selected from the group consisting of hydrogenation; isomerization, optionally the isomerization of an allylamine, an allyl alcohol, or an α,β-unsaturated ketone; allylic substitution; a coupling reaction, optionally wherein the coupling reaction is a Buchwald-Hartwig amination, an intramolecular Heck reaction, or an intermolecular Heck reaction; conjugate addition, optionally wherein the conjugate addition is a Michael addition or an azo-Michael addition; an aldol reaction; a Mannich-type reaction; nucleophilic addition, optionally wherein the nucleophilic addition is to a carbonyl or imine group and/or wherein the nucleophilic addition is a cyanation, a propargylation, an allylation, a dienylation, an arylation, an alkenylation, or an alkylation; hydroformylation; hydroacylation; hydroboration; hydroamination; intra- or intermolecular hydrosilylation; an α-substitution reaction, optionally wherein the α-substitution reaction is a protonation, a fluorination, an amination, an arylation, or an orthoester alkylation; an ene reaction; a Diels-Alder reaction; a Pauson-Khand reaction; an Alder-Ene reaction, an enyne intramolecular cyclization; a [2+2+2] cycloaddition; a [3+2] cycloaddition; and a ring-opening reaction.

13. The method of claim 11, wherein the asymmetric reaction is performed in the presence or absence of a solvent, optionally wherein a solvent is present, further optionally wherein the solvent is supercritical carbon dioxide.

14. The method of claim 11, wherein the asymmetric reaction is performed in a flow reactor.

15. The method of claim 11, wherein the asymmetric reaction is selected from the group consisting of 1,4-addition of an arylboronic acid to an α,β-unsaturated ketone; 1,2-addition of trimethylaluminum to an α,β-unsaturated ketone, 1,2-addition of an arylboronic acid to an aldimine, hydrogenation of a β-keto ester, hydrogenation of a substituted alkene, reductive cyclization of a 1,6-enyne, an Alder-Ene reaction, and a Pauson-Khand reaction.

16. The method of claim 11, wherein the contacting is performed by contacting the substrate with about 3 mole percentage or less of the catalyst as compared to the substrate.

17. A method of preparing a compound, wherein the method comprises using a catalyst of claim 1 to catalyze a multi-step reaction or to catalyze sequential reactions.

18. A method of preparing a compound, wherein the method comprises using a plurality of catalysts of claim 1 to catalyze sequential reactions or to catalyze a multi-step reaction.

* * * * *